US012134769B2

(12) United States Patent
Yao et al.

(10) Patent No.: US 12,134,769 B2
(45) Date of Patent: Nov. 5, 2024

(54) MICRORNA-198 AS A TUMOR SUPPRESSOR IN OVARIAN CANCER

(71) Applicant: Baylor College of Medicine, Houston, TX (US)

(72) Inventors: Qizhi Yao, Houston, TX (US); Christian Marin-Muller, League City, TX (US); Changyi Chen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 648 days.

(21) Appl. No.: 17/236,851

(22) Filed: Apr. 21, 2021

(65) Prior Publication Data
US 2022/0177889 A1 Jun. 9, 2022

Related U.S. Application Data

(63) Continuation of application No. 16/299,986, filed on Mar. 12, 2019, now Pat. No. 11,008,573, which is a continuation of application No. 15/955,451, filed on Apr. 17, 2018, now abandoned, which is a continuation of application No. 15/372,759, filed on Dec. 8, 2016, now abandoned, which is a continuation of application No. 14/615,168, filed on Feb. 5, 2015, now Pat. No. 9,546,365, which is a continuation of application No. 13/567,852, filed on Aug. 6, 2012, now Pat. No. 8,987,224.

(60) Provisional application No. 61/515,416, filed on Aug. 5, 2011.

(51) Int. Cl.
| | | |
|---|---|---|
| C12N 15/113 | (2010.01) | |
| A61K 31/7088 | (2006.01) | |
| A61K 31/7105 | (2006.01) | |
| A61K 31/713 | (2006.01) | |
| A61K 45/06 | (2006.01) | |
| A61K 51/00 | (2006.01) | |
| A61N 5/10 | (2006.01) | |

(52) U.S. Cl.
CPC ...... *C12N 15/1135* (2013.01); *A61K 31/7088* (2013.01); *A61K 31/7105* (2013.01); *A61K 31/713* (2013.01); *A61K 45/06* (2013.01); *A61K 51/00* (2013.01); *A61N 5/10* (2013.01); *C12N 15/113* (2013.01); *A61K 2300/00* (2013.01); *C12N 2310/141* (2013.01); *C12N 2320/30* (2013.01); *C12N 2320/31* (2013.01); *Y10S 977/704* (2013.01); *Y10T 428/13* (2015.01)

(58) Field of Classification Search
CPC .............. C12N 15/1135; C12N 15/113; C12N 2310/141
See application file for complete search history.

(56) References Cited

U.S. PATENT DOCUMENTS

| 8,071,562 B2 | 12/2011 | Bader et al. |
| 9,546,365 B2 | 1/2017 | Yao et al. |
| 2006/0188883 A1 | 8/2006 | Murray et al. |
| 2008/0050744 A1 | 2/2008 | Brown et al. |
| 2010/0310583 A1 | 12/2010 | Lieberman et al. |
| 2011/0312516 A1 | 12/2011 | Orntoft et al. |

OTHER PUBLICATIONS

Ali et al (Cancer Biology, vol. 11, 2001: pp. 15-22).
ATCC web page on THLE-2 cells retrieved from http://www.atcc.org/products/aii/CRL-2706.aspx on Aug. 25, 2014.
Bharadwaj et al (Mol Cancer Res 2008; 6:1755-1765).
Heng et al (J. Cell. Physiol. 220: 538-547, 2009).
Ho, Mitchell, "Advances in Liver Cancer Antibody Therapies: A Focus on Glypican-3 and Mesothelin", BioDrugs 25(5): 275-284; Oct. 1, 2011.
Huang, Chia-Yen et al., "Serum Mesothelin in Epithelial ovarian Carcinoma: A New Screening Marker and Prognostic Factor", Anticancer Research 26: 4721-4728 (2006).
Marin-Muller et al. "MicroRNA-198 Plays an Important Role in Mesothelin-Overexpressing Pancreatic Cancer Pathogenis" Abstract, Feb. 1, 2011, Sixth Annual Academic Surgical Congress.
Marin-Muller et al. "The Role of miR-198 in the Regulatory Circuitry of Mesothelein-overexpressing Pancreatic Cancer Pathogenesis", Department of Surgery, Department of Molecular Virology and Microbiology, Baylor College of Medicine (BCM), Houston, Texas 77030, Nov. 19, 2010, BCM Molecular Virology and Microbiology Retreat, Abstract and Poster.
Min Li et al., "Mesothelin is a malignant factor and therapeutic vaccine target for pancreatic cancer" Mol Cancer Ther 2008; 7:286-296.

(Continued)

*Primary Examiner* — Richard A Schnizer
(74) *Attorney, Agent, or Firm* — Norton Rose Fulbright US LLP

(57) ABSTRACT

A novel network of tumorigenic prognostic factors is identified that plays a critical role in advanced pancreatic cancer (PC) pathogenesis. This interactome is interconnected through a central tumor suppressive microRNA, miR-198, which is able to both directly and indirectly modulate expression of the various members of this network to alter the molecular makeup of pancreatic tumors, with important clinical implications. When this tumor signature network is intact, miR-198 expression is reduced and patient survival is dismal; patients with higher miR-198 present an altered tumor signature network, better prognosis and increased survival. Further, according to the present disclosure, MiR-198 replacement reverses tumorigenicity in vitro and in vivo. As such, an embodiment of the disclosure is a method of treating cancer in an individual, comprising the step of increasing the level of active microRNA-198 molecules in the pancreatic cancer tumor cells of the individual by an amount sufficient to cause an improvement in the pancreatic cancer in the individual.

10 Claims, 39 Drawing Sheets

Specification includes a Sequence Listing.

(56) References Cited

OTHER PUBLICATIONS

Nomura, Ryohei et al., "Mesothelin Expression is a Prognostic Factor in Cholangiocellular Carcinoma", Int. Surg: 98:164-169 (2103).
Pedram Argani et al., "Mesothelin is Overexpresse in the Vast Majority of Ductal Adenocarcinomas of Pancreas: Identification of a New Pancreatic Cancer Marker by Serial Analysis of Gene Expression (SAGE)", Clin Cancer Res, 2001; 7:3862-3868.
Pramanik et al (Mol Cancer Ther; 1 0(8); 1470-80, May 27, 2011).
Scholler, Nathalie et al., "Soluble member(s) of the mesothelin/ megakaryocyte potentiating factor family are detectable in sera from patients with ovarian carcinoma", Proc. Natl. Acad, Sci. USA, vol. 96, pp. 11531-11536, Sep. 1999.
Tan et al (FEBS Letters 585 (2011) 2229-2234, and supplemental Figures 1-3).
Uddalak Bharadwaj et al., "Mesothelin-Induced Pancreatic Cancer Cell Proliferation Involves Alteration of Cyclin E via Activation of Stat3", Mol Cancer Res. Nov. 2008; 6(11 ); 1755-1765.
Wang, Tegexibaiyin et al., "Suppression of cell death by the secretory form of N-terminal ERC/Mesothelin", Int' Journal of Molecular Medicine 26: 185-191 (2010).
Wong et al (Ciin Cancer Res 2008;14:2588-2592).
Wu, Xiaohua et al., "Serum Soluble Mesothelin-related peptide (SMRP): a potential diagnostic and monitoring marker for epithelial ovarian cancer", Gynecologic Oncology, Arch Gynecol Obstet 289: 1309-1314 (2014).
Zhanat E. Muminova et a., "Characterization of human mesothelin transcripts in ovarian and pancreatic cancer", BMC Cancer 2004, 4:19; May 12, 2004.
Zhao et al (Childs Nerv Syst (2009) 25:13-20).

MIA-V + - -
MIA-MSLN-miR-Ctrl - + -
MIA-MSLN-miR-198 - - +

ASPC1-miR-Ctrl + -
ASPC1-miR-198 - +

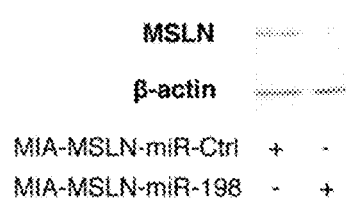
Fig. 4A
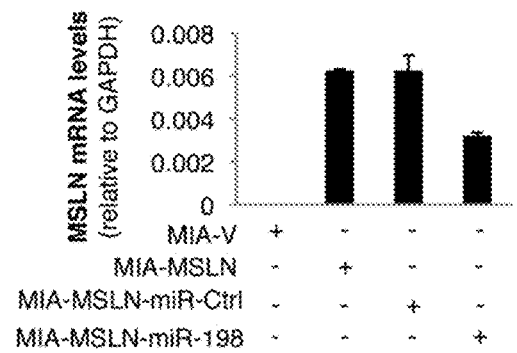
Fig. 4B
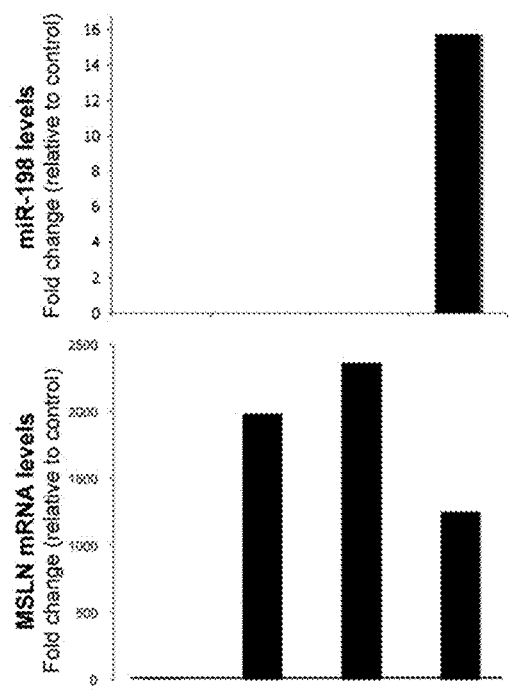
Fig. 4C

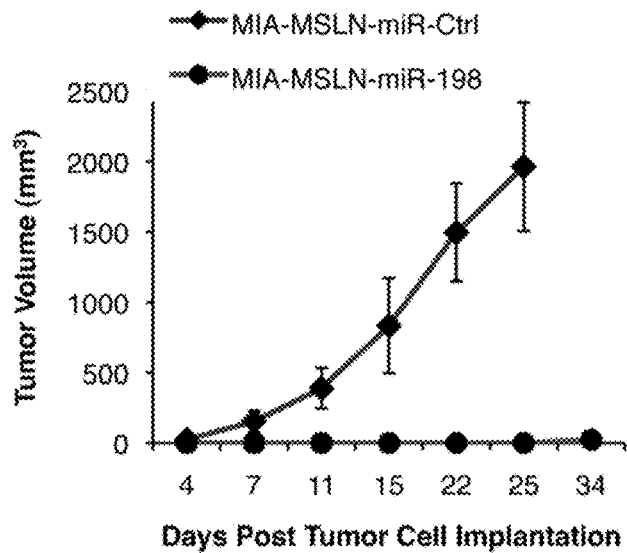
Fig. 7A
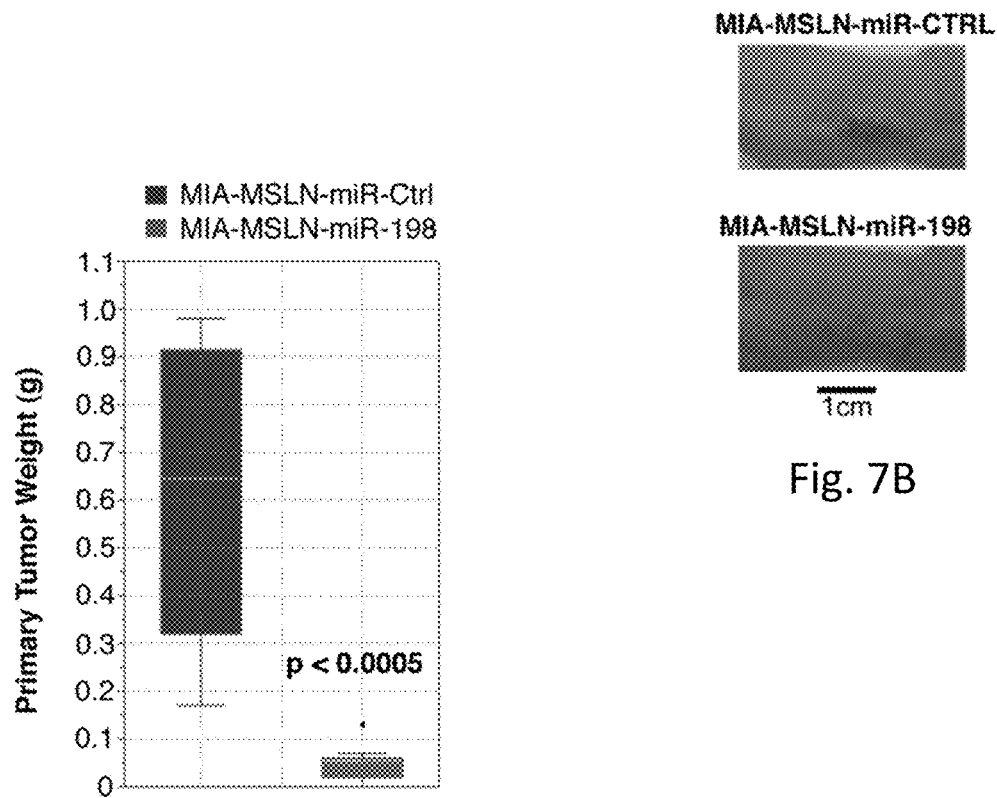
Fig. 7B
Fig. 7C

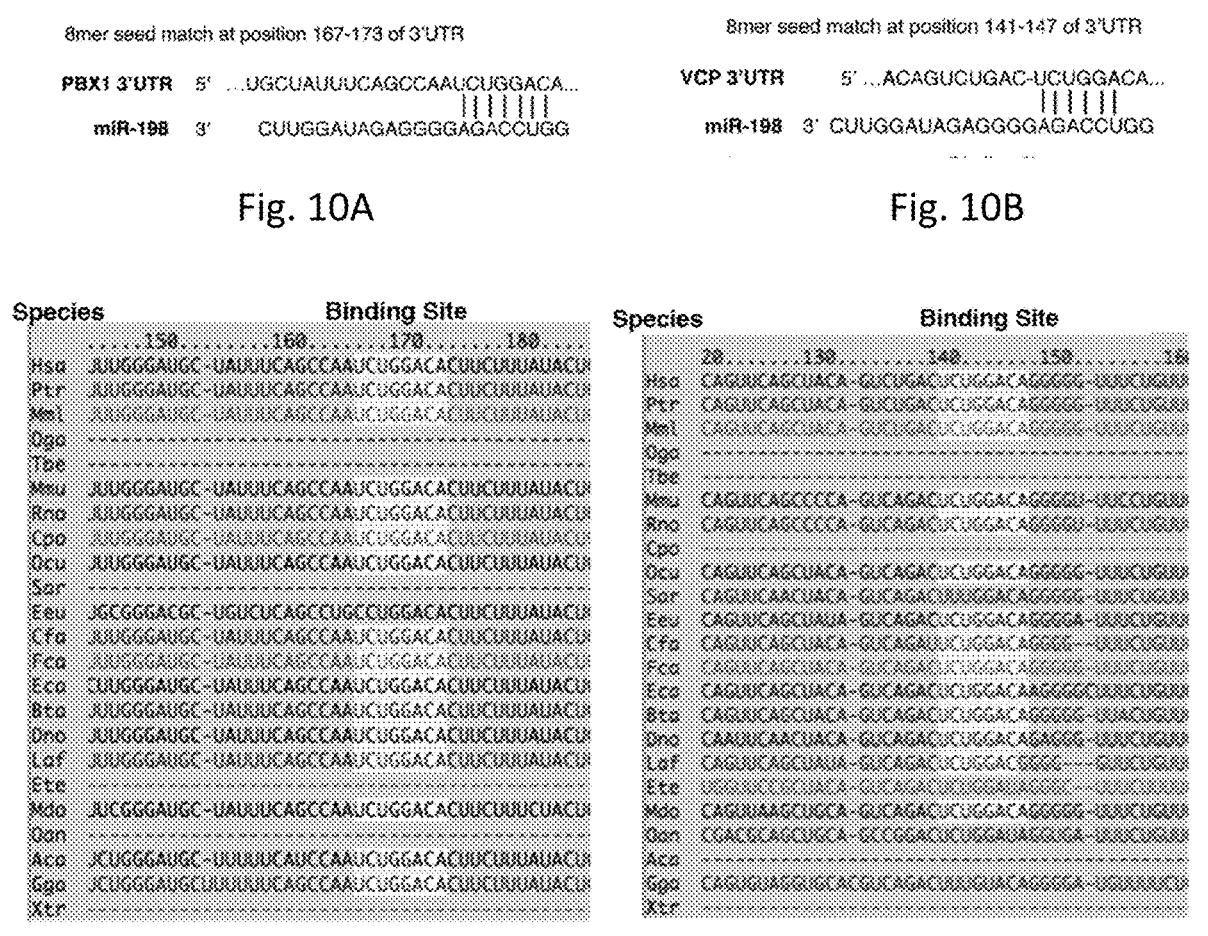

8mer seed match at position 167-173 of 3'UTR

PBX1 3'UTR 5' ...UGCUAUUUCAGCCAAUCUGGACA...
                            |||||||
miR-198    3'  CUUGGAUAGAGGGGAGACCUGG

Fig. 10A

8mer seed match at position 141-147 of 3'UTR

VCP 3'UTR 5' ...ACAGUCUGAC-UCUGGACA...
                          |||||||
miR-198    3'  CUUGGAUAGAGGGGAGACCUGG

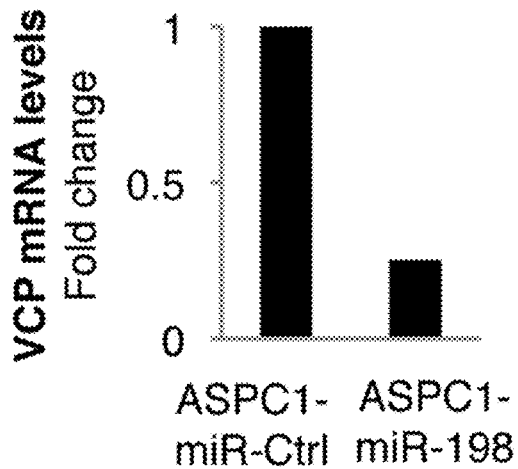

Fig. 10J

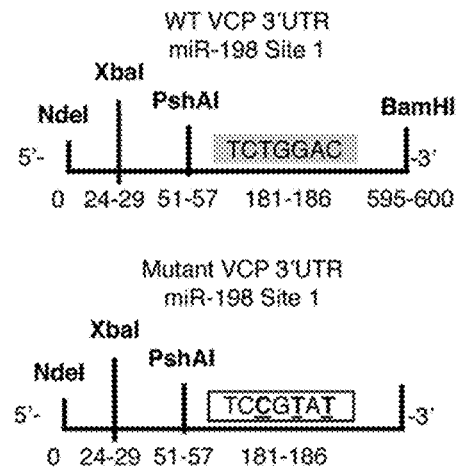

Fig. 10K

| PBX-1 3'UTR WT MiR-198 binding site construct | 5'-CTTCATCAGTGACCTCCCCTACAGAAGGCCCTGGCAGTGTTCACTCTGATACC
TCCAACTGATCTCCCAGCAATCGCATCCCGGCTGACCCTGTGCCCCAGTTGGGG
CAGGGGCAGGAGGGAGGGTTTCTCTCCCAACGCTGAAGCGGTCAGACTGGAGG
TCGAAGCAATCAGCAAACACAATAAGAGTCTCCTTCTCTTCTCTTCTTTGGGATGC
TATTTCAGCCAATCTGGACACTTCTTTATACTCTCTTCCCTTTTTTTTCTGGGTAGA
AGCCACCCTTCCCTGCCTCCAGCTGTCAGCCTGGTTTTCGTCATCTTCCCTGCCC
CTGTGCCTCTGTCCTAGACTCCCGGGGTCCCCGCCCTCTCTCATATCACTGAAGG
ATATTTTCAACAATTAGAGGAATTTAAAGAGGAAAAAAATTACAAAGAAAATAATAA
AAGTGTTTGTACGTTTTCATGCTGGTGGTTTGAGGAGCCAAATTTACCTCA-3' |
|---|---|
| PBX-1 3'UTR Point Mutant MiR-198 binding site construct | 5'-CTTCATCAGTGACCTCCCCTACAGAAGGCCCTGGCAGTGTTCACTCTGATACC
TCCAACTGATCTCCCAGCAATCGCATCCCGGCTGACCCTGTGCCCCAGTTGGGG
CAGGGGCAGGAGGGAGGGTTTCTCTCCCAACGCTGAAGCGGTCAGACTGGAGG
TCGAAGCAATCAGCAAACACAATAAGAGTCTCCTTCTCTTCTCTTCTTTGGGATGC
TATTTCAGCCAAAAGCTTCACTTCTTTATACTCTCTTCCCTTTTTTTTCTGGGTAGA
AGCCACCCTTCCCTGCCTCCAGCTGTCAGCCTGGTTTTCGTCATCTTCCCTGCCC
CTGTGCCTCTGTCCTAGACTCCCGGGGTCCCCGCCCTCTCTCATATCACTGAAGG
ATATTTTCAACAATTAGAGGAATTTAAAGAGGAAAAAAATTACAAAGAAAATAATAA
AAGTGTTTGTACGTTTTCATGCTGGTGGTTTGAGGAGCCAAATTTACCTCA-3' |
| PBX-1 3'UTR Deletion Mutant MiR-198 binding site construct | 5'-CTTCATCAGTGACCTCCCCTACAGAAGGCCCTGGCAGTGTTCACTCTGATACC
TCCAACTGATCTCCCAGCAATCGCATCCCGGCTGACCCTGTGCCCCAGTTGGGG
CAGGGGCAGGAGGGAGGGTTTCTCTCCCAACGCTGAAGCGGTCAGACTGGAGG
TCGAAGCAATCAGCAAACACAATAAGAGTCTCCTTCTCTTCTCTTCTTTGGGATGC
TATTTCAGCCAA        CTTCTTTATACTCTCTTCCCTTTTTTTTCTGGGT
AGAAGCCACCCTTCCCTGCCTCCAGCTGTCAGCCTGGTTTTCGTCATCTTCCCTGC
CCTGTGCCTCTGTCCTAGACTCCCGGGGTCCCCGCCCTCTCTCATATCACTGAAG
GATATTTTCAACAATTAGAGGAATTTAAAGAGGAAAAAAATTACAAAGAAAATAATAA
AAGTGTTTGTACGTTTTCATGCTGGTGGTTTGAGGAGCCAAATTTACCTCA-3' |

| Site 1 | miR-198 binding site 1 at position 1267-1288 of MSLN CDS<br>MSLN CDS    5'-GGCCTG--CTGCCCGTGCTGGGCC...<br>                       ｜｜｜｜｜｜  ｜｜｜｜｜｜｜ ｜｜｜｜｜｜<br>miR-198     3'- CUUGGAUAGAGGGGA----GACCUGG |
|---|---|
| Site 2 | miR-198 binding site 2 at position 916-937 of MSLN CDS<br>MSLN CDS    5'-TCTGTGATCCAGCAC--CTGGGCT...<br>                       ｜｜｜｜｜｜｜｜｜｜｜｜   ｜｜｜｜｜｜｜<br>miR-198     3'-CUUGGAUAGAGGG----GAGACCUGG |
| Site 3 | miR-198 binding site 3 at position 511-532 of MSLN CDS<br>MSLN CDS    5'- ACGCC----CTCCCA-TTGGACC...<br>                       ｜｜｜｜    ｜｜｜｜｜｜ ｜｜｜｜｜｜｜<br>miR-198     3'-CUUGGAUAGAGGGGAGACCUGG |

Fig. 13B

| Site 1 | WT Seq | TCT | GTG | ATC | CAG | CAC | CTG | GGC | TAC |
|---|---|---|---|---|---|---|---|---|---|
| | AA Translation | SER | LEU | ILE | GLN | HIS | LEU | GLY | TYR |
| | Mut Seq | | | | | | TTA | GGA | |

| Site 2 | WT Seq | GGC | CTG | CTG | CCC | GTG | CTG | GGC | CAG |
|---|---|---|---|---|---|---|---|---|---|
| | AA Translation | GLY | LEU | LEU | PRO | VAL | LEU | GLY | GLN |
| | Mut Seq | | | | | | TTA | GGA | |

| Site 3 | WT Seq | CTG | GAC | GCC | CTC | CCA | TTG | GAC | CTG |
|---|---|---|---|---|---|---|---|---|---|
| | AA Translation | LEU | ASP | ALA | LEU | PRO | LEU | ASP | LEU |
| | Mut Seq | | | | | | CTA | GAT | |

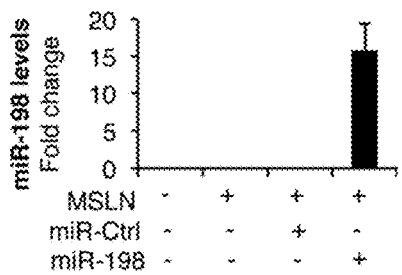

Fig. 13C

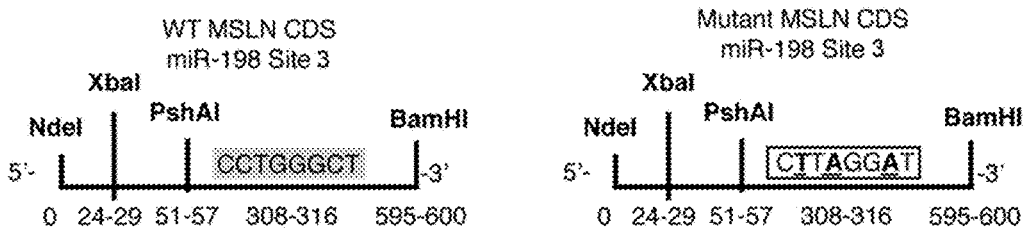

Fig. 13D

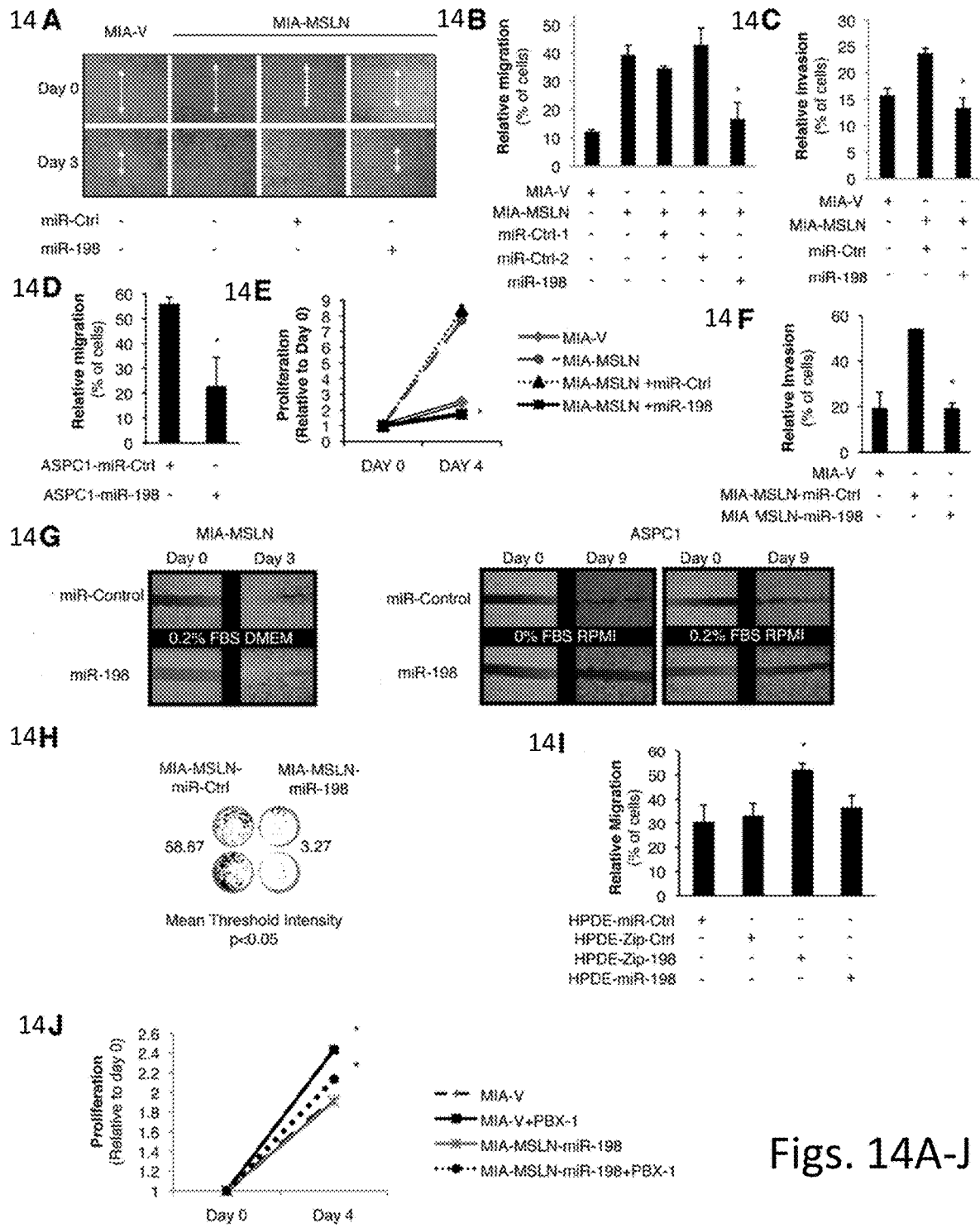
Figs. 14A-J

MICRORNA-198 AS A TUMOR SUPPRESSOR IN OVARIAN CANCER

CROSS-REFERENCE TO RELATED APPLICATIONS

This application is a continuation of U.S. patent application Ser. No. 16/299,986 filed Mar. 12, 2019; which is a continuation of U.S. patent application Ser. No. 15/955,451 filed Apr. 17, 2018; which is a continuation of U.S. patent application Ser. No. 15/372,759 filed Dec. 8, 2016; which is a continuation of U.S. patent application Ser. No. 14/615,168 filed Feb. 5, 2015, issued as U.S. Pat. No. 9,546,365 on Jan. 17, 2017; which is a continuation of U.S. patent application Ser. No. 13/567,852 filed Aug. 6, 2012, issued as U.S. Pat. No. 8,987,224 on Mar. 24, 2015; which claims the benefit of priority to U.S. Provisional Patent Application No. 61/515,416 filed on Aug. 5, 2011, all of which are incorporated herein by reference in their entirety.

STATEMENT REGARDING FEDERALLY SPONSORED RESEARCH OR DEVELOPMENT

This invention was made with government support under Grant No. CA140828 awarded by the National Institutes of Health. The government has certain rights in the invention.

INCORPORATION OF SEQUENCE LISTING

The sequence listing that is contained in the file named "Sequence_Listing_BAYM_P0057US_C5.txt", which is 25.8 KB (as measured in Microsoft Windows) and was created on Apr. 21, 2021, is filed herewith by electronic submission and is incorporated by reference herein.

TECHNICAL FIELD

The field of the invention regards at least cell biology, molecular biology, and medicine. In specific cases, the field of the invention includes pancreatic cancer.

BACKGROUND OF THE INVENTION

Pancreatic cancer (PC) is the fourth leading cause of cancer-related deaths in North America, with a <6% five-year survival prognosis (Jemal et al., 2010; Li et al., 2008; Zhang et al., 2010). Understanding the mechanisms that give rise to PC pathogenesis and identifying prognostic marker signatures are critical for the development of new diagnostic and therapeutic strategies. The complex biological functions that give rise to cancer pathogenesis can rarely be attributed to individual molecules but rather arise from key interactions among various heterogeneous components interacting in modular regulatory networks, which result in a specific disease signature with far-reaching clinical effects (Bonnet et al., 2010; Hartwell et al., 1999). Described below are a multitude of individual molecules whose interactions were previously unknown, but are elucidate in the Detailed Summary.

Mesothelin (MSLN) is a cell surface glycoprotein over-expressed in ~90% of human pancreatic adenocarcinomas (Argani et al., 2001; Bharadwaj et al., 2008; Li et al., 2008; Muminova et al., 2004). It was previously reported that MSLN overexpression leads to increased PC cell proliferation, invasion, and migration in vitro and increased tumor growth in vivo (Li et al., 2008). Yet little is known about the mechanisms through which MSLN overexpression gives rise to this aggressive phenotype. Further, several studies have identified roles for microRNAs (miRNAs) in PC pathogenesis. MiRNAs are a group of small, non-coding RNA molecules that act as posttranscriptional regulators of messenger RNA activity and are frequently dysregulated in cancers (Garofalo et al., 2009). It has been postulated that a single miRNA can regulate several links of an entire functional network, and its dysregulation can therefore give rise to a complex disease phenotype (Wang et al., 2011). It was previously reported that MSLN constitutively activates NF-κB and promotes cell survival (Bharadwaj et al., 2011a; Bharadwaj et al., 2011b). OCT-2 is a bi-functional TF that can exert both activating and repressing functions in a context-dependent manner (Friedl and Matthias, 1995; Liu et al., 1996). Its expression was previously thought primarily restricted to B-cells. All tumor cell lines of the B-cell lineage express OCT-2, including Hodgkin's disease cells (Bargou et al., 1996) and non-Hodgkin's lymphoma (Pileri et al., 2003). ZEB1 is a crucial epithelial-to-mesenchymal transition (EMT) activator in human colorectal and breast cancer (Burk et al), and has been linked to increased EMT and chemoresistance in pancreatic cancers (Wang et al., 2009). ZEB1 also directly suppresses transcription of and is involved in a reciprocal regulatory loop with miRNAs in the miR-200 family (Burk et al, 2008). PBX-1 was initially identified as a participant in pre-B-cell acute lymphoblastic leukemia (Asahara et al., 1999; Dutta et al., 2001), has been associated with progression of melanoma, (Shiraishi et al., 2007) and is an inducer of the gene for VCP, a ubiquitously expressed protein involved in cell survival (Wang et al., 2004). VCP is associated with cancer growth and is a prognostic marker for PC metastasis (Asai et al., 2002; Yamamoto et al., 2004c; Yamamoto et al., 2004d; Yamamoto et al., 2004e).

The approach of studying a single molecule in an effort to identify effective anti-tumor targets is quickly being replaced by a system-wide approach to dissect the complex interactions between genes, RNA, and proteins in regulating tumor progression. Here, a unique perspective on the interplay between several factors in a functional network is presented, which approaches the study of the effects of a single, central microRNA from a network biology framework. This disclosure uncovers a novel functional interactome in PC, dissects the mechanisms through which a central miRNA can alter the molecular makeup of pancreatic tumors, and identifies a pattern of expression that correlates directly with patient prognosis and survival. Examined are the expression, mechanisms of regulation, and resulting functions of this regulatory interactome, linking together the influence of various seemingly heterogeneous tumorigenic factors as a modular unit in PC pathogenesis, with significant clinical implications. In addition clinically relevant treatments for PC are disclosed, as is a biomarker signature which predicts treatment response and prognosis of patients with PC.

BRIEF SUMMARY OF THE INVENTION

The present invention is directed to a method of treating cancer. Specifically, the method includes increasing the levels of miRNA-198 in cancer cells in which high levels of MSLN, OCT-2, PBX-1, VCP, and/or ZEB1 are expressed.

A general embodiment of the disclosure is a method of treating cancer in an individual, comprising the step of delivering to the individual an effective amount of an agent that increases the level of microRNA-198 molecules in cancer cells of the individual. To increase the levels, the agent may upregulate microRNA-198 and/or may directly deliver miRNA-198 to the cancer cell. The agent may comprise microRNA-198, a microRNA-198 mimic, and/or a modified microRNA-198. The cancer may be a cancer in which MSLN, OCT-2, PBX-1, VCP, and/or ZEB1 are upregulated and/or expressed, such as pancreatic cancer, ovarian cancer, or liver cancer.

The composition may be administered through a variety of means. For example, the composition is administered by a viral vector, a non-viral vector, a liposome, a microcarrier, nanocarrier, or a combination thereof. The composition may also be administered locally, systemically, or a combination thereof. In an embodiment of the disclosure, the composition is delivered in a single or multiple cycles of treatment.

In embodiments of the invention, delivering an effective amount of an agent that increases the level of microRNA-198 in cancer cells causes an improvement in the cancer by inhibiting migration, invasion, proliferation, tumor growth, metastatic potential, tumorigenesis or a combination thereof of the cancer and thereby increasing survival and prognosis of patients. The individual with cancer may be further provided with one or more additional anti-cancer therapies, such as chemotherapy, radiotherapy, immunotherapy, gene therapy, surgery, non-microRNA-198 microRNA, siRNA or a combination thereof. The chemotherapeutic agent effective against cancer may comprise gemcitabine, 5-fluorouracil, cisplatin, irinotecan, paclitaxel, capecitabine, oxaliplatin, streptozocin, or a combination thereof. The microRNA-198 molecule level may be levels of modified microRNA-198, unmodified microRNA-198, microRNA-198 mimics, or a mixture thereof. The agent may comprise an oligonucleotide that is 90%, 95% or 100% similar to SEQ ID NO: 1. Additionally, the method may further comprise the step of determining the levels of MSLN, OCT-2, PBX-1, VCP, and/or ZEB1 in the cancer of the individual.

The method of claim 1, wherein the miRNA-198 comprises SEQ ID NO:1.

Another general embodiment of the disclosure is a method of inhibiting proliferation and metastatic potential of at least one cancer cell in an individual, comprising delivering to the individual an effective amount of a composition which comprises an agent that increases the levels of microRNA-198 molecules in a cancer cell. In one embodiment, the agent upregulates microRNA-198. The composition may be administered by a viral vector, a non-viral vector, a liposome, a viral vector, a microcarrier or a combination thereof. The composition may be administered locally, systemically, or a combination thereof. The agent may comprise microRNA-198, for example, SEQ ID NO:1, or the agent may comprise a modified microRNA-198 oligonucleotide or a microRNA-198 mimic. The agent may comprise an oligonucleotide that is 90%, 95% or 100% similar to SEQ ID NO: 1. The individual may be further provided one or more additional anti-cancer therapies, such as chemotherapy, radiotherapy, immunotherapy, gene therapy, surgery, non-microRNA-198 microRNA, siRNA, or a combination thereof. In an embodiment, the agent is delivered in multiple cycles of treatment. The cancer may be a cancer in which MSLN, OCT-2, PBX-1, VCP, and/or ZEB1 are upregulated and/or expressed, such as pancreatic cancer, ovarian cancer, or liver cancer.

Another general embodiment of the invention is a kit for cancer treatment, said kit housed in a suitable container and comprising a first anti-cancer agent that increases the levels of active microRNA-198 molecules in a cell. In an embodiment of the disclosure, the first anti-cancer agent upregulates microRNA-198 in a cell, such as a cancer cell. The first agent may comprise microRNA-198, a microRNA-198 mimic, a modified microRNA-198, or a combination thereof. The agent may comprise microRNA-198, for example, SEQ ID NO:1. The agent may comprise an oligonucleotide that is 90%, 95% or 100% similar to SEQ ID NO: 1. The agent may further comprise a vector, a microcarrier, or a liposome. The kit may further comprise one or more additional anti-cancer agents, such as a chemotherapeutic agent which may be effective against cancer. In an embodiment of the disclosure, the chemotherapeutic agent effective against cancer comprises gemcitabine, 5-fluorouracil, cisplatin, irinotecan, paclitaxel, capecitabine, oxaliplatin, streptozocin, or a combination thereof. The one or more additional anti-cancer agent may comprises one or more radioisotopes. The cancer may be a cancer in which MSLN, OCT-2, PBX-1, VCP, and/or ZEB1 are upregulated and/or expressed, such as pancreatic cancer, ovarian cancer, or liver cancer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

FIG. 1A is the profiling of 95 cancer-associated miRNAs in MIA-V vs MIA-MSLN cells. FIG. 1B is a graph of $\log_{10}$ miR-198 levels for 37 patients. FIG. 1C is a graph of the percent patient survival after the time of diagnosis for patients in the miR-198 low and miR-198 high groups. FIG. 1D is a linear regression analysis correlating miR-198 expression to mRNA levels of FSTL1, OCT-2, MSLN, PBX-1, and VCP in patient tumor tissues. FIGS. 1E-1F are five-order Venn diagram representing the complex interactome between the factors in the network. The percent of patients in which the specific factors are upregulated (or downregulated in the case of miR-198) either individually or for all possible combinations is shown for all patients in FIG. 1E, for patients in the miR-198-Low group alone in FIG. 1F, or for patients in the miR-198-High group alone in FIG. 1G.

FIG. 2A is a graph of miR-198 levels fold change over a control in HPDE-V and HPDE-MSLN cells. FIG. 2B is the miR-198 expression fold change over and demonstrates that silencing MSLN restores miR-198 expression. FIG. 2C is a graph illustrating miR-198 expression and MSLN mRNA levels in a variety of different types of cells. Fold change was calculated relative to PC cell with lowest expression of each factor. FIG. 2D shows a linear regression analysis of FSTL1 expression versus miR-198 levels in a panel of PC cells showing a significant positive correlation ($p<0.001$, $R_{2=0.87}$). FIG. 2E is a graph which shows FSTL1 mRNA levels and demonstrates FSTL1 expression is decreased in MIA-PaCa2 cells in accordance with miR-198 expression following forced MSLN expression. FIG. 2F illustrates that wedelolactone treatment restores miR-198 expression in MIA-MSLN cells to pre-MSLN levels and FIG. 2G illustrates wedelolactone treatment blocks OCT-2 induction in MIA-MSLN cells. FIG. 2H illustrates ShRNA-mediated silencing of OCT-2 rescues miR-198 expression in MIA-MSLN cells.

FIG. 3A demonstrates MSLN protein expression correlates positively with PBX-1 expression, and both correlate negatively with miR-198 ($p<0.005$), in a PC cell line panel. FIG. 3B demonstrates increased OCT-2 protein expression is accompanied by a strong induction in PBX-1. FIG. 3C demonstrates VCP expression, along with downregulation in miR-198 expression. FIG. 3D demonstrates PBX-1 expression increases following MSLN overexpression in MIA-PaCa2 cells, and is restored following miR-198 overexpression. FIG. 3E demonstrates VCP expression in AsPC1 cells is downregulated ~50 fold following miR-198 overexpression. FIG. 3F demonstrates Wedelolactone results in a block in PBX-1 expression. FIG. 3G is a dual-luciferase reporter assay which shows a ~65% reduction in luciferase expression of a PBX-1 3'UTR or in FIG. 3H a ~70% reduction in luciferase expression of a VCP 3'UTR luciferase reporter following miR-198 overexpression, which is abolished when the miR-198 target site is mutated and/or deleted. Expressed as firefly/*Renilla* ratio.

FIGS. 4A-4E illustrate miR-198 reciprocally regulates MSLN expression by binding to target sites within the MSLN CDS. FIG. 4A demonstrates MiR-198 overexpression blocks MSLN at the protein level. FIG. 4B demonstrates MSLN mRNA levels are partially downregulated following miR-198 overexpression. FIG. 4C demonstrates MiR-198 reduces expression of a co-transfected MSLN expression plasmid at the protein level, with a partial decrease in mRNA expression. FIG. 4D illustrates site-directed mutagenesis of each of the three miR-198 binding sites within the MSLN coding region separately or in combination leads to differential restoration MSLN protein expression in the presence of miR-198. FIG. 4E demonstrates MiR-198 decreases luciferase expression in WT MSLN CDS constructs for sites 2 and 3 ($p<0.05$) but not significantly for site 1. Mutating the miR-198 seed region for sites 2 or 3 restores luciferase expression. Expressed as firefly/*Renilla* ratio. Mean±SD.

FIG. 5A demonstrates MSLN overexpression increases MIA-PaCa2 cell migration, and this effect is reversed following miR-198 overexpression ($p<0.05$). FIG. 5B demonstrates average proliferation ($p<0.05$) and FIG. 5C demonstrates invasion of AsPC1 cells is decreased ~50% following miR-198 overexpression ($p<0.05$). FIG. 5D illustrates wound healing assay shows that miR-198 decreases the migratory potential of MIA-MSLN cells. FIG. 5E demonstrates MiR-198 overexpression reduces the ability of MIA-MSLN cells for anchorage independent growth in soft agar. FIG. 5F illustrates the use of an antisense inhibitor of miR-198 leads to significantly increased proliferative ($p<0.05$) and FIG. 5G illustrates migratory potential of MIA-V cells ($p<0.05$). FIG. 5H demonstrates PBX-1 silencing has a significant ($p<0.05$) but modest effect on proliferation. FIG. 5I demonstrates PBX-1 overexpression in MIA-V or MIA-MSLN-miR-198 cells results in an increase in migration resembling that observed in MIA-MSLN cells ($p<0.05$). PBX-1 silencing reduces the MSLN-mediated increase in migration ($p<0.05$). Mean±SD.

FIG. 6A illustrates a TUNEL assay which shows a significant increase in apoptosis after TNF-α treatment in two high MSLN cells following overexpression of miR-198. FIG. 6B demonstrates a TUNEL assay which shows a significant decrease in apoptosis in MIA-V cells (high miR-198 cells) down to MIA-MSLN cell levels following blocking of miR-198 (MIA-V-Zip-198). FIG. 6C demonstrates overexpression of miR-198 in MIA-MSLN cells results in caspase 3 cleavage.

FIGS. 7A-7F illustrate miR-198 overexpression modulates expression of regulatory network and reduces tumor growth and metastatic spread in vivo. FIG. 7A demonstrates nude mice injected s.c. with MIA-MSLN-miR-Ctrl cells started to develop tumors by 7 days post injection. The mice were sacrificed at 25 days post injection when their tumors reached an average volume of 2000 mm$^3$. Only 3 of 9 mice injected with MIA-MSLN-miR-198 cells developed tumors, with an average volume of only 36 mm$^3$ by day 45 post injection. FIG. 7B are representative images for each s.c. mouse group, 9 mice per group. FIG. 7C shows nude mice injected orthotopically with MIA-MSLN-miR-Ctrl cells developed primary tumors after 4 weeks that were approximately 10-fold larger (by weight) than tumors primary tumors developed by mice injected with MIA-MSLN-miR-198 cells, and included 8 mice per group. FIG. 7D shows primary tumors resected from each mouse in both groups. FIG. 7E shows GFP expression in the tumor cells allows for visualization of tumor spread. FIG. 7F shows real-time RT-PCR was used to confirm RNA levels of all the factors in the regulatory network. Mean±SD, n=4, * $p<0.05$.

FIG. 9A represents real-time RT-PCR, which shows the mRNA levels of all the factors in the proposed network (MSLN, OCT-2, PBX-1, VCP, and FSTL1, respectively), segregated into two groups based on miR-198 levels as described in FIG. 1. FIG. 9B is a linear regression analyses which depicts the correlations between each factor and its counterparts. Separate regression analyses were performed for MSLN, OCT-2, PBX-1, VCP, and FSTL1, respectively.

FIGS. 10A-10L illustrate PBX-1 and VCP are predicted targets for miR-198. FIG. 10A demonstrates PBX-1 has a predicted 8mer binding site for miR-198 in its 3'UTR. FIG. 10B demonstrates VCP is also a predicted target for miR-198, with a predicted 8mer binding site for miR-198 in its 3'UTR. FIG. 10C demonstrates the predicted binding site for miR-198 in the 3'UTR of PBX-1 and FIG. 10D demonstrates VCP is evolutionarily conserved in a majority of species examined using TargetScan software. FIG. 10E is a graph of real-time RT-PCR for MSLN and PBX-1 in a panel of PC cell lines, which shows that PBX-1 increases as MSLN expression increases. Fold change was calculated relative to PC cell with lowest expression. Mean shown. FIG. 10F demonstrates PBX-1 levels increase as miR-198 levels decrease in a panel of PC cell lines. Fold change was calculated relative to PC cell with lowest expression. Mean shown. FIG. 10G demonstrates Mir-198 downregulates PBX-1 mRNA in MIA-MSLN cells and FIG. 10H in ASPC1 cells. FIG. 10I demonstrates MIA-MSLN cells show a ~2-fold increase in VCP mRNA levels over MIA-V cells. MiR-198 overexpression reduces VCP down to MIA-V cell levels. FIG. 10J demonstrates VCP mRNA levels are downregulated ~5 fold in ASPC1 cells following miR-198 overexpression. FIG. 10K is a schematic representation of the construction scheme for the miR-198 binding site within the VCP 3'UTR. The restriction sites including XbaI and BamH1 and additional sites used for insert confirmation are shown, along with the 3-nucleotide mutation incorporated into the miR-198 seed region. FIG. 10L are nucleotide sequences for the first ~500 bases of the PBX-1 3'UTR that were cloned into the PSGG-3'UTR vector for luciferase assays, including the WT, point mutation, and deletion mutations in the miR-198 binding site seed regions (bold and highlighted).

FIG. 11A illustrates OCT-2 expression shown in MIA-V and MIA-MSLN cells. FIG. 11B shows OCT-2 expression is blocked following Wedelolactone treatment of AsPC1 cells.

—FIG. 12A: miR-198 overexpressing MIA-MSLN cells, FIG. 12B: miR-198 overexpressing ASPC1 cells, FIG. 12C: miR-198 overexpressing and/or Zip-198 blocked MIA-V cells, and FIG. 12D: miR-198 overexpressing or FIG. 12E: Zip-198 blocked HPDE stable cell lines.

FIGS. 13A-13D are the construct details for miR-198 target analysis of MSLN CDS. FIG. 13A illustrates miR-198 has three target sites in the MSLN gene, as predicted by RNA22 software. FIG. 13B shows three nucleotide substitutions were introduced via site-directed mutagenesis into each of the 3 predicted binding sites for miR-198 in the MSLN coding region. The mutations were selected so as to not alter the amino acid sequence of the MSLN protein to allow for proper expression and detection while still preventing miR-198 directed targeting. Seed region are shown in bold. FIG. 13C shows miR-198 levels shown in COS-7 cells following transfection of miR-198 expression plasmid. FIG. 13D is a schematic representation of the construction scheme for miR-198 binding site 3 within the MSLN coding region. The restriction sites including XbaI and BamH1 and additional sites used for insert confirmation are shown, along with the 3-nucleotide mutations incorporated into the miR-198 seed region. The same scheme was used in all six constructs.

FIGS. 14A-14J illustrate additional evidence of miR-198 tumorigenic functions in PC cells in vitro. FIG. 14A is a monolayer wound-healing assay which shows a reduction in migration and proliferation back to MIA-V control levels following miR-198 precursor transfection compared to a scrambled miRNA control. Mean±SD. FIG. 14B demonstrates invasion is reduced by 24% 36 h after miR-198 precursor transfection ($p<0.05$). Mean±SD. FIG. 14C demonstrates migration is reduced by 44% 36 h after transient miR-198 transfection ($p<0.05$). Mean±SD. FIG. 14D shows MiR-198 overexpression decreases migration of AsPC1 ($p<0.05$) cells by >50%. Mean±SD. FIG. 14E demonstrates MiR-198 overexpression decreases proliferation (results shown as mean of five wells. Error bars omitted for clarity) and FIG. 14F demonstrates invasion (across a matrigel matrix) of MIA-MSLN cells ($p<0.05$) FIG. 14G are monolayer wound healing assays which were performed in different serum conditions to demonstrate reduced migration and proliferation of both MIA-MSLN and AsPC1 cells following miR-198 overexpression. FIG. 14H demonstrates blocking miR-198 in HPDE cells results in increased migration after 72 h ($p<0.05$). Further overexpression of miR-198 in these cells did not seem to have an effect. Mean±SD. FIG. 14I shows that blocking of miR-198 in HPDE cells led to an increase in migration. FIG. 14J demonstrates modulation of PBX-1 in MIA-PaCa2 cells increases proliferation.

FIG. 15A shows ZEB1 expression increases following MSLN overexpression. FIG. 15B shows ShRNAs against MSLN reduce ZEB1 expression at the mRNA and FIG. 15C. are protein levels in MIA-MSLN cells. FIG. 15D illustrates Wedelolactone treatment blocks ZEB1 expression in MIA-MSLN cells. FIG. 15E shows ZEB1 is expressed in a majority of cell lines with high MSLN/low miR-198 expression, while it is not expressed in miR-198 high Capan-1 or HPDE cells. Line depicts separation between non-contiguous lanes. FIG. 15F. shows transient transfection of shRNAs against ZEB1 reduces ZEB1 protein expression and restores miR-198 expression in MIA-MSLN cells. Figure was modified to show samples run on the same gel but in non-contiguous lanes, as depicted by separation. FIG. 15G demonstrates ZEB1 transfection in MIA-PaCa2 cells reduces miR-198 expression after 48 h.

DETAILED DESCRIPTION OF THE INVENTION

Figure 1A:
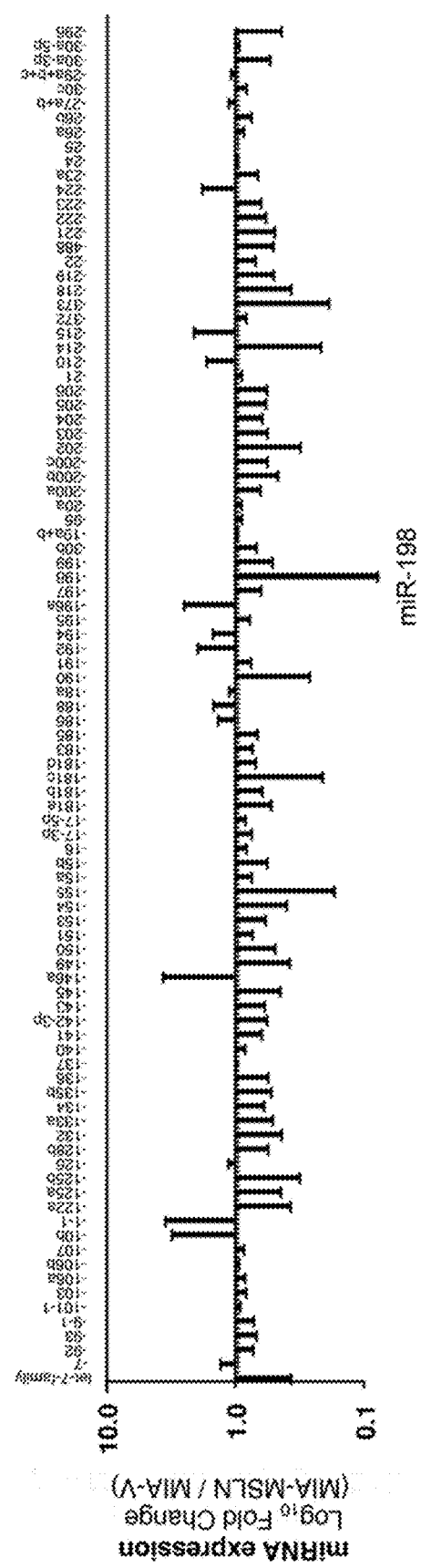
FIGS. 1A-1G illustrate that the interactome of tumorigenic factors interconnected through miR-198 serve as a prognostic indicator of PC.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "synergistic" or "synergistically" as used herein refers to the addition of two reactants that may or may not react in the same pathway with each other, from which the resulting product of the reaction proceeds to a further extent than one of skill in the art would predict. In a specific embodiment, two compounds act synergistically when the result achieved upon using them in combination is greater than the sum of the results of the compounds when used separately.

The phrase "effective amount" as used herein means that amount of a compound, material, or composition comprising a compound of the present invention that is effective for producing some desired effect, e.g., halting the growth of, reducing the size of, and/or causing apoptosis in a cancer cell. In one embodiment, the effective amount is enough to reduce or eliminate at least one cancer cell. One of skill in the art recognizes that an amount may be considered effective even if the cancer cell is not totally eradicated but decreased partially. For example, the spread of the cancer may be halted or reduced, a side effect from the cancer may be partially reduced or completed eliminated, and so forth. The effective amount may also be a therapeutically effective amount.

The terms "inhibit," "inhibitory," or "inhibitor" as used herein refers to one or more molecules that interfere at least in part with the growth or activity of the molecule or cell it inhibits. The inhibition of a cancer cell may be the inhibition of growth of at least one cancer cell.

As used herein, "treat" and all its forms and tenses (including, for example, treat, treating, treated, and treatment) refer to both therapeutic treatment and prophylactic or preventative treatment. Those in need thereof of treatment include those already with a pathological condition of the invention (including, for example, a cancer) as well as those in which a pathological condition of the invention is to be prevented. In certain embodiments, the terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the individual's condition, but may not be a complete cure of the disease. Treating may also comprise treating subjects at risk of developing a disease and/or condition of the invention.

As used herein the term "metastatic" (and all other forms and tenses, including, for example, metastasis, metastasize, etc.) when used alone or in conjunction with cancer refers to the spread of a cancer from one part of the body to another, unless otherwise indicated by the use or context. Typically, a tumor formed by cells that have spread is called a "metastatic tumor" or a "metastasis." The metastatic tumor contains cells that are like those in the original (primary) tumor.

As used herein, an "individual" is an appropriate individual for the method of the present invention. A subject may be a mammal and in specific embodiments is any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, horses, sheep, pigs and chimpanzees. Subjects may also be referred to as "patients" or "subjects".

An embodiment of the disclosure is the identification of a novel network of tumorigenic prognostic factors that plays a critical role in advanced pancreatic cancer (PC) pathogenesis. This interactome is interconnected through a central tumor suppressive microRNA, miR-198, which is able to both directly and indirectly modulate expression of the various members of this network to alter the molecular makeup of pancreatic tumors, with important clinical implications. When this tumor signature network is intact, miR-198 expression is reduced and patient survival is dismal; patients with higher miR-198 present an altered tumor signature network, better prognosis and increased survival. Further, according to the present disclosure, MiR-198 replacement reverses tumorigenicity in vitro and in vivo. This illustrates the therapeutics of attacking a complex heterogeneous network of factors through a central vantage point.

Figure 8:
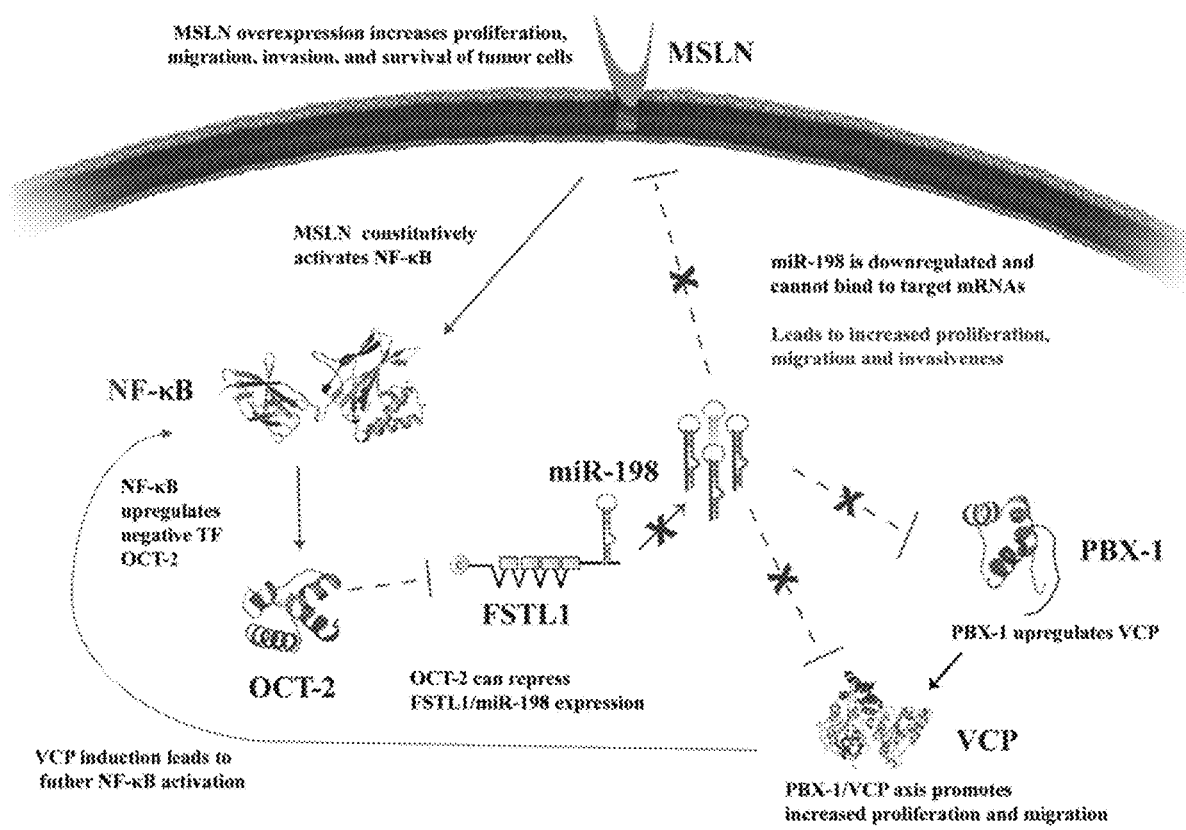
FIG. 8 is a diagram of the network of heterogeneous prognostic factors for pancreatic cancer interconnected through modulation of central tumor-suppressive miR-198.

Another embodiment of the disclosure is miR-198 as a critical prognostic factor for PC patient survival based on its expression in patient tumors. With miR-198 as a central vantage point, a systemic approach was used to identify both novel and well-established PC prognostic factors that could either modulate or be modulated by miR-198. These studies are summarized below, with a in-depth review in the example section. In an effort to study the molecular interactions that lead to MSLN-mediated pathogenesis in PC, the miRNA signature of MSLN-overexpressing vs. MSLN low PC cells was examined. It was found that miR-198 was the most significantly downregulated miRNA among a global dysregulation of miRNAs as a result of MSLN overexpression. Additionally, the MSLN-NF-κB interaction was identified as a key component of the in the regulation of miR-198. Thus, an embodiment of the disclosure is a novel role for MSLN-mediated NF-κB activation as an indirect regulator of miR-198 expression, through the induction of the repressive transcription factor OCT-2 (POU2F2) which was selected based on microarray analysis of MSLN-overexpressing vs. MSLN low PC cells. It is also seen for the first time that OCT-2 is not only expressed in PC cells, but that it plays a role in regulating miR-198, and through this interaction also modulates expression of miR-198 downstream targets. Through indications found in the microarray data, two downstream effectors of miR-198 were identified, Pre-B-cell leukemia homeobox factor 1 (PBX-1), and Valosin-containing protein (VCP). Additionally, the PBX-1/VCP axis plays a key role in PC pathogenesis. Thus, this disclosure includes a unique perspective on the interplay between several factors in a functional network, approaching the study of the effects of a single, central microRNA from a network biology framework. In doing so, a novel functional network was discovered in PC, as well as the mechanisms by which key interactions among tumor suppressive and tumor promoting molecules can alter the molecular makeup of pancreatic tumors, with significant clinical implications. The functional network of prognostic factors in pancreatic cancer by miR-198, illustrated in FIG. 8, contributes to increased tumor cell aggressiveness and decreased patient survival. MiR-198 acts as a tumor suppressor by interfering with this functional network. In an embodiment of the invention, miR-198 replacement therapy extends patient survival by leading to a change in the molecular makeup of aggressive pancreatic tumors.

An embodiment of the invention is the therapeutic value of miR-198 and its influence on the interactions of an array of tumorigenic factors. There was a very clear distinction in the prognostic outcome of patients following resectable surgery. Patients with higher miR-198 levels had a better prognosis, with 80% of them still alive at the 40 month mark. In stark contrast, only 11% of patients with low miR-198 levels survived to this point. The causative role of miR-198 is demonstrated in this increased survival rate by showing that reconstitution of miR-198 significantly reduces tumor growth and metastasis of PC cells in mouse xenografts. In an embodiment of the disclosure, effects of miR-198 are due not to the regulation of a single factor, but rather the modification of the molecular makeup of tumors through a concerted modulation of a novel functional network of prognostic factors, which includes established PC biomarkers and effectors MSLN and NF-κB, as well as factors previously uncharacterized in PC pathogenesis, OCT-2 and the PBX-1/VCP axis.

Within this concerted network, a complex reciprocal regulatory loop was uncovered between MSLN and miR-198 that gives novel insight into the mechanisms of MSLN-mediated PC pathogenesis. It was previously reported that MSLN overexpression leads to constitutive activation of NF-κB, resulting in a positive regulation of cell survival and proliferation of PC cells under serum-reduced and anchorage-independent conditions through NF-κB-mediated IL-6 induction (Bharadwaj et al., 2011a; Bharadwaj et al., 2011b). Here, these findings are extended to show that MSLN-mediated NF-κB activation can result in modulation of miR-198 expression through the induction of the POU domain TF OCT-2.

OCT-2 overexpression has been found in all types of tumors of the B-cell lineage and OCT-2 has been associated with various hematologic malignancies (Bargou et al., 1996; Heckman et al., 2006). Here, OCT-2 was identified as an important factor in PC for the first time. OCT-2 is overexpressed in a majority of PC cell lines and is upregulated in over 80% of patient tumor tissues, and acts as a repressor of the FSTL1/miR-198 promoter which presents a novel role for this protein as a PC prognostic factor and functional target.

Another novel finding is that miR-198 can reciprocally target not just one, but multiple sites in the MSLN coding region, rather than its 3'UTR, with an additive effect that leads to an almost complete block of MSLN protein expression. While not bound by the hypothesis, this may imply that dysregulation of MSLN or another component of the MSLN→NF-κB→OCT-2 pathway or other genomic insults affecting miR-198 expression can result in downregulation of miR-198 and activation of a feed-forward mechanism resulting in MSLN overexpression. MiR-198 effectively reverses the effects of MSLN in PC cells and tumors through direct modulation, and thus indirectly regulates NF-κB activation and OCT-2 induction, potentially altering a very vast array of tumorigenic properties that define aggressive tumors.

In addition, miR-198 also targets the tumorigenic factors PBX-1 and VCP. PBX-1 dysregulation has been implicated in increased proliferation of cancer cells (Park et al., 2008; Shiraishi et al., 2007); VCP overexpression correlates with increased progression and metastatic potential of a variety of cancers (Tsujimoto et al., 2004; Yamamoto et al., 2004a; Yamamoto et al., 2004b; Yamamoto et al., 2004c; Yamamoto et al., 2004d; Yamamoto et al., 2004e). However, this disclosure demonstrates for the first time that modulation of PBX-1 in PC cells contributes to MSLN-mediated proliferation. In addition, the results indicate a novel role for the PBX-1/VCP axis in PC cell migration, and implicate PBX-1 as a factor responsible for the metastatic potential of MSLN-overexpressing cells. Previous studies have linked the PBX-1/VCP axis to metastatic potential and survival through the VCP-mediated activation of NF-κB (Asai et al., 2002). NF-κB also reciprocally modulates PBX-1 and VCP expression through the regulation of miR-198 and the interconnectivity of the interactome. VCP can thereby feed back into the pathway, promoting maintenance of NF-κB activation, OCT-2 induction, and subsequent miR-198 repression.

The PBX-1/VCP axis is important in cell survival under cytokine stress, as demonstrated by the resistance of PBX-1/VCP overexpressing cells in TNF-α mediated induction of apoptosis (Qiu et al., 2007). It was reported that MSLN overexpressing cells are resistant to the apoptotic effects of TNF-α (Bharadwaj et al., 2011a), and here it is shown that miR-198 reconstitution can act as an antagonist of these increased cell survival effects. Taken together, the results show that miR-198 mediated modulation of the interactome has implications in preventing chemotherapeutic resistance of PC cells.

The examples identify an interactome of molecular entities that can be of prognostic value and provide insight into the diseased state of PC patients. The dynamic behavior and function of a previously uncharacterized signaling network was elucidated which gives rise to an aggressive phenotype with clinical implications. The importance of miR-198 as a central component of this network is underscored by the significant reversal in tumorigenic aggressiveness that accompanies miR-198 reconstitution and the subsequent alteration in the molecular makeup of tumors. In addition to elucidating the molecular mechanisms through which MSLN promotes pathogenesis, the examples below identify OCT-2 and the PBX-1/VCP axis as critical biomarkers and targets for PC treatment. By acting as the key regulator of this network, miR-198 replacement therapy has the potential to influence the interactions between these molecules and revert the most aggressive pancreatic tumors to a more manageable, less invasive phenotype, and has wide reaching therapeutic potential for other cancers where MSLN, OCT-2, PBX-1 or VCP play important roles either individually or as part of this functional network.

Pancreatic Cancer

As the fourth leading cause of cancer-related deaths in North America, pancreatic cancer has the highest fatality rate of all cancers. Survival statistics are poor, because there are no reliable tests for early diagnosis and no effective therapies for the metastatic form of pancreatic cancer (Landis et al., 1998; Torrisani and Buscail, 2002; Warshaw and Fernandez-del Castillo, 1992). By the time diagnosis is made, the disease has usually spread to distant sites of the body.

Representative symptoms of pancreatic cancer include pain in the abdomen and back, loss of appetite, bloating, diarrhea or fatty bowel movements, and jaundice, for example. Diagnosis may be made on physical exam, abdominal ultrasound, and/or abdominal computed tomography, for example. A biopsy may be performed either percutaneously or endoscopically. Treatment is usually through chemotherapy, radiation therapy, and surgery. The most commonly used chemotherapies are gemcitabine, fluorouracil, and capecitabine. The present invention may be employed with any conventional treatment of PC, for example.

In an embodiment of the disclosure, levels of MSLN, OCT-2, PBX-1, VCP, ZEB1 or a combination thereof are measured in the cancer of the individual. In an embodiment of the disclosure, either the levels of RNA or protein may be measured. In one example, if the levels of MSLN, OCT-2, PBX-1, VCP, and/or ZEB1 are high, then the individual is given a higher dose of miRNA-198 therapy. If the levels of MSLN, OCT-2, PBX-1, VCP, and/or ZEB1 are low, then the patient prognosis and survival is predicted to be high. While there are many variants of these proteins and genes, as examples, the following accession numbers may be used: MSLN: NM_005823; OCT2: NM_002698; PBX-1: NM_002585; VCP: NM_025054; and ZEB1: NM_001174094. An embodiment of the disclosure is a method of predicting patient outcome comprising the step of measuring the protein or RNA levels of MSLN, OCT-2, PBX-1, VCP, and/or ZEB1 in an individual with cancer.

miRNA-198 Therapy

MiRNA-198 therapy refers to a therapy that increases the level of active microRNA-198 molecules in a cell. The increase can come about by directly providing the microRNA-198 to a cell, or may come about by indirectly providing miRNA-198 to cell, such as through a vector. The miRNA-198 may be comprised on a RNA or DNA molecule that also comprises additional sequences. In some instances of the disclosure, the miRNA-198 therapy is SEQ ID NO: 1.

In another embodiment of the invention, the miRNA-198 is the seed region of miRNA-198 which is the first 12 nucleotides of SEQ ID NO: 1. In other embodiments, the miRNA-198 sequence differs from SEQ ID NO:1 at 1, 2, 3, 4, 5, 6, 7, 8, 9, 10, 11, 12 or more nucleotides. In other embodiments, the miRNA-198 sequence includes an insertion of 1, 2, 3, 4, 5, 6, 7, 8, 9, 10, 11, 12 or more nucleotides. In other embodiments, the miRNA-198 sequence includes the deletion of 1, 2, 3, 4, 5, 6, 7, 8, 9, 10, 11, 12 or more nucleotides. In some embodiments, the miRNA-198 will include one or more different nucleotides, one or more deleted nucleotides, and/or one or more inserted nucleotides.

The miRNA-198 therapy may also comprise a nucleic acid strand that is complimentary to miRNA-198. For example, the miRNA-198 complimentary strand comprises 22 nucleotides that are complimentary to SEQ ID NO.1. The complimentary strand may also only comprise 12 nucleotides that are complimentary to the seed sequence of miRNA-198. The complimentary strand may also comprise at least one nucleotide sequence difference when compared with the true reverse complement sequence of the seed region of the guide strand, wherein the at least one nucleotide difference is located within nucleotide position 13 to the 3' end of said complimentary strand.

Strands or regions that are complementary may or may not be 100% complementary ("completely or fully complementary"), including to SEQ ID NO: 1. It is contemplated that sequences that are "complementary" include sequences that are at least about 50% complementary, and may be at least about 50%, 60%, 70%, 80%, or 90% complementary. In the range of about 50% to 70% complementarity, such sequences may be referred to as "very complementary," while the range of greater than about 70% to less than complete complementarity can be referred to as "highly complementary." Unless otherwise specified, sequences that are "complementary" include sequences that are "very complementary," "highly complementary," and "fully complementary." It is also contemplated that any embodiment discussed herein with respect to "complementary" strands or region can be employed with specifically "fully complementary," "highly complementary," and/or "very complementary" strands or regions, and vice versa. Thus, it is contemplated that in some instances, as demonstrated in the Examples, that siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability.

It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, residues or more, depending on the length of the complementarity region.

In some methods of the invention, miRNA and/or candidate miRNA molecules or template nucleic acids may be isolated or purified prior to their being used in a subsequent step. miRNA and/or candidate miRNA molecules may be isolated or purified prior to introduction into a cell. "Introduction" into a cell includes known methods of transfection, transduction, infection and other methods for introducing an expression vector or a heterologous nucleic acid into a cell. A template nucleic acid or amplification primer may be isolated or purified prior to it being transcribed or amplified. Isolation or purification can be performed by a number of methods known to those of skill in the art with respect to nucleic acids. In some embodiments, a gel, such as an agarose or acrylamide gel, is employed to isolate the miRNA and/or candidate miRNA.

In various embodiments, miRNAs are encoded by expression constructs. The expression constructs may be obtained and introduced into a cell. Once introduced into the cell the expression construct is transcribed to produce various miRNAs, such as miRNA-198. Expression constructs include nucleic acids that provide for the transcription of a particular nucleic acid. Expression constructs include plasmid DNA, linear expression elements, circular expression elements, viral expression constructs, and the like, all of which are contemplated as being used in the compositions and methods of the present invention. In certain embodiments at least about 2, 3, 4, 5, 6, 7, 8, 9, 10 or more miRNA molecules are encoded by a single expression construct. Expression of the miRNA molecules may be independently controlled by at least about 2, 3, 4, 5, 6, 7, 8, 9, 10 or more promoter elements. In certain embodiments, at least about 2, 3, 4, 5, 6, 7, 8, 9, 10 or more expression constructs may introduced into the cell. Each expression construct may encode 1, 2, 3, 4, 5, 6, 7, 8, 9, 10 or more miRNA molecules. In certain embodiments miRNA molecules may be encoded as expression domains. Expression domains include a transcription control element, which may or may not be independent of other control or promoter elements; a nucleic acid encoding an miRNA; and optionally a transcriptional termination element. In other words, an miRNA cocktail or pool may be encoded by a single or multiple expression constructs. In particular embodiments the expression construct is a plasmid expression construct.

The delivery of the miRNA therapy may occur through several forms, such as through encapsulation of a chemically modified or through an unmodified RNA moiety within a viral or non-viral delivery vessel. Non-viral deliver vessels include nanoparticles, microparticles, liposomes, etc., which may be targeted to a cancer site or systemic. The miRNA-198 therapy can also be delivered as a plasmid or minivector based expression system where it can then be expressed and processed by the RNAi machinery in cells to form a mature miR-198 form or a derivative thereof. In an embodiment of the invention, a nanoparticle based, targeted delivery system of encapsulated miR-198 oligonucleotide and/or a plasmid expressing miR-198 is utilized.

Nucleic Acid-Based Expression Systems

In certain aspects of the invention, an agent comprising a nucleic acid, such as miRNA-198 is employed. Such an agent may be comprised within an expression system, such as on a vector, although alternatively the agent is not comprised within an expression system.

Vectors

Nucleic acids of the invention, particularly DNA templates or DNA constructs for miRNA expression, may be produced recombinantly. Protein and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTM 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with R galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors

Retroviruses have promise as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding a polynucleotide of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co expressed with other selected RNAs or proteinaceous sequences in the same host cell. Co-expression may be achieved by co transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a miRNA-198 therapy or polynucleotide encoding same. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art.

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as E. coli (e.g., E. coli strain RR1, E. coli LE392, E. coli B, E. coli X 1776 (ATCC No. 31537) as well as E. coli W3110 (F, lambda, prototrophic, ATCC No. 273325), DH5α, JM109, and KC8, bacilli such as Bacillus subtilis; and other enterobacteriaceae such as Salmonella typhimurium, Serratia marcescens, various Pseudomonas specie, as well as a number of commercially available bacterial hosts such as SURE® Competent Cells and SOLOPACK® Gold Cells (STRATAGENE®, La Jolla). In certain embodiments, bacterial cells such as E. coli LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Pharmaceutical Preparations

Pharmaceutical compositions of the present invention comprise an effective amount of one or more agents such as the miRNA-198 therapy and may include one or more additional agents, wherein any of the agents are dissolved or dispersed in or provided with a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one miRNA-198 therapy and, in some embodiments, an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The miRNA-198 therapy may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The miRNA-198 therapy may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include an miRNA-198 therapy, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the miRNA-198 therapy may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In preferred embodiments of the present invention, the miRNA-198 therapy is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, miRNA-198 therapy may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 67,537,514, 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Combination Treatments

In certain aspects, the therapy of the invention may be combined with other agents that are effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. The compositions of the present invention are considered anti-cancer agents.

More generally, these other compositions or methods would be provided in a combined amount effective to kill or inhibit proliferation of the cancer cell. This process may involve contacting the cells with miRNA-198, which may be referred to as the first agent, and the second agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that the miRNA-198 therapy could be used similarly in conjunction with chemotherapeutic, radiotherapeutic, or immunotherapeutic intervention, in addition to other pro-apoptotic or cell cycle regulating agents, for example.

Alternatively, the inventive therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, wherein inventive therapy is "A" and the secondary agent, such as radio- or chemotherapy, is "B":

| A/B/A | B/A/B | B/B/A | A/A/B | A/B/B | B/A/A | A/B/B/B | B/A/B/B |
| B/B/B/A | | B/B/A/B | A/A/B/B | A/B/A/B | | A/B/B/A | B/B/A/A |
| B/A/B/A | | B/A/A/B | A/A/A/B | B/A/A/A | | A/B/A/A | A/A/B/A |

Administration of the therapeutic agents of the present invention to a patient will follow general protocols for the administration of chemotherapeutics, taking into account the toxicity, if any, of the composition. It is expected that the treatment cycles would be repeated as necessary. It also is contemplated that various standard therapies, as well as surgical intervention, may be applied in combination with the described hyperproliferative cell therapy.

Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, oxaliplatin, taxol, gemcitabien, navelbine, farnesyl-protein tansferase inhibitors, transplatinum, 5-fluorouracil, vincristin, vinblastin and methotrexate, or any analog or derivative variant of the foregoing. Any of these therapies may be used in combination with the invention.

There is no effective specific chemotherapeutics for pancreatic cancer. The way the chemotherapy is given depends on factors such as the type and stage of the cancer being treated, and one of skill in the art would identify which chemotherapy to use given the type and stage of the cancer, for example. Systemic chemotherapy with single-agent gemcitabine or a gemcitabine-based regimen still remains one of the standards of care for the treatment of patients with locally advanced and metastatic pancreatic cancer. A recent report showed that addition of Gemcitabine to radiation and 5-FU treatment after the surgery helped patient live longer. For advanced, inoperable pancreatic cancer, patients with combination of Gemcitabine and Cisplatin or oxaliplatin (Eloxatin) treatment survive longer than single drug treatment.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the inventive therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the miRNA-198. A variety of proteins are encompassed within the invention, some of which include inducers of apoposis and/or inhibitors of cell proliferation, for example.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Kits of the Invention

Any of the compositions described herein may be comprised in a kit. In a non-limiting example, miRNA-198 and an additional agent, including an additional anti-cancer agent, in specific embodiments, may be comprised in a kit. The kits will thus comprise its contents in suitable container means.

The kits may comprise a suitably aliquoted miRNA-198 therapy, a pharmaceutical carrier, such as a lipid, and including a liposome, and/or an additional agent. Compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the miRNA-198 therapy, lipid, additional agent, and any other reagent containers in close confinement for commercial sale. Such containers may include injection or blow molded plastic containers into which the desired vials are retained.

Therapeutic kits of the present invention are kits that may comprise an miRNA-198. Additional agents may include chemical compounds or pharmaceutically acceptable salts thereof, a protein, polypeptide, peptide, inhibitor, gene, polynucleotide, vector and/or other effector. Such kits may generally contain the compositions in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The agent may also be formulated into a syringeable composition. In this case, the container means may itself be a syringe, pipette, and/or other such like apparatus, from which the formulation may be applied to an affected area of the body, injected into an animal, and/or even applied to and/or mixed with the other components of the kit. The formulation may be suitable for systemic or local delivery.

In some embodiments, the components of the kit may be provided as dried powder(s). When reagents and/or components are provided as a dry powder, the powder can be reconstituted by the addition of a suitable solvent. It is envisioned that the solvent may also be provided in another container means and may be sterile.

The container means will generally include at least one vial, test tube, flask, bottle, syringe and/or other container means, into which the inhibitory formulation is placed, and preferably is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate composition within or to the body of an animal. Such an instrument may be a syringe, pipette, forceps, and/or any such medically approved delivery vehicle.

In specific embodiments, the kit comprises an additional composition for treatment of cancer, including a chemotherapeutic drug. The kit may be tailored to include chemotherapeutic drugs suitable for the type of cancer being treated. For example, kits may be formulated for individuals with pancreatic cancer and may include in addition to the miRNA-198 one or more breast cancer drugs, such as Taxol, herceptin, tamoxifen, paclitaxel, gemcitabine, and so forth.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments and are not intended as limitations on the scope of the invention. Changes therein and other uses which are encompassed within the spirit of the invention as defined by the scope of the claims will occur to those skilled in the art.

Example 1

MiR-198 is Downregulated in Patient Tumors, and its Expression Correlates with Patient Survival Profiling PC specimens has revealed a dysregulation of miRNA expression with respect to normal tissue or chronic pancreatitis (Bloomston et al., 2007; Zhang et al., 2009); however, the functional consequences of these expression changes have not been further dissected. miRNA expression profiling was applied to study the molecular mechanisms of MSLN-mediated PC pathogenesis. In a previous study MSLN was overexpressed in MIA-PaCa2 cells, which have low endogenous MSLN levels, and it was found that MSLN overexpression led to increased migration, invasion, and proliferation both in vitro and in vivo (Bharadwaj et al., 2008; Bharadwaj et al., 2011b). Here, the expression levels of 95 cancer-associated miRNAs in MSLN overexpressing cells (MIA-MSLN) cells and vector control cells (MIA-V) was analyzed by real-time RT-PCR. A global dysregulation of miRNA expression was found, with several miRNAs being either upregulated (for instance, miR-10b, miR-196a) or downregulated (for instance, miR-198, miR-200c, miR-155) following MSLN overexpression (FIG. 1A, Table 1). MiR-198 was the most significantly downregulated of all the examined miRNAs, with a downregulation of ~15-fold. In an embodiment of the invention, overexpression of MSLN initiates a chain of events culminating in repression of miR-198 in pancreatic tumors, with the result being increased tumor growth and progression.

TABLE 1

Primers for 95 cancer-associated miRNAs and U6 snRNA control included in miRNA array shown in FIG. 2.

| miRNA | miRBASE# | miRNA sequence |
|---|---|---|
| let-7-family | MIMAT0000062, | ugagguaguagguuguauaguu, (SEQ ID NO. 2) |
| | MIMAT0000064, | ugagguaguagguuguaugguu, (SEQ ID NO. 3) |
| | MIMAT0000065, | agagguaguagguugcauagu, (SEQ ID NO. 4) |
| | MIMAT0000067 | ugagguaguagauuguauaguu (SEQ ID NO. 5) |
| miR-7 | MIMAT0000252 | Uggaagacuagugauuuuguug (SEQ ID NO. 6) |
| miR-92 | MIMAT0000092 | Uauugcacuugucccggccug (SEQ ID NO. 7) |
| miR-93 | MIMAT0000093 | Aaagugcuguucgugcagguag (SEQ ID NO. 8) |
| miR-9-1 | MIMAT0000441 | Ucuuugguuaucuagcuguauga (SEQ ID NO. 9) |
| miR-101-1 | MIMAT0000099 | Uacaguacugugauaacugaag (SEQ ID NO. 10) |
| miR-103 | MIMAT0000101 | Agcagcauuguacagggcuauga (SEQ ID NO. 11) |
| miR-106a | MIMAT0000103 | Aaaagugcuuacagugcagguagc (SEQ ID NO. 12) |
| miR-106b | MIMAT0000680 | Uaaagugcugacagugcagau (SEQ ID NO. 13) |
| miR-107 | MIMAT0000104 | Agcagcauuguacagggcuauca (SEQ ID NO. 14) |
| miR-10b | MIMAT0000254 | Uacccuguagaaccgaauuugu (SEQ ID NO. 15) |
| miR-1-1 | MIMAT0000416 | Uggaauguaaagaaguaugua (SEQ ID NO. 16) |
| miR-122a | MIMAT0000421 | Uggagugugacaauggguguuugu (SEQ ID NO. 17) |
| miR-125a | MIMAT0000443 | Ucccugagacccuuuaaccugug (SEQ ID NO. 18) |
| miR-125b | MIMAT0000423 | Ucccugagacccuaacuuguga (SEQ ID NO. 19) |
| miR-126 | MIMAT0000444 | Cauuauuacuuuugguacgcg (SEQ ID NO. 20) |
| miR-128b | MIMAT0000676 | Ucacagugaaccggucucuuuc (SEQ ID NO. 21) |
| miR-132 | MIMAT0000426 | Uaacagucuacagccauggucg (SEQ ID NO. 22) |
| miR-133a | MIMAT0000427 | Uuggucccuucaaccagcugu (SEQ ID NO. 23) |
| miR-134 | MIMAT0000447 | Ugugacugguugaccagaggg (SEQ ID NO. 24) |
| miR-135b | MIMAT0000758 | Uauggcuuuucauuccuaugug (SEQ ID NO. 25) |
| miR-136 | MIMAT0000448 | Acuccauuuguuuugaugaugga (SEQ ID NO. 26) |
| miR-137 | MIMAT0000429 | Uauugcuuaagaauacgcguag (SEQ ID NO. 27) |
| miR-140 | MIMAT0000431 | Agugguuuuacccuaugguag (SEQ ID NO. 28) |
| miR-141 | MIMAT0000432 | Uaacacugucugguaaagaugg (SEQ ID NO. 29) |
| miR-142-3p | MIMAT0000434 | Uguaguguuuccuacuuuaugga (SEQ ID NO. 30) |
| miR-143 | MIMAT0000435 | Ugagaugaagcacuguagcuca (SEQ ID NO. 31) |

TABLE 1-continued

Primers for 95 cancer-associated miRNAs and U6 snRNA
control included in miRNA array shown in FIG. 2.

| miRNA | miRBASE# | miRNA sequence |
|---|---|---|
| miR-145 | MIMAT0000437 | Guccaguuuucccaggaaucccuu (SEQ ID NO. 32) |
| miR-146a | MIMAT0000449 | Ugagaacugaauuccauggguu (SEQ ID NO. 33) |
| miR-149 | MIMAT0000450 | Ucuggcuccgugucuucacucc (SEQ ID NO. 34) |
| miR-150 | MIMAT0000451 | Ucucccaacccuuguaccagug (SEQ ID NO. 35) |
| miR-151 | MIMAT0000757 | Acuagacugaagcuccuugagg (SEQ ID NO. 36) |
| miR-153 | MIMAT0000439 | Uugcauagucacaaaaguga (SEQ ID NO. 37) |
| miR-154 | MIMAT0000452 | Uagguuauccguguugccuucg (SEQ ID NO. 38) |
| miR-155 | MIMAT0000646 | Uuaaugcuaaucgugauaggg (SEQ ID NO. 39) |
| miR-15a | MIMAT0000068 | Uagcagcacauaaugguuugug (SEQ ID NO. 40) |
| miR-15b | MIMAT0000417 | Uagcagcacaucaugguuuaca (SEQ ID NO. 41) |
| miR-16 | MIMAT0000069 | Uagcagcacguaaauauuggcg (SEQ ID NO. 42) |
| miR-17-3p | MIMAT0000071 | Acugcagugaaggcacuugu (SEQ ID NO. 43) |
| miR-17-5p | MIMAT0000070 | Caaagugcuuacagugcagguagu (SEQ ID NO. 44) |
| miR-181a | MIMAT0000256 | Aacauucaacgcugucggugagu (SEQ ID NO. 45) |
| miR-181b | MIMAT0000257 | Aacauucauugcugucgguggg (SEQ ID NO. 46) |
| miR-181c | MIMAT0000258 | Aacauucaaccugucggugagu (SEQ ID NO. 47) |
| miR-181d | MIMAT0002821 | Aacauucauuguugucggugggu (SEQ ID NO. 48) |
| miR-183 | MIMAT0000261 | Uauggcacugguagaauucacug (SEQ ID NO. 49) |
| miR-185 | MIMAT0000455 | Uggagagaaaggcaguuc (SEQ ID NO. 50) |
| miR-296 | MIMAT0000690 | Agggccccccucaauccugu (SEQ ID NO. 51) |
| miR-186 | MIMAT0000456 | Caaagaauucuccuuuugggcuu (SEQ ID NO. 52) |
| miR-188 | MIMAT0000457 | Caucccuugcauggugagggu (SEQ ID NO. 53) |
| miR-18a | MIMAT0000072 | Uaaggugcaucuagugcagaua (SEQ ID NO. 54) |
| miR-190 | MIMAT0000458 | Ugauauguuugauauauuaggu (SEQ ID NO. 55) |
| miR-191 | MIMAT0000440 | Caacggaaucccaaaagcagcu (SEQ ID NO. 56) |
| miR-192 | MIMAT0000222 | Cugaccuaugaauugacagcc (SEQ ID NO. 57) |
| miR-194 | MIMAT0000460 | Uguaacagcaacuccauggga (SEQ ID NO. 58) |
| miR-195 | MIMAT0000461 | Uagcagcacagaaauauuggc (SEQ ID NO. 59) |
| miR-196a | MIMAT0000226 | Uagguaguuucauguuguugg (SEQ ID NO. 60) |
| miR-197 | MIMAT0000227 | Uucaccaccuucucccaccagc (SEQ ID NO. 61) |
| miR-198 | MIMAT0000228 | gguccagaggggagauagg (SEQ ID NO: 1) |
| miR-199a + b | MIMAT0000231, MIMAT0000263 | cccaguguucagacuaccuguuc, (SEQ ID NO. 62) cccaguguuuagacuaucuguuc (SEQ ID NO. 63) |
| miR-30b | MIMAT0000420 | Uguaaacauccuacacucagcu (SEQ ID NO. 64) |
| miR-19a + 30b | MIMAT0000073, MIMAT0000074 | ugugcaaaucuaugcaaaacuga, (SEQ ID NO. 65) ugugcaaauccaugcaaaacuga (SEQ ID NO. 66) |
| miR-95 | MIMAT0000094 | Uucaacgguauuuauugagca (SEQ ID NO. 67) |
| miR-20a | MIMAT0000075 | Uaaagugcuuauagugcagguag (SEQ ID NO. 68) |

TABLE 1-continued

Primers for 95 cancer-associated miRNAs and U6 snRNA control included in miRNA array shown in FIG. 2.

| miRNA | miRBASE# | miRNA sequence |
| --- | --- | --- |
| miR-200a | MIMAT0000682 | Uaacacugucugguaacgaugu (SEQ ID NO. 69) |
| miR-200b | MIMAT0000318 | Uaauacugccugguaaugaugac (SEQ ID NO. 70) |
| miR-200c | MIMAT0000617 | Uaauacugccgguaaugaugg (SEQ ID NO. 71) |
| miR-202 | MIMAT0002811 | Agagguauagggcaugggaaaa (SEQ ID NO. 72) |
| miR-203 | MIMAT0000264 | Gugaaauguuuaggaccacuag (SEQ ID NO. 73) |
| miR-204 | MIMAT0000265 | Uucccuuugucauccuaugccu (SEQ ID NO. 74) |
| miR-205 | MIMAT0000266 | Uccuucauuccaccggagucug (SEQ ID NO. 75) |
| miR-206 | MIMAT0000462 | Uggaauguaaggaagugugugg (SEQ ID NO. 76) |
| miR-21 | MIMAT0000076 | Uagcuuaucagacugauguuga (SEQ ID NO. 77) |
| miR-210 | MIMAT0000267 | Cugugcgugugacagcggcuga (SEQ ID NO. 78) |
| miR-214 | MIMAT0000271 | Acagcaggcacagacaggcag (SEQ ID NO. 79) |
| miR-215 | MIMAT0000272 | Augaccuaugaauugacagac (SEQ ID NO. 80) |
| miR-372 | MIMAT0000724 | Aaagugcugcgacauuugagcgu (SEQ ID NO. 81) |
| miR-373 | MIMAT0000726 | Gaagugcuucgauuuggggugu (SEQ ID NO. 82) |
| miR-22 | MIMAT0000077 | Aagcugccaguugaagaacugu (SEQ ID NO. 83) |
| miR-488 | MIMAT0002804 | Cccagauaauggcacucucaa (SEQ ID NO. 84) |
| miR-221 | MIMAT0000278 | Agcuacauugucugcuggguuuc (SEQ ID NO. 85) |
| miR-222 | MIMAT0000279 | Agcuacaucuggcuacugggucuc (SEQ ID NO. 86) |
| miR-223 | MIMAT0000280 | Ugucaguuugucaaauacccc (SEQ ID NO. 87) |
| miR-224 | MIMAT0000281 | Caagucacuagugguuccguuua (SEQ ID NO. 88) |
| miR-23a | MIMAT0000078 | Aucacauugccagggauuucc (SEQ ID NO. 89) |
| miR-24 | MIMAT0000080 | Uggcucaguucagcaggaacag (SEQ ID NO. 90) |
| miR-25 | MIMAT0000081 | Cauugcacuugucucggucuga (SEQ ID NO. 91) |
| miR-26a | MIMAT0000082 | Uucaaguaauccaggauaggc (SEQ ID NO. 92) |
| miR-26b | MIMAT0000083 | Uucaaguaauucaggauagguu (SEQ ID NO. 93) |
| miR-27a + 30b | MIMAT0000084, MIMAT0000419 | uucacaguggcuaaguuccgc, (SEQ ID NO. 94) uucacaguggcuaaguucugc (SEQ ID NO. 95) |
| miR-30c | MIMAT0000244 | Uguaaacauccuacacucucagc (SEQ ID NO. 96) |
| miR-29a + b + c | MIMAT0000086, MIMAT0000100, MIMAT0000681 | uagcaccaucugaaaucgguu, (SEQ ID NO. 97) uagcaccauuugaaaucaguguu, (SEQ ID NO. 98) uagcaccauuugaaaucggu (SEQ ID NO. 99) |
| miR-30a-3p | MIMAT0000088 | Cuuucagucgauguuugcagc (SEQ ID NO. 100) |
| miR-30a-5p | MIMAT0000087 | Uguaaacauccucgacuggaag (SEQ ID NO. 101) |
| U6 snRNA | NCBI: X07425.1 | Caccacguuuauacgccggug (SEQ ID NO. 102) |

Figure 1B:
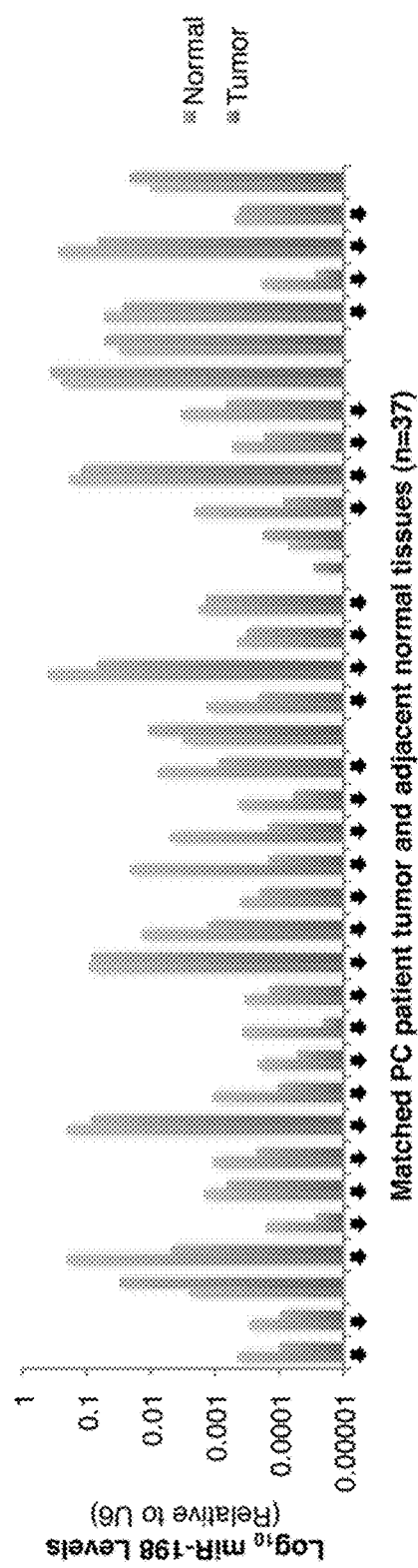

To determine the clinical relevance of miR-198 expression in PC miR-198 expression in 37 PC patients was examined, and it was found that miR-198 was downregulated in 78.4% of tumors compared to adjacent normal tissues (FIG. 1B), with downregulation ranging from 2-142 fold, and an average downregulation of 10 fold (Table 2). The cohort of patients were classified into two groups based on miR-198 tumor levels: miR-198-Low and miR-198-High. All patients in the miR-198-Low group (n=26), had a miR-198 level of $<1*10^{-3}$ (relative to U6 control), with an average relative miR-198 level of 0.0004; all patients in miR-198-High group had a minimum of a ten-fold higher level of miR-198, with a level of $>1*10^{-2}$ and an average relative miR-198 of 0.08, a greater than 100 fold increase over the miR-198-Low group (p<0.0005).

TABLE 2

Fold changes of network factors in tumor tissues compared to matched normal tissues for PC patients.

|  | Patient # | OCT-2 | VCP | PBX-1 | MSLN | MIR-198 | FSTL1 |
|---|---|---|---|---|---|---|---|
| miR-198 low | 1 | 13.90 | 4.42 | 2.91 | 1.87 | -4.44 | -1.43 |
|  | 2 | 5.15 | 5.75 | 6.08 | 7.61 | -2.98 | -1.39 |
|  | 3 | 6.96 | 7.46 | 3.32 | 6.25 | -6.80 | -3.86 |
|  | 4 | 41.44 | 17.76 | 51.51 | 30.12 | -42.44 | -45.95 |
|  | 5 |  |  |  |  | -5.88 |  |
|  | 6 |  |  |  |  | -2.23 |  |
|  | 7 | 2.20 | 10.44 | 8.46 | 1.92 | -4.71 | -4.17 |
|  | 8 | 15.93 | 43.67 | 56.49 | 30.55 | -24.03 | -10.26 |
|  | 9 | 7.02 | 11.91 | 28.21 | 13.71 | -10.16 | -7.82 |
|  | 10 | 4.66 | 7.08 | 7.94 | 1.54 | -4.13 | -1.25 |
|  | 11 | 5.86 | 3.74 | 18.95 | 10.56 | -17.91 | -10.57 |
|  | 12 | 4.08 | 17.74 | 12.33 | 6.08 | -2.38 | -2.94 |
|  | 13 | 5.69 | 4.45 | 9.92 | 2.13 | -3.21 | -1.29 |
|  | 14 | 5.40 | 12.91 | 1.72 | 3.25 | -10.79 | -20.52 |
|  | 15 | 5.60 | 2.77 | 6.01 | 6.32 | -1.99 | -7.91 |
|  | 16 | 52.06 | 13.49 | 81.28 | 100.88 | -142.38 | -146.64 |
|  | 17 | 12.85 | 4.35 | 18.20 | 36.06 | -33.73 | -12.00 |
|  | 18 | 2.99 | 2.46 | 1.19 | 8.58 | -7.19 | -4.24 |
|  | 19 | 14.25 | 3.61 | 1.99 | 6.87 | -8.79 | -6.66 |
|  | 20 | 1.78 | 1.10 | 1.78 | 1.19 | -1.19 | 0.59 |
|  | 21 | 1.96 | 1.36 | 7.26 | 3.21 | -6.36 | -1.54 |
|  | 22 | 3.47 | 7.50 | 2.76 | 2.49 | -5.06 | -2.35 |
|  | 23 | 2.70 | 4.09 | 45.69 | 3.72 | -1.42 | -6.10 |
|  | 24 | 2.94 | 2.89 | 6.68 | 16.31 | -1.28 | -2.13 |
|  | 25 | -1.95 | 1.45 | -1.78 | -1.24 | 3.32 | 1.43 |
|  | 26 | -5.22 | 1.65 | -1.04 | -2.51 | 2.47 | 1.24 |
| miR-198-High | 27 | 1.43 | -1.36 | -9.16 | 4.44 | -2.40 | -2.73 |
|  | 28 |  |  |  | 1.15 | 1.55 |  |
|  | 29 | 1.07 |  | 2.51 | -6.48 | -1.07 | -1.47 |
|  | 30 |  |  |  | 13.93 | -5.88 |  |
|  | 31 |  |  |  | -1.23 | 1.48 |  |
|  | 32 | 2.70 | 1.07 | 2.30 | 2.90 | 1.66 | -2.07 |
|  | 33 | -17.85 | -8.82 | 1.39 | -6.88 | -2.01 | -2.24 |
|  | 34 | -3.39 | -1.15 | -79.22 | -2.39 | 12.33 | 2.97 |
|  | 35 | 1.71 | 3.37 | -1.15 | 1.60 | -4.21 | -1.96 |
|  | 36 | -8.76 | -1.36 | -1.19 | -1.46 | 3.38 | 1.82 |
|  | 37 | -1.07 | 1.21 | 1.92 | -1.07 | 2.16 | 1.11 |
| AVG FOLD CHANGE |  | 5.86 | 6.03 | 9.23 | 8.63 | -9.15 | -9.45 |
| COLOR KEY |  | Opposite/ No change | 1.01-2- fold | 2-10 fold | 10-100 fold | 100+ fold |  |

Figure 1C:
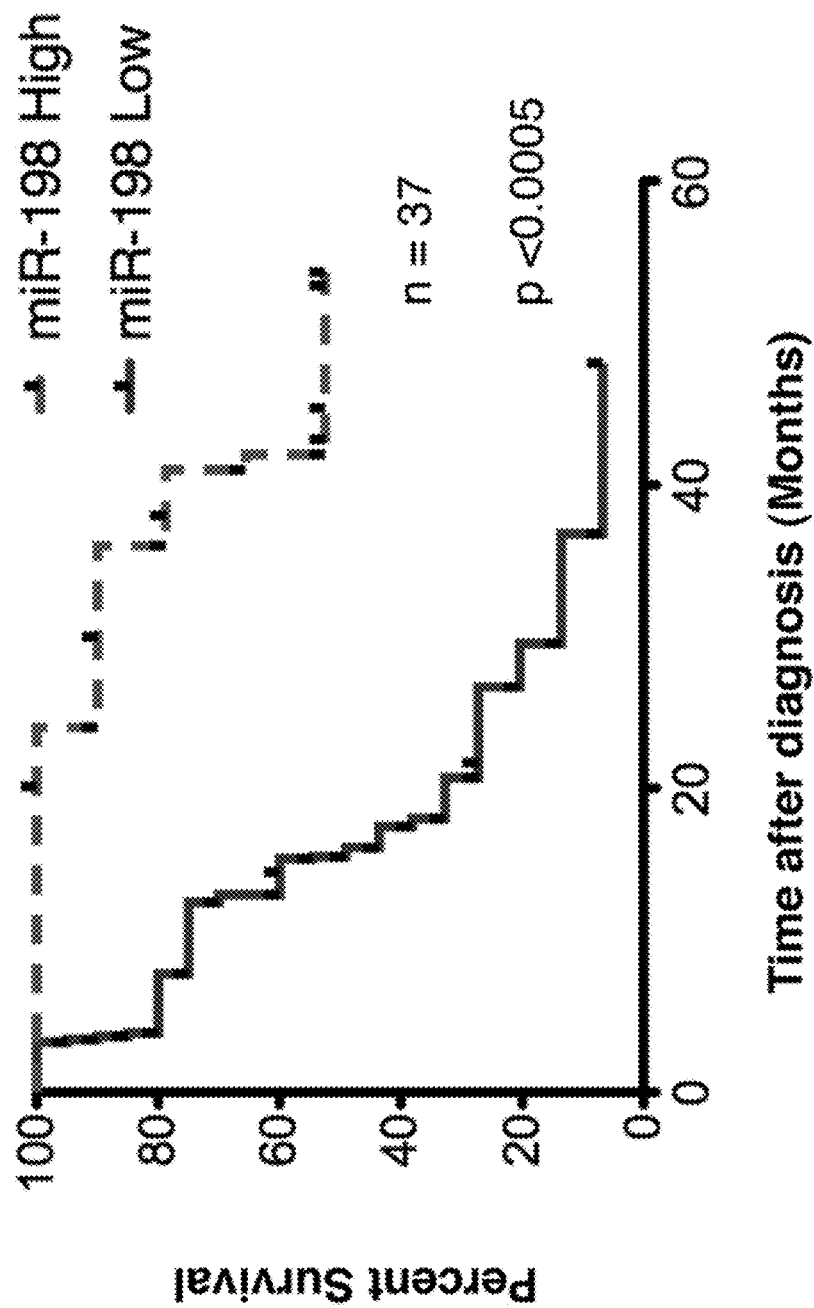

Patient survival in the two groups was examined. As measured by Log-rank test, patient survival was significantly increased in the miR-198-High group compared to the low group, (p=0.0002, Chi Square=14.12 df=1), with a hazard ratio of 5.815 (95% Cl of ratio 2.321 to 14.57) (FIG. 1C). The median survival of the miR-198-Low patients was ~15.5 months, with only 11% of patients still alive after ~40 months. Conversely, miR-198-High patients who had died had a median survival time of 35.75 months, with 80% of miR-198-High patients were still alive at 40 months, and 64% still alive after ~60 months. These results clearly implicate the clinical significance of miR-198 being an important prognostic factor in PC.

Example 2

Figure 9A:
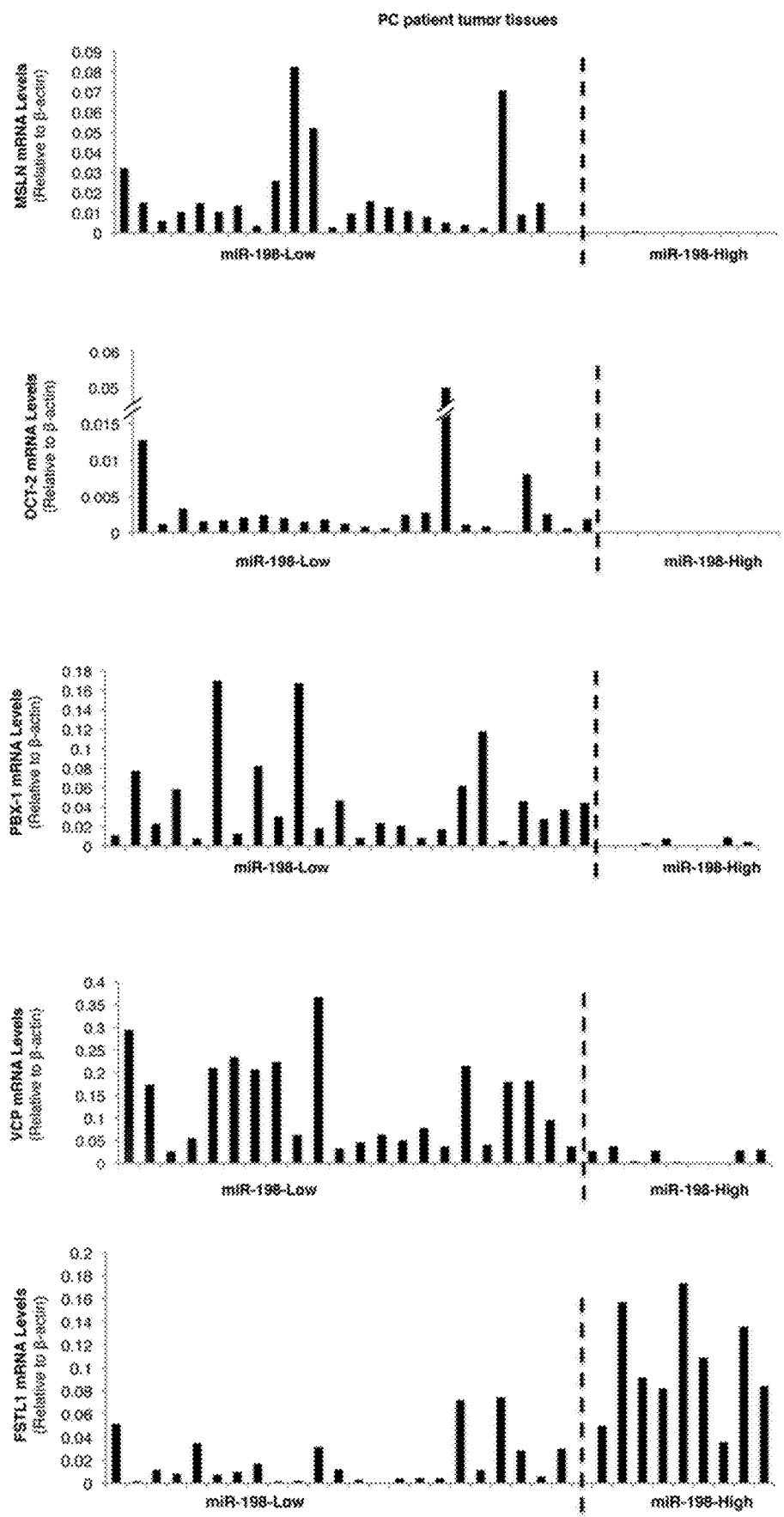
FIGS. 9A and 9B illustrate miR-198 modulation in stable cell lines.

An Interactome of Tumorigenic Factors Interconnected Through miR-198 Serves as a Prognostic Indicator of PC MiR-198 is an intronic miRNA, located in the 3'UTR of the gene for human follistatin related protein (FSTL-1) (Cullen, 2004; Rodriguez et al., 2004). While most intronic miRNAs tend to be under the control of the same promoter as their host gene, the relationship between FSTL1 and miR-198 had not yet been established. Therefore, the FSTL1 mRNA levels in the matched tissues was examined, and a close correlation with miR-198 expression (p<0.05, $R_{2=0.95}$) was found. The miR-198-Low group had an average relative FSTL1 mRNA level (normalized to β-actin) of 0.01, while it was ten-fold higher in the miR-198-High group, at 0.10 (FIG. 9A).

In silico analyses was performed on the FSTL-1/miR-198 promoter to determine potential binding sites for repressive transcription factors that could be downregulating miR-198 expression in tumors (Table 3). The potential involvement of several transcription factors including OCT-2, ZEB-1 and KLF4 (data not shown) was also studied. Several octamer motif binding sites for the repressive POU domain binding factor OCT-2 (consensus sequence ATGCAAAT) were identified. While OCT-2 expression had never been studied in PC, here it was found that OCT-2 was expressed in the pancreas, and was upregulated in ~81% of patient tumors (FIG. 9A). OCT-2 mRNA expression, while low in normal tissues, was upregulated ~6 fold on average in matched patient tumors (Table 2). When the OCT-2 expression was examined in the two cohorts of patients segregated by miR-198 levels, a clear distinction was found between the two groups with respect to OCT-2 levels (FIG. 9A). The average OCT-2 tumor expression level was $3.2*10^{-5}$ in the miR-198-High group (relative to β-actin), while this was upregulated to an average 4.4*10⁻³ in the miR-198-Low group, a >100-fold change in relative expression of OCT-2 in the tumor tissues between the two groups (p=0.25, 95% CI=−0.003391 to 0.01214).

TABLE 3

Conserved Transcription Factor Binding Sites in FSTL1/miR-198 promoter region. Number of OCT-2 binding sites in bold.

| Transcription Factor Name | Number of Sites in miR-198 promoter |
|---|---|
| AIRE | 1 |
| AREB6 | 2 |
| BACH2 | 1 |
| BARBIE | 1 |
| CETS16B | 1 |
| CP2 | 1 |
| CREB | 2 |
| CREBATF | 1 |
| CREL | 1 |
| DR3 | 1 |
| E12 | 1 |
| E2F | 1 |
| E2F1 | 1 |
| E2F1DP1 | 1 |
| E2F1DP2 | 1 |
| E2F4DP2 | 1 |
| E47 | 2 |
| ELF1 | 2 |
| EVI1 | 1 |
| FOXJ2 | 1 |
| FREAC3 | 1 |
| GABP | 1 |
| GCM | 1 |
| HAND1E47 | 2 |
| HEB | 1 |
| HES1 | 1 |
| HFH3 | 1 |
| HFH8 | 1 |
| HNF3ALPHA | 1 |
| HNF3B | 1 |
| IK3 | 1 |
| KLF4 | 6 |
| LDSPOLYA | 1 |
| MAZR | 1 |
| MMEF2 | 1 |
| MTATA | 1 |
| MYOD | 2 |
| NFKAPPAB65 | 1 |
| NKX25 | 1 |
| NRF2 | 1 |
| OCT1/OCT2 | 3 |
| OSF2 | 2 |
| PBX-1 | 1 |
| POUF1 | 1 |
| RFX1 | 2 |
| TAL1 | 1 |
| TATA | 1 |
| TCF1P | 3 |
| TITF1 | 2 |
| USE | 1 |
| XFD1 | 1 |
| XFD2 | 1 |
| XFD3 | 1 |
| ZEB1 | 17 |

MSLN was upregulated in 77% of patient tumors, with an average of 8.6 fold increase in expression in tumors over normal tissues (Table 2). There was a significant difference in the average relative MSLN levels in patient tumors between the miR-198-Low (1.8×10⁻²) and miR-198-High groups (8.5×10⁻⁴) (p<0.05) (FIG. 9A).

MiRNA target prediction software was used to find potential miR-198 targets through which miR-198 might be modulating tumorigenesis in PC cells. A microarray was used to screen targets for changes in expression within the miR-198-High and miR-198-Low groups and selected two candidates that had a differential expression in response to miR-198 levels, PBX-1 and VCP. A potential miR-198 binding site was identified within the 3'UTR of PBX-1 (FIG. 10A). This binding site is evolutionarily conserved in 22 of 23 species examined (FIG. 10C). In addition to its direct effects on tumorigenicity, PBX-1 is also a regulator of VCP, and increased expression of the PBX-1-VCP axis has been associated with cancer metastasis, increased cell survival, and poor prognosis of patients with PC (Qiu et al., 2007). It was also found that VCP also has a binding site for miR-198 within its 3'UTR (FIG. 10B), which is conserved in a majority of species (FIG. 10D). Both PBX-1 and VCP were upregulated in a majority of patient tumors (81.3% and 87.1%, respectively), with an average upregulation of ~9 and ~6 fold, respectively. A clear distinction was observed between the miR-198-Low and High groups, with an average relative PBX-1 and VCP level ~10 fold higher in the miR-198-Low group compared to the miR-198-High group (PBX-1: 0.04 and 0.003, p<0.05, and VCP: 0.12 and 0.013, respectively. p<0.05) (Table 2, FIG. 9A).

Figure 1D:
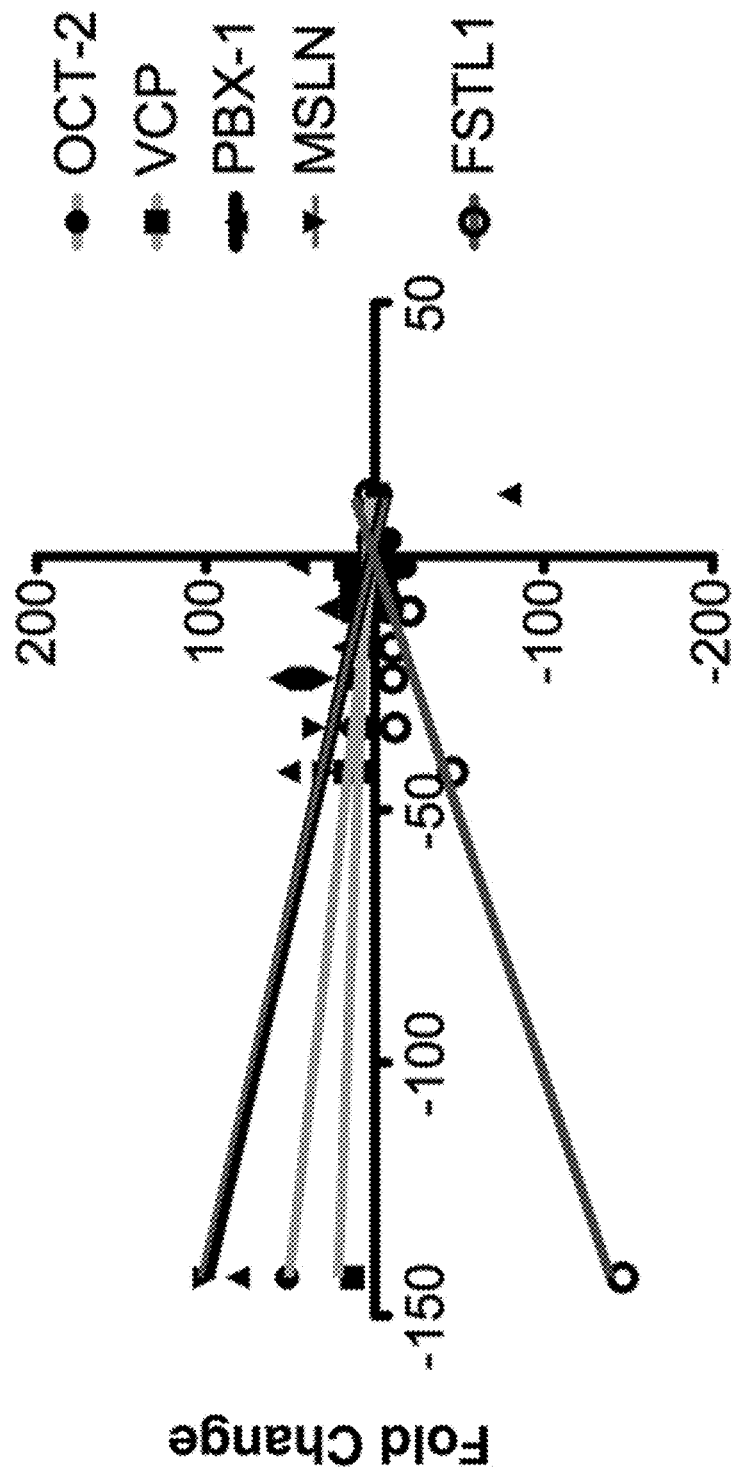
Figure 1E:
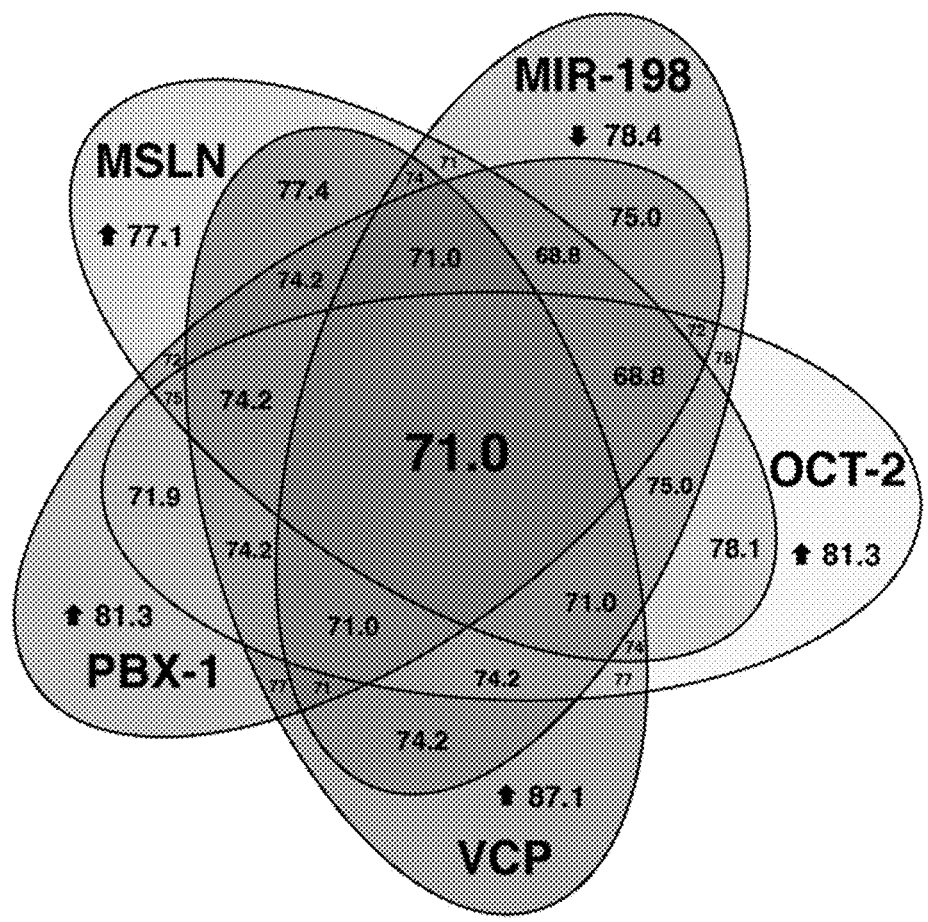
Figure 1F:
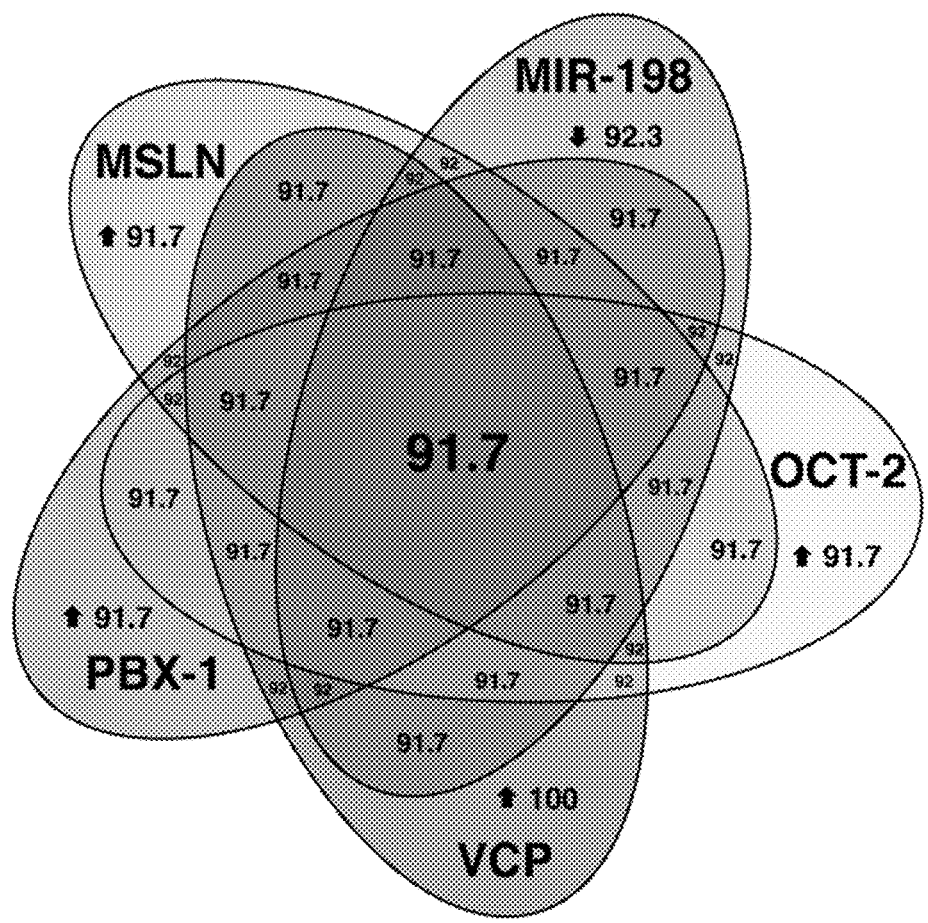
Figure 1G:
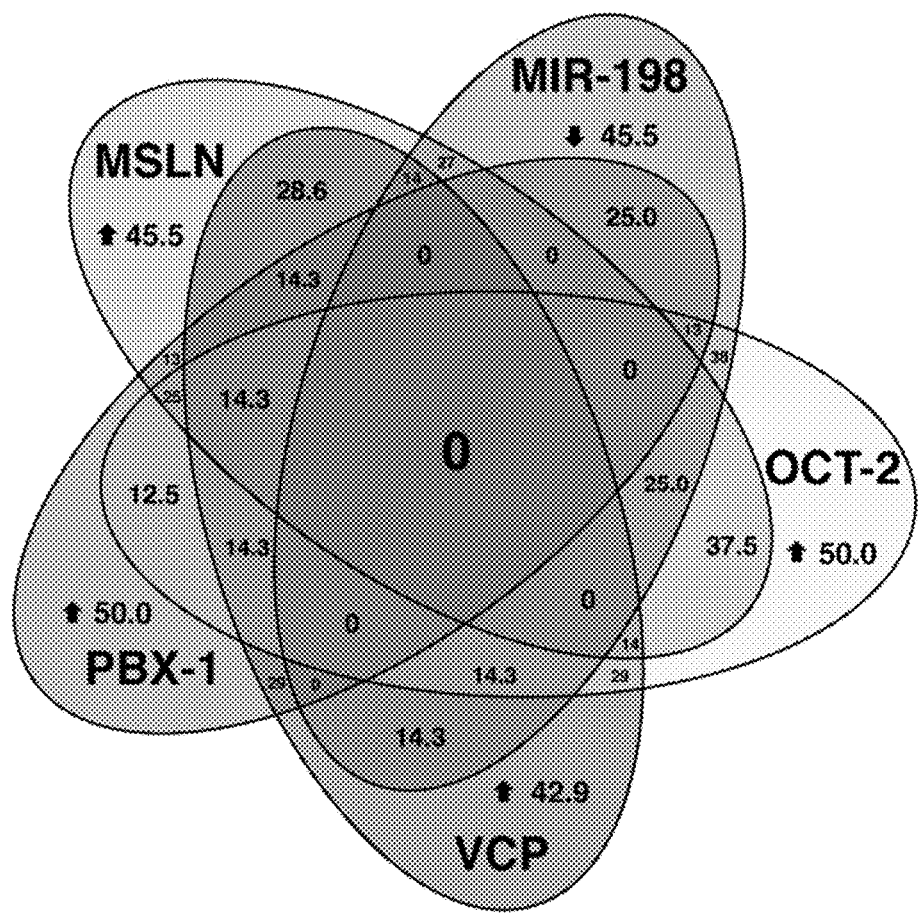
Figure 9B:
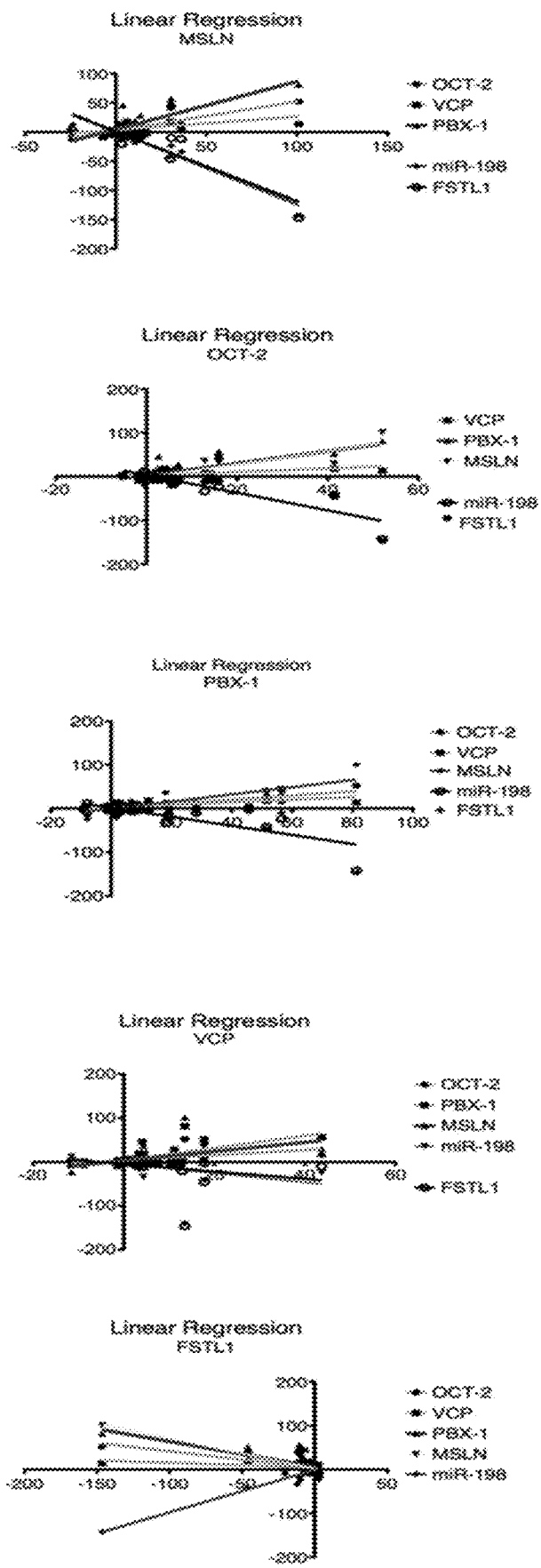

If the factors in this network are linked through miR-198, then the changes in their expression of all of the factors would correlate with each other. FIG. 1D shows the linear regression analysis for the fold changes in expression of all these factors between the tumor and normal matched samples in relation to miR-198. FSTL1 correlates with miR-198 (p<0.0005, $R^2$=0.95), while there is a negative correlation between miR-198 and OCT-2 (p<0.0005, $R^2$=0.79), MSLN (p<0.0005, $R^2$=0.92), PBX-1 (p<0.0005, $R^2$=0.63), and VCP (p<0.05, $R^2$=0.14) in patient tumor tissues. All these factors also correlate positively with each other and negatively with miR-198 and FSTL1 (FIG. 9B), indicating that the changes in their expression may be dependent on each other as members of this network.

The complex interactome between the factors was further represented using the five-order Venn diagrams depicted in FIG. 1, E-G. The fold changes of each factor was examined between tumor and adjacent normal tissues and the percentage of times upregulation occurred from normal to tumor was calculated for MSLN, OCT-2, PBX-1, or VCP individually, and how often the upregulation in each was accompanied by an upregulation in the other factors as well as downregulation of miR-198. To reduce complexity, FSTL1 was not included in this graphical representation, as its close correlation with miR-198 expression makes them interchangeable in this analysis. As shown in FIG. 1E, for the total (n=37) samples of patient tissues, a downregulation in miR-198 was accompanied by a simultaneous upregulation in all other network members (MSLN, OCT-2, PBX-1, and VCP) in 71% of tumors. When the same analysis was performed for either the miR-198-Low or miR-198-High groups separately, a very clear change in the molecular makeup of this interactome was observed. As shown in FIG. 1F, a simultaneous upregulation of MSLN, OCT-2, PBX-1, and VCP and downregulation of miR-198 occurs in 91.7% of the patients with the worst survival prognosis. This percentage is the same for all the other possible permutations of interactions between the different factors, indicating a very close association between their expression changes in this subset of patients. An intriguing result is shown in FIG. 1G. In the miR-198-High group, the cohort with the highest survival prognosis none (0%) of the patients shows a simultaneous modulation of the five factors in the interactome. This also extends to most of the other potential combinations in expression changes.

These results indicate that this interactive tumor signature network is very tightly correlated in PC patients with the worst prognosis, while those with the best prognosis have a global disruption in the network expression pattern; these tumors have a different functional makeup either due to or resulting in an elevated level of miR-198 and a decreased level of OCT-2, MSLN, PBX-1, and VCP.

Example 3

Figure 2A:
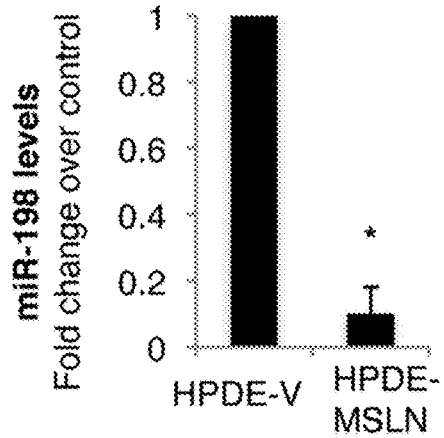
FIGS. 2A-2H illustrate MSLN regulates miR-198 expression through NF-κB-mediated induction of OCT-2.
Figure 2B:
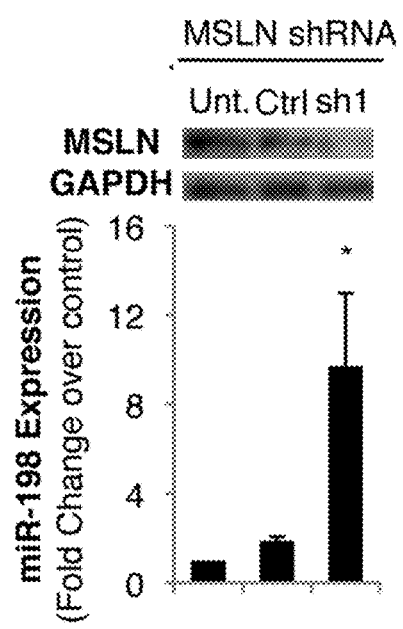

MSLN-Mediated NF-κB Activation Represses the miR-198 Promoter Through OCT-2 Induction Having demonstrated that MSLN overexpression resulted in miR-198 repression (FIG. 1A), the mechanism through which MSLN was repressing miR-198 was then determined. The findings were first confirmed in a different cell line to rule out cell-line specific effects by overexpressing MSLN in HPDE control cells. This resulted in a similar 10-fold reduction in miR-198 expression $p<0.05$ (FIG. 2A). Conversely, transfection of MSLN-specific shRNAs in MSLN-overexpressing cells restored miR-198 expression ~12 fold in MIA-MSLN cells, further indicating that MSLN was responsible for the observed miR-198 downregulation ($p<0.05$) (FIG. 2B). That is, silencing MSLN restores miR-198 expression.

Figure 2C:
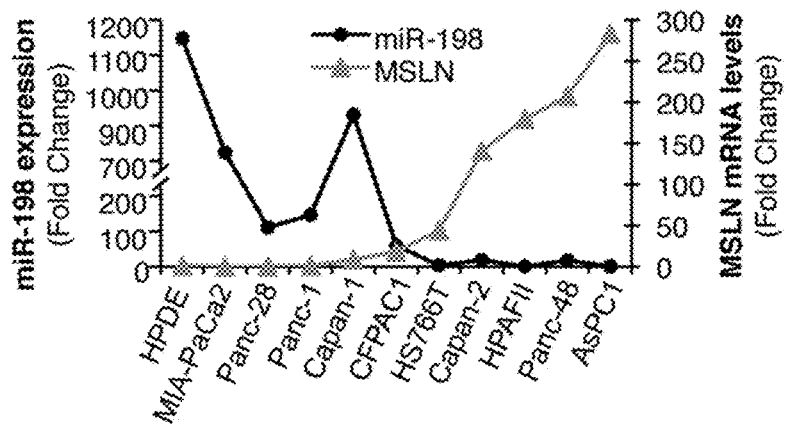
Figure 3A:
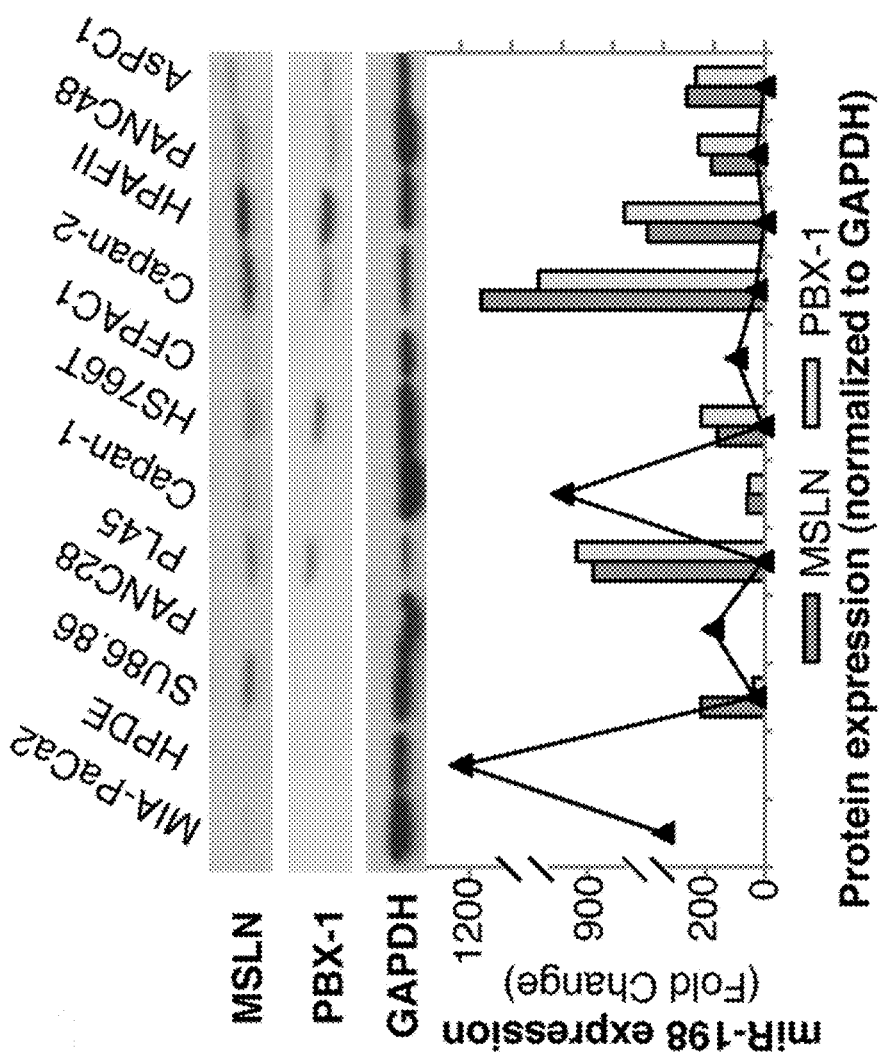
FIGS. 3A-3H illustrate that MiR-198 is the central link between upstream regulatory factors MSLN and OCT-2 and the closely correlated downstream PBX-1/VCP tumorigenic axis.

To verify that an in vitro system would recapitulate the results of the clinical data, miR-198 and MSLN expression were examined in a panel of PC cell lines (FIG. 2C) and it was found that when MSLN expression was high, miR-198 was low, which parallels observations in the patient tumors. That is, MSLN mRNA levels correlate negatively with miR-198 levels in human PC cells. Fold change was calculated relative to PC cell with lowest expression of each factor. Compared to HPDE cells and normal tissues, miR-198 expression is downregulated in majority of PC cell lines (FIG. 2C). Cell lines with low MSLN levels, such as MIA-PaCa2 and Panc-28, had the highest miR-198 levels among the PC cells, ranging from 100-700 fold greater miR-198 expression than AsPC-1 cells (which have the highest MSLN levels). Conversely, cell lines with relatively high MSLN mRNA levels (>50-fold higher expression than HPDE), had the lowest levels of miR-198 (FIG. 2C), had a pronounced negative relationship between MSLN expression at the protein level and miR-198 expression (FIG. 3A).

Figure 2D:
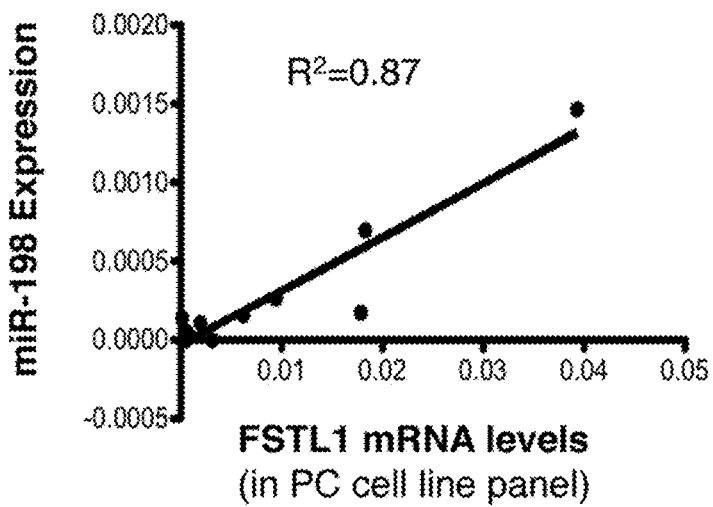
Figure 2E:
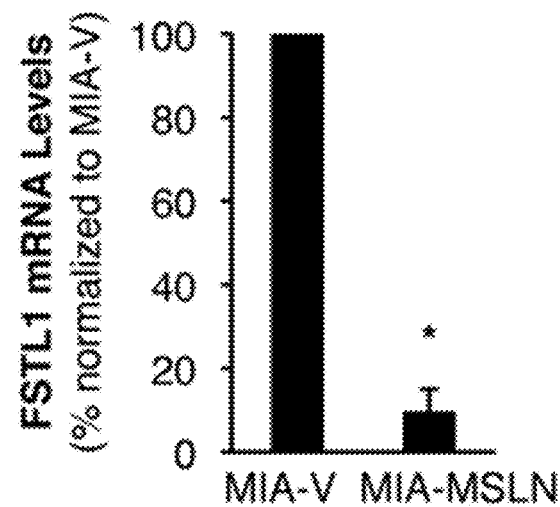

FSTL1 expression was also closely correlated with miR-198 expression ($p<0.005$) in the cell line panel (FIG. 2D; $p<0.001$, $R2=0.87$). In addition, FSTL1 mRNA levels were reduced by ~80% in MIA-MSLN cells compared to MIA-V cells following forced MSLN expression ($p<0.005$) (FIG. 2E). These results confirm that expression of miR-198 and its host gene FSTL1 are in fact linked, and that MSLN overexpression leads to a concomitant reduction in expression of both.

Figure 2F:
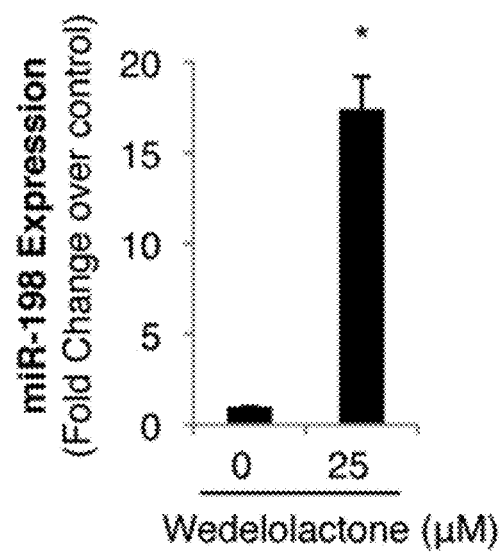
Figures 2G, 2H:
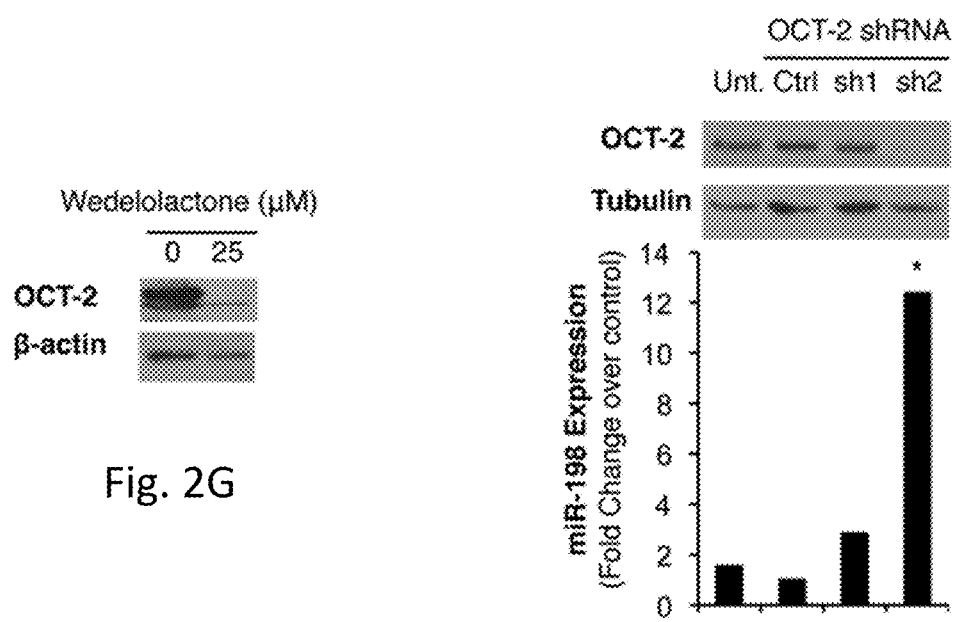
Figure 11A:
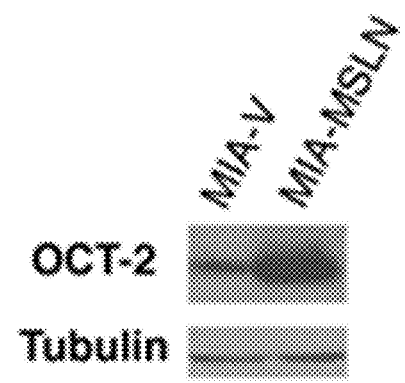
FIGS. 11A and 11B illustrate additional evidence that MSLN-mediated NF-κB activation induces OCT-2 expression.
Figure 11B:
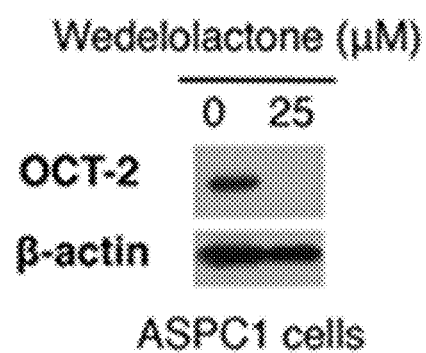
Figure 12A:
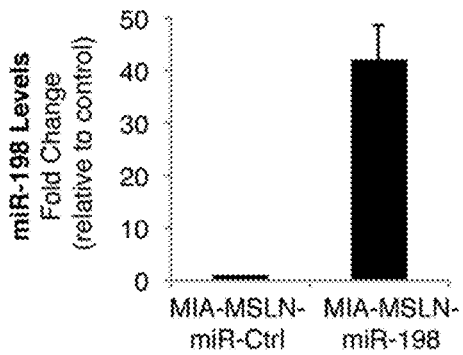
FIGS. 12A-12E illustrate miR-198 modulation in stable cell lines. Real-time RT-PCR was used to confirm miR-198 levels
Figure 12B:
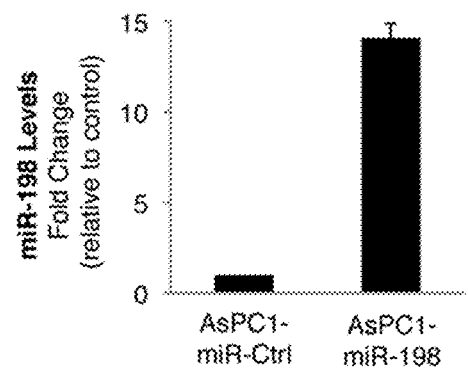
Figure 12C:
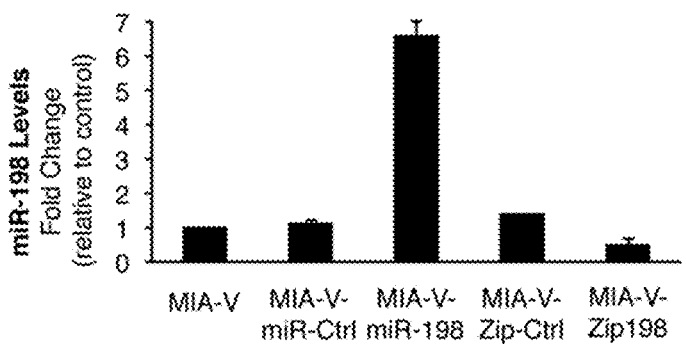
Figure 12D:
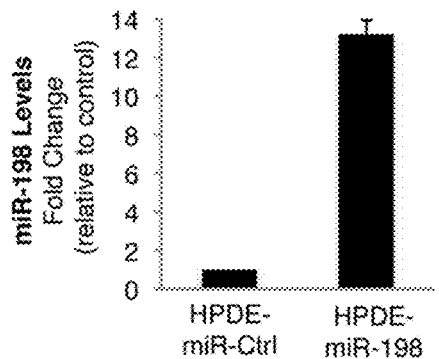
Figure 12E:
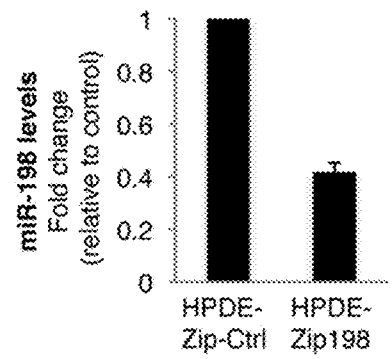
Figure 15A:
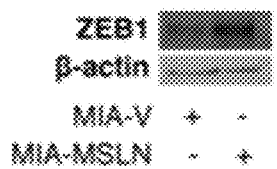
FIGS. 15A-15G illustrate evidence that ZEB1 induction represses miR-198 following MSLN-mediated NF-κB activation.
Figure 15B:
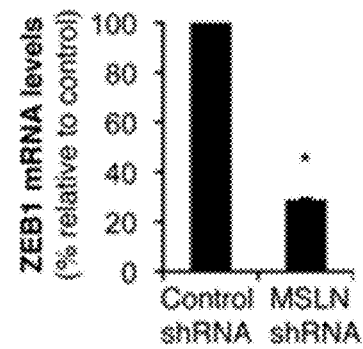
Figure 15C:
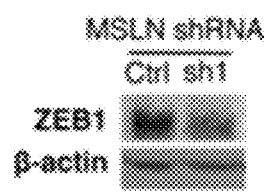
Figure 15D:
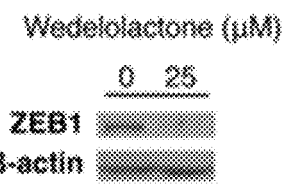
Figure 15E:
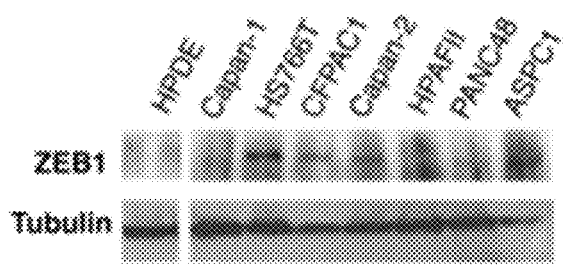
Figure 15F:
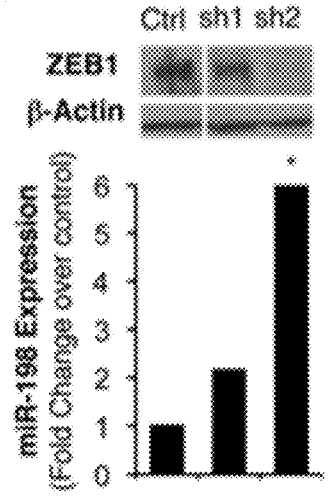
Figure 15G:
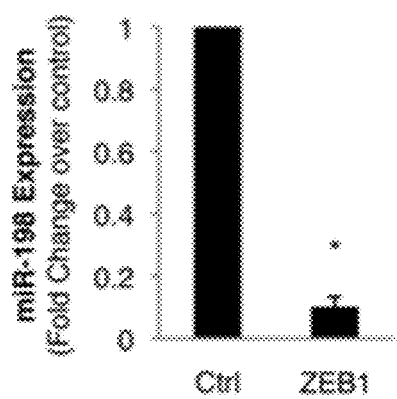

Constitutive NF-κB activation occurs in PC cells in response to MSLN overexpression (Bharadwaj et al., 2011a). OCT-2 transcription is induced by NF-κB activation in B-cells (Liu et al., 1996). It was previously reported that MSLN constitutively activates NF-κB in PC cells (Bharadwaj et al., 2011a; Bharadwaj et al., 2011b). No to be limited, the MSLN-mediated NF-κB activation may be linked to OCT-2 overexpression/miR-198 downregulation. Several binding sites were identified for the NF-κB-inducible repressive transcription factor OCT-2 in the FSTL1/miR-198 promoter, as well as a close association between OCT-2, MSLN, and miR-198 (FIG. 1D). Taken together these findings led to the nonbinding postulate that MSLN-mediated NF-κB activation and subsequent OCT-2 induction might provide a link between MSLN overexpression and miR-198 repression. To test this, MIA-MSLN cells were treated with the NF-κB inhibitor Wedelolactone, and a ~17-fold increase in miR-198 expression was observed when compared to untreated controls (FIG. 2F). That is, wedelolactone treatment restores miR-198 expression in MIA-MSLN cells to pre-MSLN levels. Forced MSLN expression led to a strong induction in OCT-2 expression. While MIA cells had very low endogenous OCT-2 levels, MIA-MSLN cells had high levels of OCT-2 (FIG. 11A). Treatment of MIA-MSLN cells with Wedelolactone led to an almost complete block in OCT-2 expression at both the mRNA and protein levels, indicating that MSLN-mediated NF-κB activation was in fact responsible for the induction of OCT-2 (FIG. 2G). That is, wedelolactone treatment blocks OCT-2 induction in MIA-MSLN cells. These results were also confirmed in endogenously high MSLN cell lines (FIG. 11B).

OCT-2 can function as a repressor or an activator depending on the cell-specific context (Azuara-Liceaga et al., 2004; Dawson et al., 1994; Liu et al., 1996). OCT-2-specific shRNAs were used to knock down OCT-2 expression and to determine whether it was acting as a repressor for miR-198. OCT-2 knockdown results in a 12-fold upregulation of miR-198 expression after 72 h, restoring miR-198 levels close to pre-MSLN expression levels (FIG. 2H). These results demonstrate that OCT-2 overexpression resulting from MSLN-mediated NF-κB activation strongly represses miR-198, and that blocking either NF-κB or OCT-2 in this pathway can effectively restore miR-198 expression.

Example 4

Figure 3B:
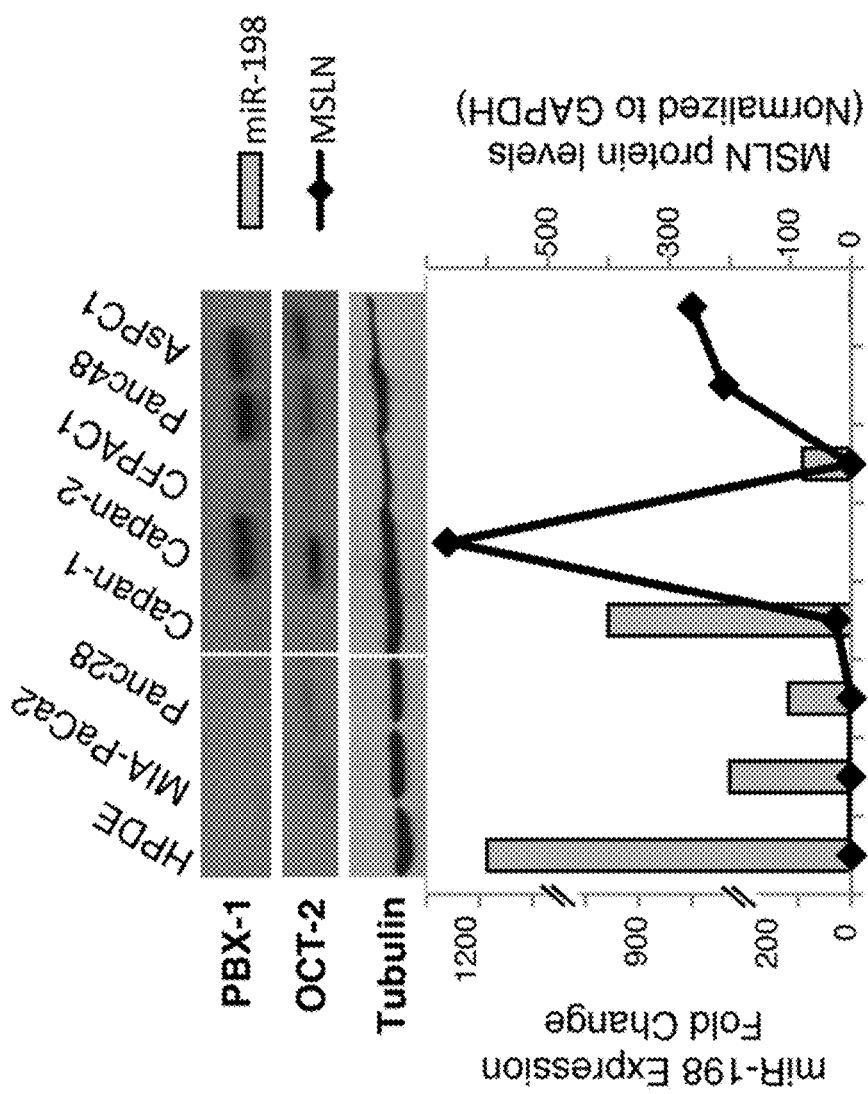
Figure 3C:
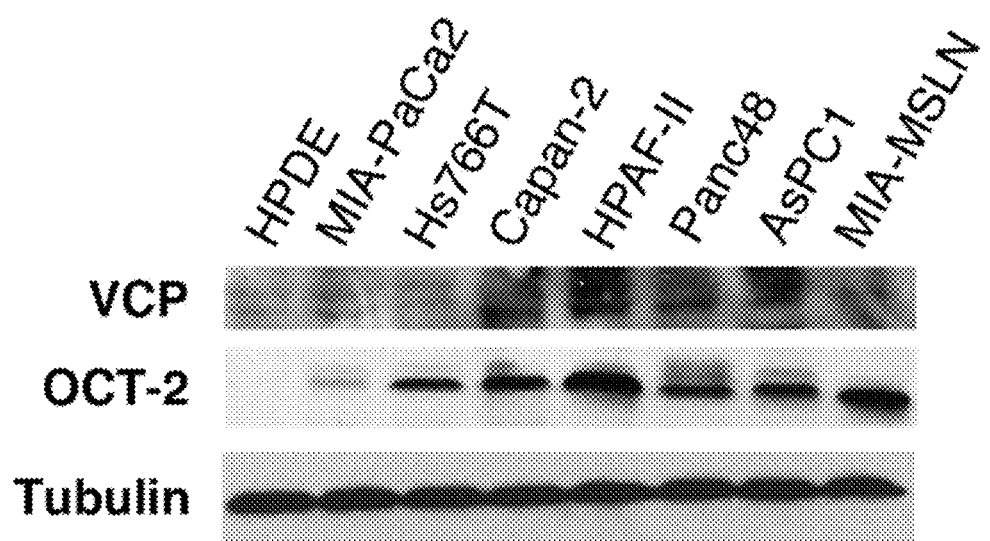
Figure 10E:
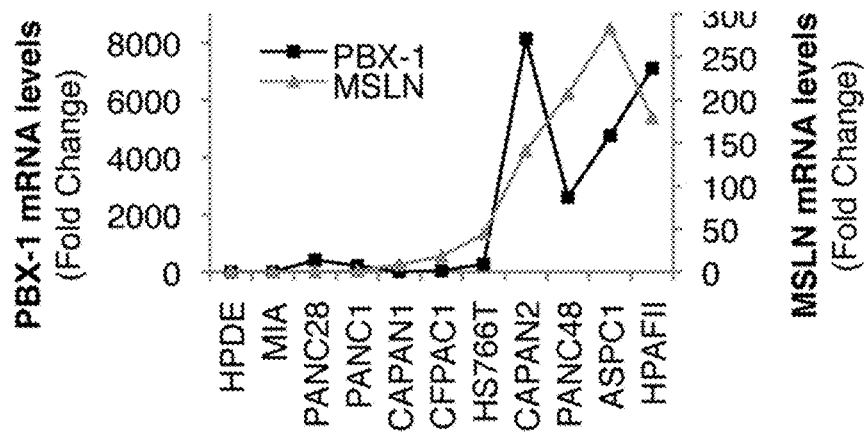
Figure 10F:
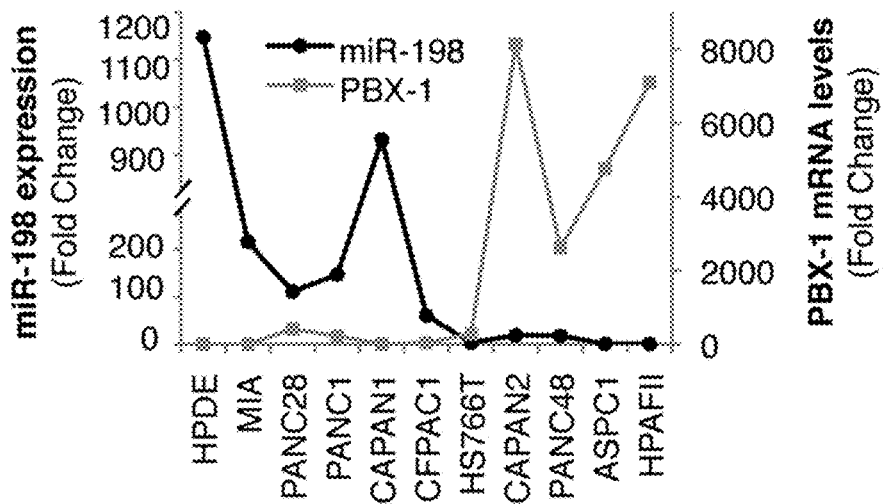

MiR-198 is the Central Link Between Upstream Regulatory Factors MSLN and OCT-2 and the Closely Correlated Downstream PBX-1/VCP Tumorigenic Axis The above studies established correlations between the various factors in the interactome. These relationships were then verified in vitro so that the mechanisms through which these molecules interacted could be further elucidated. A series of western blots were performed in order to demonstrate the link between upstream MSLN and OCT-2 regulators and the downstream PBX-1/VCP axis (FIG. 3A-C). As shown in FIG. 3A, MSLN expression correlated closely with PBX-1 expression ($p<0.05$) and inversely with miR-198 expression in a majority of PC cell lines. The same correlation was confirmed at the mRNA level (FIGS. 10E and 10F).

OCT-2 and PBX-1 expression was next examined in a PC cell line panel. HPDE cells had almost undetectable OCT-2 expression levels, while the majority of PC cell lines had a low level of OCT-2 expression. This is the first report of OCT-2 expression in PC cell lines. Additionally, OCT-2 expression correlated closely with both MSLN expression and PBX-1 expression, with markedly higher OCT-2 expression in most cells with the highest MSLN and PBX-1 levels and low miR-198 levels ($p<0.05$) (FIG. 3B). Lastly, FIG. 3C demonstrates the correlation between OCT-2 and VCP, tying together the last of the factors in the interactome in the PC cell line panel, thereby confirming that the results observed from clinical samples at the mRNA level translate to protein expression with a functional effect.

Figure 3D:
Figure 3E:
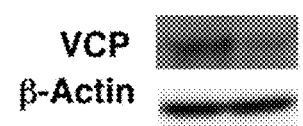
Figure 3F:
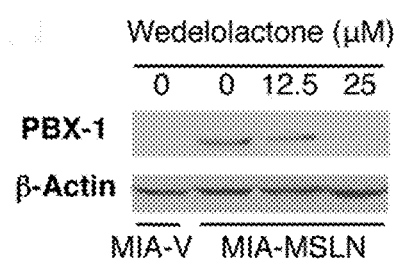
Figure 10G:
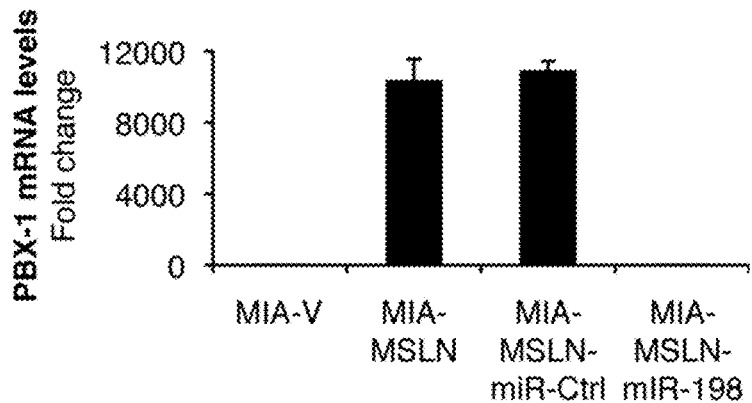
Figure 10H:
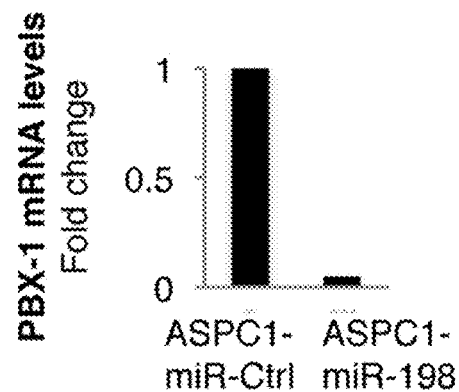
Figure 10I:
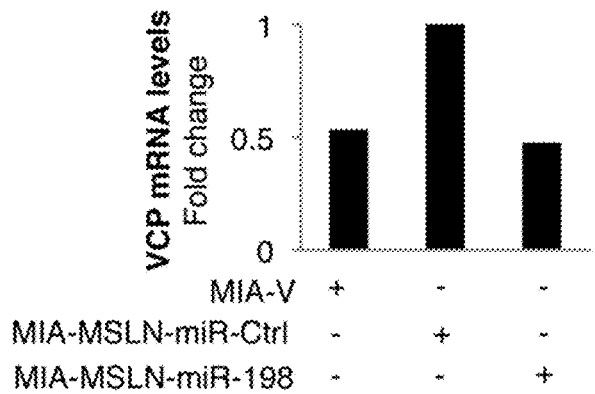

Both PBX-1 and VCP are predicted targets of miR-198, and therefore downstream effectors of the network. To examine this relationship, miR-198 was stably overexpressed in MIA-MSLN cells and AsPC1 cells (FIG. 12). Overexpressing miR-198 in MIA-MSLN or AsPC1 cells led to a decrease in PBX-1 mRNA (FIG. 10G, FIG. 10H) and protein expression (FIG. 3D), making them almost undetectable. A similar result was observed for VCP following miR-198 reconstitution in MIA-MSLN cells; VCP protein expression in MIA-MSLN and AsPC1 cells is reduced following miR-198 overexpression in both cell lines (FIG. 3E and FIG. 10I), although a basal level of expression is still detectable. At the mRNA level, MIA-MSLN cells had a consistent in VCP mRNA levels following miR-198 overexpression (FIGS. 10I and J). These results were tied to the rest of the interactome using either Wedelolactone inhibition of NF-κB (FIG. 3F) or shRNAs against OCT-2 (not shown), both of which led to the downregulation of PBX-1 expression.

Figure 3G:
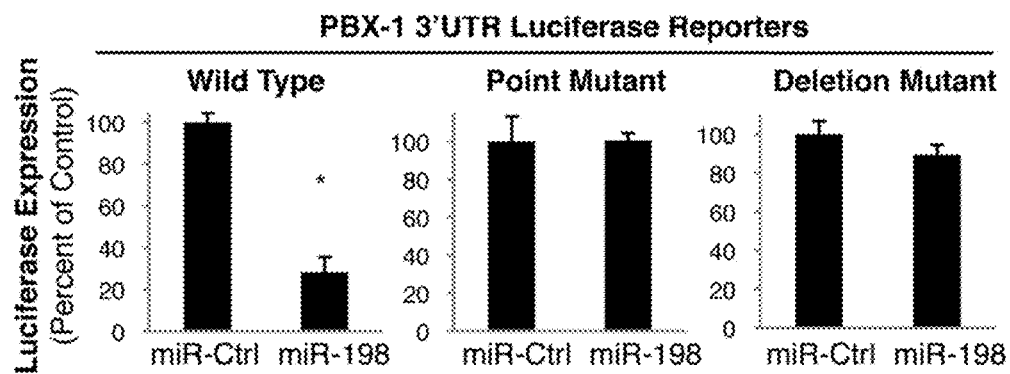
Figure 3H:
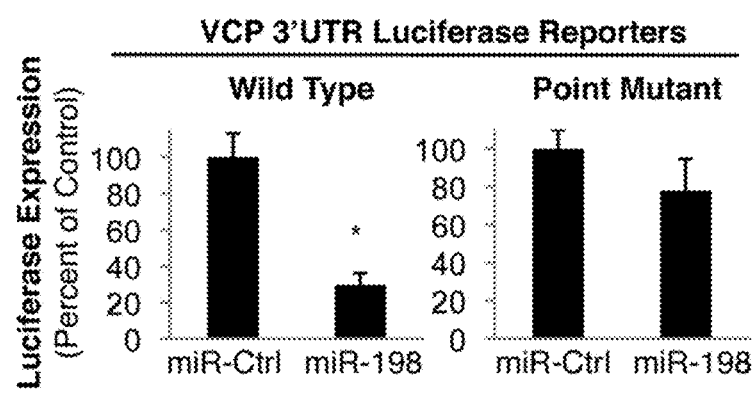

Luciferase reporters and site-directed mutagenesis were used to either delete the entire miR-198 binding site or to insert three point mutations within the miR-198 seed region of both PBX-1 and VCP (FIGS. 10K and L). Dual-luciferase assays showed a 65% reduction in PBX-1 luciferase expression following miR-198 transfection, which was abolished when the target site for miR-198 was either deleted or mutated (FIG. 3G), indicating a direct targeting of miR-198 to the 3'UTR of PBX-1. In the case of VCP, a ~70% decrease in luciferase activity (p<0.05) was partially restored when the seed region was mutated (FIG. 3H).

Example 5

MiR-198 Reciprocally Regulates MSLN Expression by Binding to Target Sites within the MSLN Coding Region (CDS)

Interestingly, miR-198 overexpression in MIA-MSLN cells was observed to lead to an almost complete reduction of MSLN expression at the protein level (FIG. 4A), with a partial decrease in the mRNA expression levels (FIG. 4B), indicating a mechanism of post-transcriptional regulation. This suggests that a reciprocal regulatory loop and feed-forward constitutive activation pathway may exist within the interactome, with MSLN modulating miR-198 through the NF-κB/OCT-2 axis and miR-198 directly regulating MSLN expression.

No putative miR-198 targets were found in the 3'UTR of MSLN using target prediction software. However, while miRNAs typically act on the 3'UTRs of transcripts, recent evidence suggests that miRNAs also act on the 5'UTRs (Lytle et al., 2007) and even within the CDS of genes (Tay et al., 2008). RNA22 was used to search for potential miR-198 binding sites within the CDS of MSLN, and three potential binding sites for miR-198 were found (FIG. 13A). Site-directed mutagenesis was used to alter the nucleotide sequence of the miR-198 binding sites without altering the amino acid composition of the MSLN protein (FIG. 13B), and co-transfected WT or mutant plasmids was transfected along with miR-198 or control precursors into COS-7 cells, chosen because they have undetectable endogenous levels of both MSLN and miR-198 (FIG. 13C). MiR-198 transfection abolished expression of the WT MSLN protein (FIG. 4C). Mutating the three binding sites resulted in differential regulation of MSLN by miR-198. When site 1 was mutated, there was almost no noticeable recovery of MSLN expression. However, mutating site 2 resulted in an almost complete recovery of protein expression, with the expression of the site 3 mutant falling in between the two. Double mutants of sites 1+3 or 1+2 resulted in no noticeable improvement in expression than their single counterparts. However, the site 2+3 double mutant resulted in complete restoration of MSLN expression (FIG. 4C). This indicates that at least two miR-198 binding sites cooperate to block MSLN protein expression.

Figure 4D:
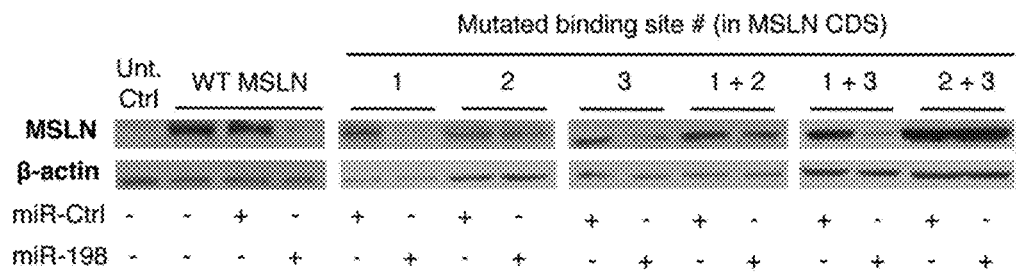
Figure 4E:
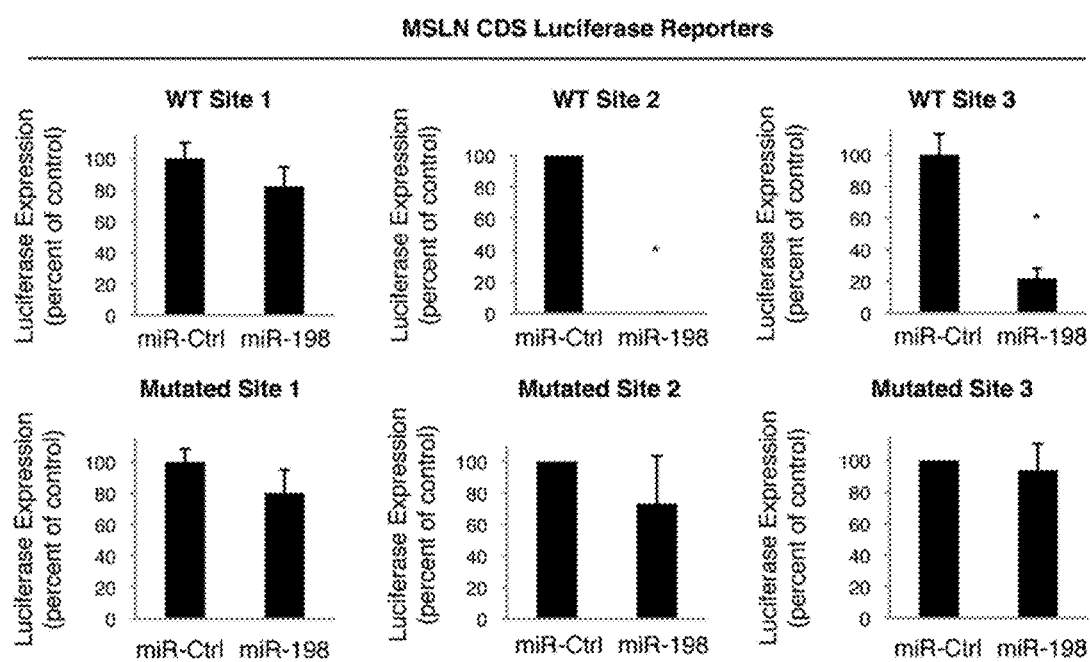

MiR-198 targeting of the MSLN CDS regions was further validated by constructing luciferase reporter constructs containing 600 or 400 bp portions of the MSLN CDS with WT or mutated seed regions (FIG. 13D). Firefly luciferase expression was significantly decreased in two of the WT constructs in the presence of miR-198 (almost completely for site 2, ~70% for site 3, p<0.05), and was restored to control levels in the mutant constructs (FIG. 4D). While a slight reduction was also observed for the site 1 constructs, it was not statistically significant. Mutating the miR-198 binding site failed to recover luciferase expression any further in this construct. RNA22 was used to examine the MSLN gene in several other species, including rats, mice, and monkeys, and it was found that all the species examined had 2 or 3 predicted miR-198 binding sites within the MSLN coding region, despite the overall lack of homology of the MSLN protein with the rodent species (data not shown). Between Homo sapiens and Macaca mulatta, there is a 92% homology between the MSLN proteins. In this case, two of the three sites match identically between the two species: Site 2, which is located at position 916-937 in the human MSLN CDS, is conserved at position 745-766 in the monkey CDS; Site 3, which is located at position 511-532 in the human MSLN CDS, is conserved at position 344-365 in the monkey CDS. Both of these binding sites correspond to the same region in both species based on sequence homology. These results indicate the importance of miR-198 targeting of MSLN in that these sites have been evolutionarily conserved. Taken together, the results show a synergistic effect between at least two sites in the MSLN coding region through which miR-198 can modulate its expression, and that these sites are evolutionarily conserved, underscoring the importance of this regulatory interaction.

Example 6

Figure 5A:
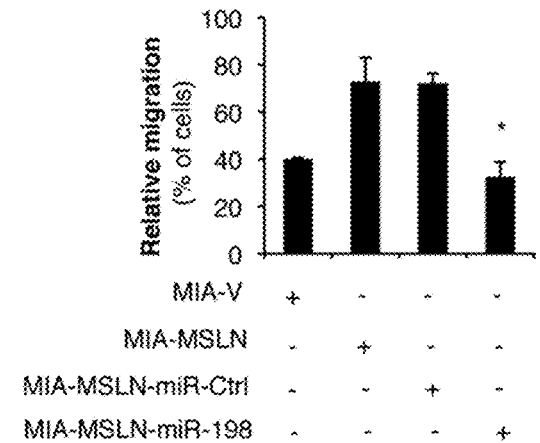
FIGS. 5A-5I illustrate stable miR-198 reconstitution reduces the tumorigenic functions of mesothelin-overexpressing pancreatic cancer cells in vitro.
Figure 5B:
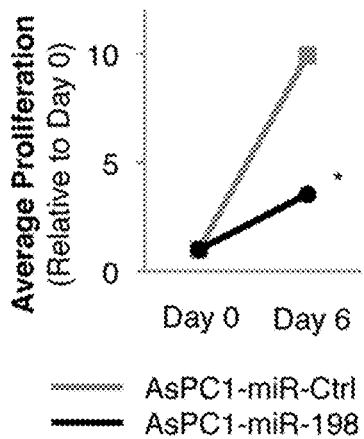
Figure 5C:
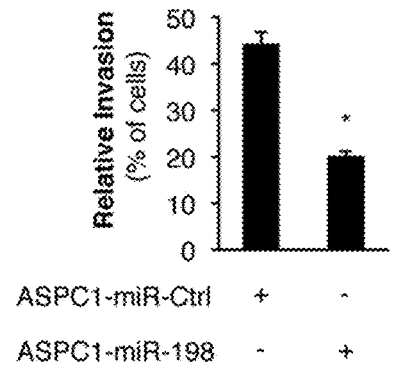
Figure 5D:
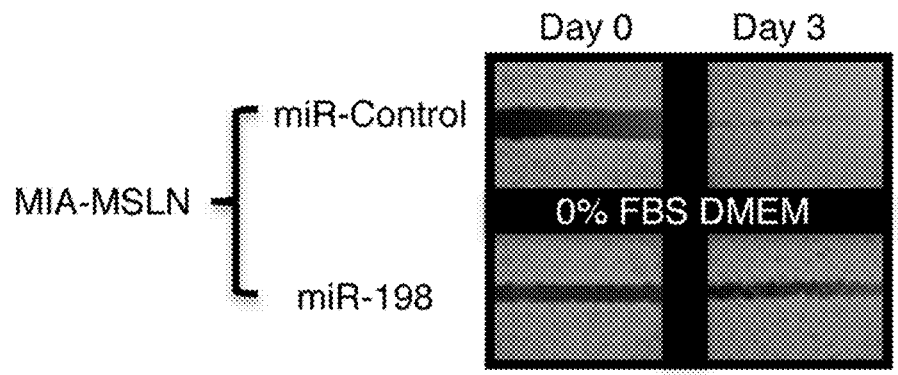

Reconstitution of miR-198 Reduces Tumorigenic Functions of MSLN-Overexpressing Cells In Vitro After demonstrating that miR-198 regulated expression of MSLN, PBX-1, and VCP in PC cells, the functional relevance of miR-198 modulation was examined and functional assays were performed to examine the effects of miR-198 expression on the tumorigenicity of MSLN-overexpressing PC cells. Transient transfection of miR-198 precursors in MIA-MSLN cells led to a significant (p<0.05) decrease in proliferation, and migration of MIA-MSLN cells (FIG. 14A-C). These results were validated by examining the tumorigenic potential of the two lines of miR-198 overexpressing stable cells (MIA-MSLN and AsPC1). After 48 h, migration was reduced by ~40% in MIA-MSLN cells (p<0.05) (FIG. 5A), and by 33% (p<0.05) in AsPC1 cells (FIG. 14D). AsPC1-miR-198 cells had significantly lower proliferation rates than AsPC1-miR-Ctrl cells (FIG. 5B), as did MIA-V and MIA-MSLN-miR-198 cells, which both had approximately 3 fold lower proliferation rates than MIA-MSLN and MIA-MSLN-miR-Ctrl cells after 5 days (p<0.05) (FIG. 14E). Cell invasion was measured across a Matrigel matrix, and observed a similar reduction in migration capacity following miR-198 overexpression (FIG. 5C, FIG. 14F). Monolayer wound healing assays on both MIA-MSLN (FIG. 5D) and AsPC1 cells (FIG. 14G) show a reduced wound closure rate when miR-198 was overexpressed in all the different serum conditions tested.

Figure 5E:
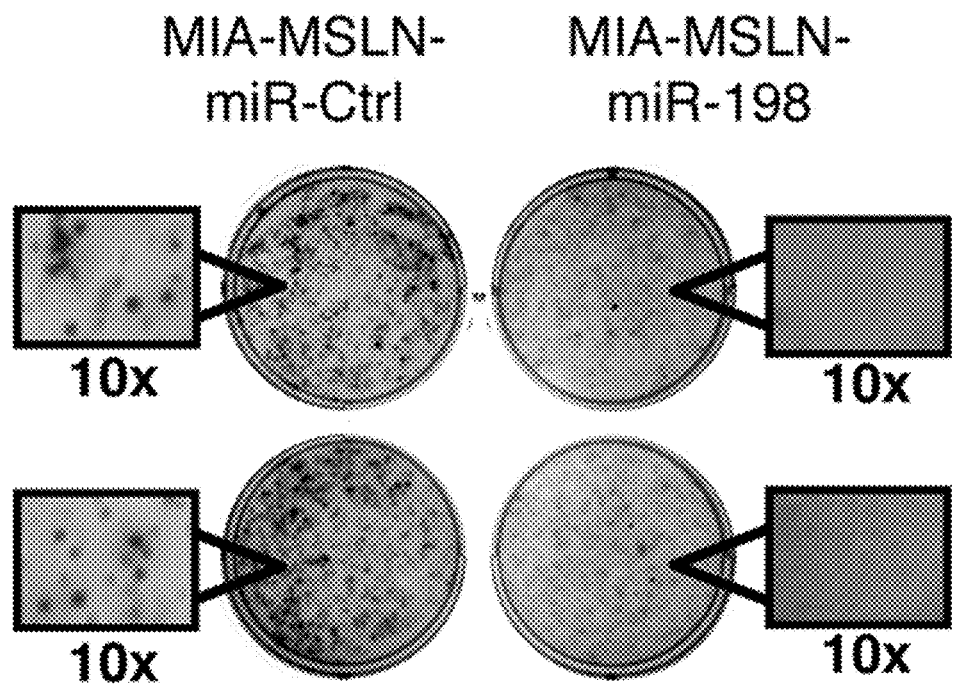

One of the additional hallmarks of MSLN overexpression is that it can confer onto cells the ability for anchorage independent growth in soft agar (Uehara et al., 2008). miR-198 overexpression resulted in a loss of this characteristic. MIA-MSLN cells were able to effectively establish colonies in soft agar after 15 days, while MIA-MSLN-miR-198 plates had very few colonies. ImageJ software was used to analyze the density of colonies appearing on plates, and showed a reduction in mean threshold intensity of almost 20 fold (p<0.05) (FIG. 5E, FIG. 14H).

Figure 5F:
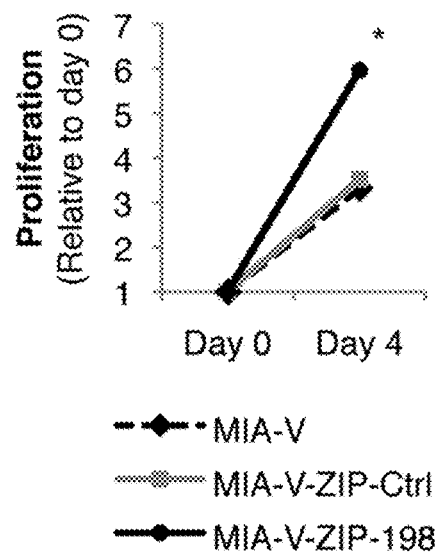
Figure 5G:
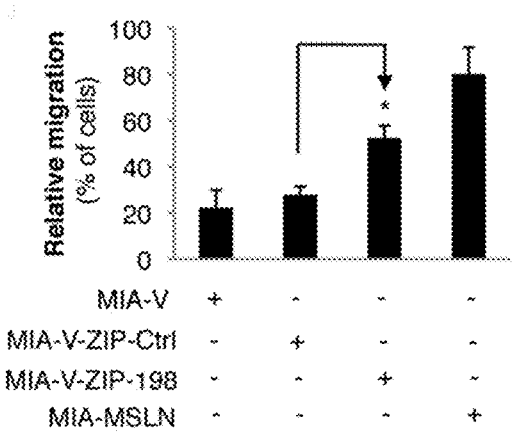

The role of miR-198 in vitro was further examined using an antisense inhibitor of miR-198 (Zip-198) (FIG. 12). Blocking miR-198 in MIA-V cells (MIA-V-Zip-198) led to a significant increase in both proliferation (FIG. 5F) and migration (p<0.05) (FIG. 5G), a result which confirmed in HPDE cells FIG. 14I).

It was previously found that MSLN overexpression results in increased proliferation through activation of Stat3 (Bharadwaj et al., 2008) and increased autocrine stimulation through IL6/sIL6R trans-signaling (Bharadwaj et al., 2011b). At the same time, PBX-1 has been shown to act as a transcription factor in cooperation with homeobox proteins to regulate proliferation and differentiation of both normal cells and cancer cells (Lu et al., 1995; Qiu et al., 2007). PBX-1 has also been implicated in metastasis and invasion (Asai et al., 2002), like MSLN (Li et al., 2008). In order to separate the effects of MSLN signaling from those of PBX-1 in PC cells, PBX-1 was modulated via overexpression or shRNA blocking in respective cell lines, which resulted in a statistically significant yet modest change in proliferation (FIG. 5H, FIG. 14J) when compared to the effects of MSLN modulation (p<0.05) (FIG. 5B), thereby indicating that the MSLN/IL6/Stat3 axis plays more of a role in MSLN-mediated proliferation changes than the MSLN/PBX-1 axis does, although this relationship still contributes to the overall tumorigenesis of PC cells.

Figure 5H:
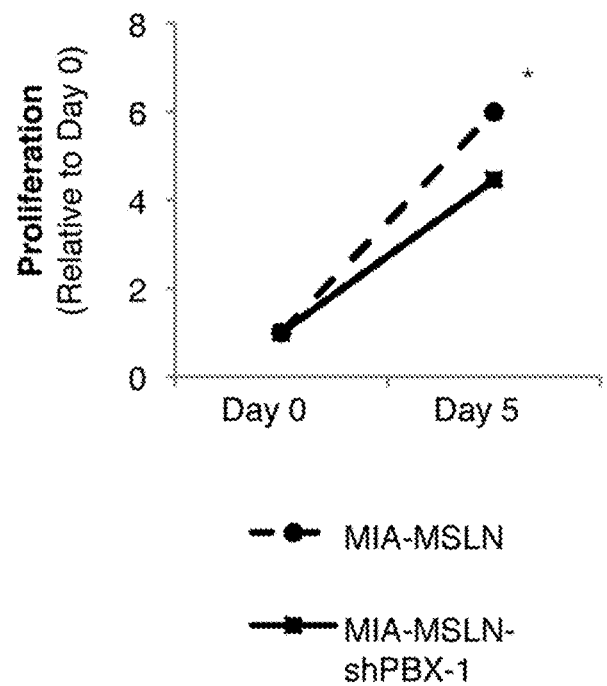
Figure 5I:
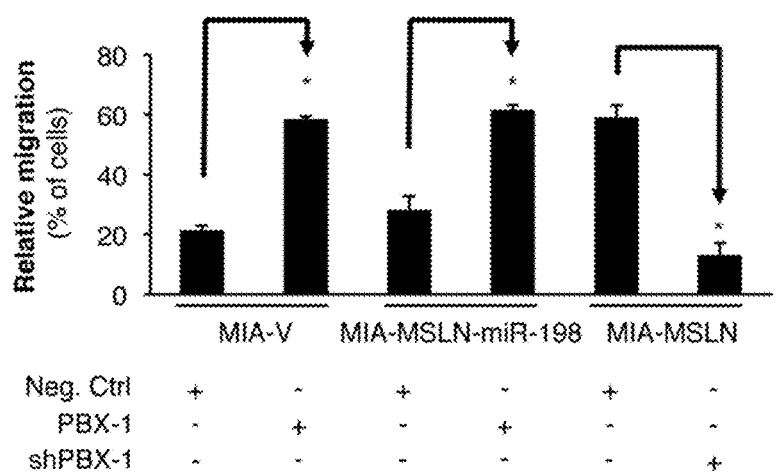

On the other hand, overexpression of PBX-1 in MIA-V or MIA-MSLN-miR-198 cells results in increased migration resembling that observed following MSLN overexpression in MIA-MSLN cells (p<0.05) (FIG. 5I). Conversely, when PBX-1 is blocked with shRNAs in MIA-MSLN cells, the migration of those cells drops to MIA-V levels. This indicates that PBX-1 is primarily responsible for the increased invasiveness that results following MSLN overexpression.

Example 7

MiR-198 Antagonizes the Pro-Survival Effects of MSLN in PC Cells

Figure 6A:
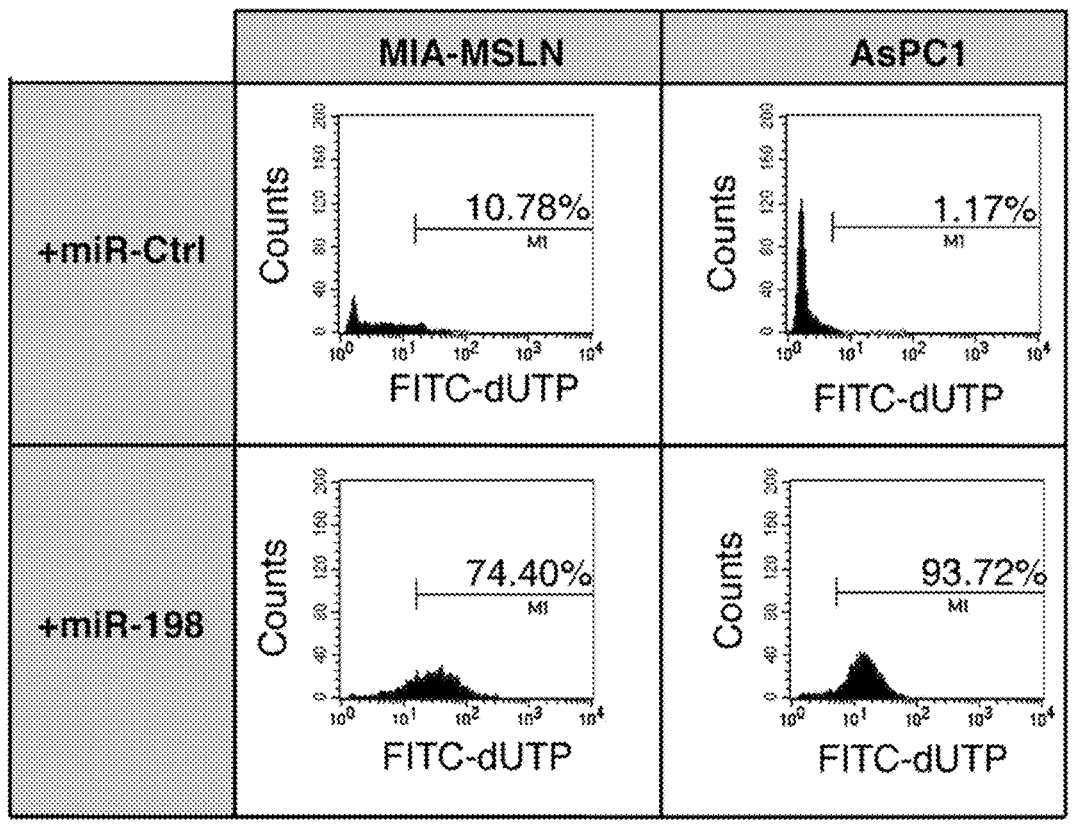
FIGS. 6A-6C illustrate miR-198 is an antagonist of MSLN-mediated autocrine PC cell survival and resistance to TNF-α-induced apoptosis.
Figure 6C:
Figure 6B:
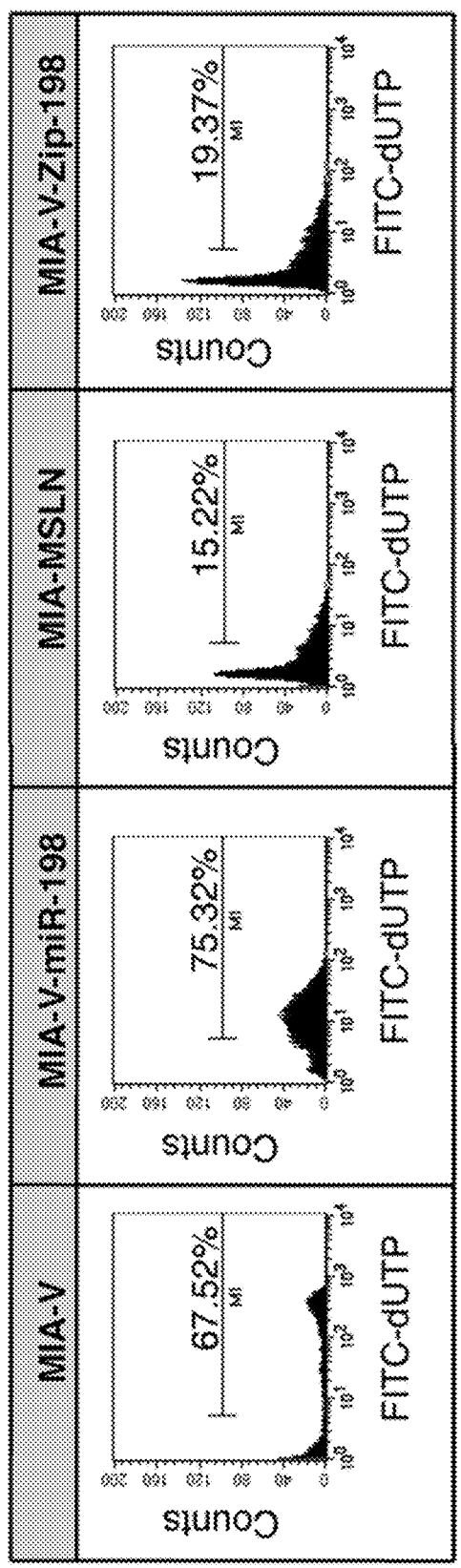

It was previously reported that MSLN overexpression confers resistance to TNF-α-induced apoptosis (Bharadwaj et al., 2011a). To test whether miR-198 mediated modulation of MSLN could reverse this acquired resistance, which would have strong clinical implications, a TUNEL assay was performed in MSLN high cells following TNF-α treatment. After TNF-α treatment, only ~11% of control MIA-MSLN and ~1.2% of AsPC1 cells were undergoing apoptosis as measured by TUNEL. On the other hand, MIA-MSLN-miR-198 and AsPC1-miR-198 cells exposed to the same conditions show a dramatic increase in the number of cells undergoing apoptosis, of >60% and >90% over controls, respectively (FIG. 6A). Conversely, blocking miR-198 expression results in a significant and dramatic drop in the number of apoptotic cells, down to ~19% in MIA-V-Zip-198 cells (FIG. 6B). Further, overexpressing miR-198 in MIA-V cells had a smaller effect in further increasing apoptosis from ~68% to ~75%, consistent with the effects seen on proliferation (FIG. 5H). Apoptosis induction was confirmed through a western blot for caspase 3 activation. The levels of uncleaved caspase 3 decrease in miR-198 high cells (FIG. 6C). These results indicate that miR-198 can antagonize the cell survival effects conferred by MSLN overexpression and its subsequent modulation of downstream targets, implying that miR-198 replacement therapy could potentially reduce MSLN-induced chemotherapeutic resistance.

Example 8

MiR-198 Overexpression Reduces Tumor Growth and Metastatic Spread In Vivo

Figure 7D:
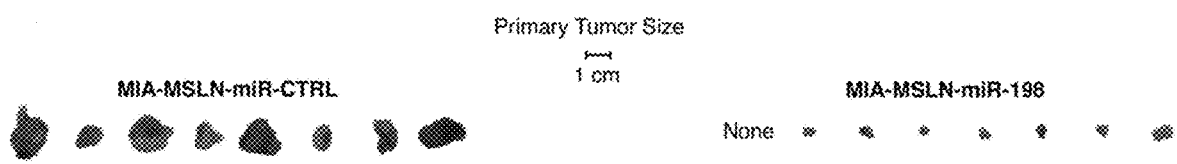

Mouse xenograft models were used to study the effects of miR-198-mediated modulation of the interactome. It was previously reported that MIA-MSLN cells show a dramatic increase in tumor volume compared to MIA-V cells (Li et al., 2008). In accordance with those results, it was found that altering the expression levels of the members of the interactome through miR-198 overexpression resulted in a reduction in tumor volume in two separate mouse models. In a subcutaneous (s.c.) model, 9/9 control mice developed large tumors with rapid onset (measurable at 7 days post injection), with an average tumor volume of 2000 mm$^3$ by time of sacrifice at 25 days post injection (FIG. 7A). In contrast, 6/9 mice injected with miR-198 overexpressing cells showed no signs of tumor development throughout the course of the study, remaining tumor-free for 45 days. The three mice that presented small tumors did not show measurable tumors until day 35 post injection, and by day 45 the tumors had grown to an average volume of only 37 mm$^3$, a highly significant difference compared to the control cell injected mice (p<0.0005) (FIG. 7A). Representative images are shown in FIG. 7B.

Figure 7E:
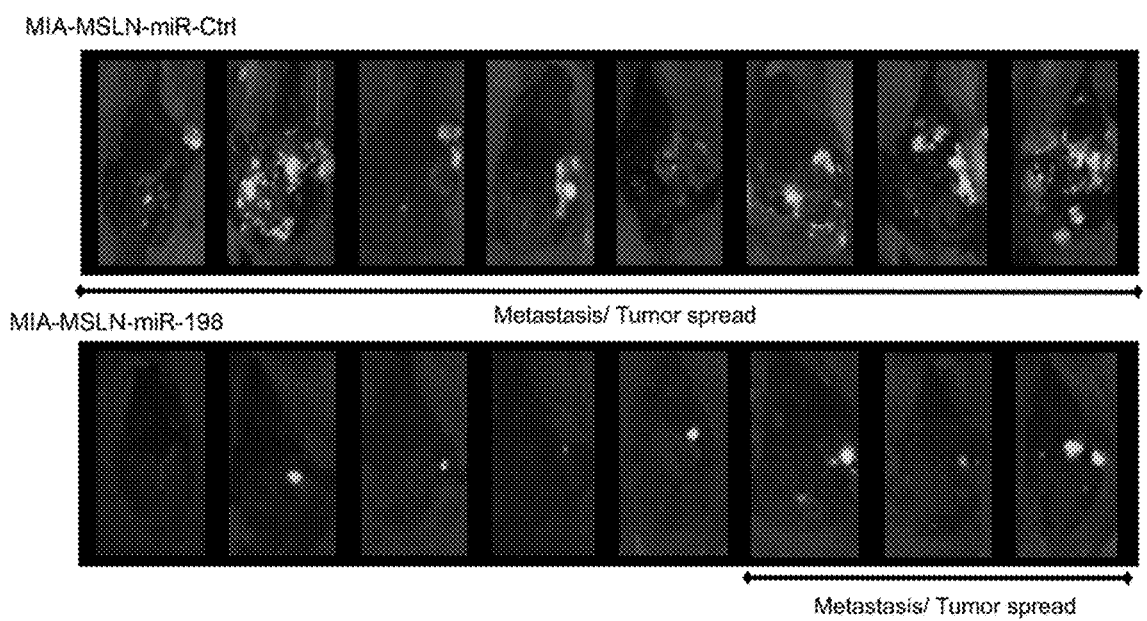

Mice injected orthotopically showed a similar phenotype. All mice injected with MIA-MSLN-miR-Ctrl cells developed primary tumors with an average weight of 0.6 g, ~10 fold greater than primary tumors in mice injected with MIA-MSLN-miR-198 cells, (average weight of 0.06 g) (p<0.0005) (FIGS. 7, C and D). Control mice all had observable jaundice, weight loss, and abdominal ascitic fluid, while none of the mice injected with high miR-198 cells had these symptoms. GFP expression cassettes in stable cells allowed us to visualize the tumor spread in these mice (FIG. 7E). The control mice all presented with liver, spleen, and intestinal metastasis, peritoneal dissemination, and local tumor spread throughout the body cavity. The MIA-MSLN-miR-198 injected mice, on the other hand, had decreased metastases in addition to the decreased primary tumor growth. Four of the eight mice had no metastases; one did not develop any tumor; the remaining 3 mice showed limited tumor spread.

Figure 7F:
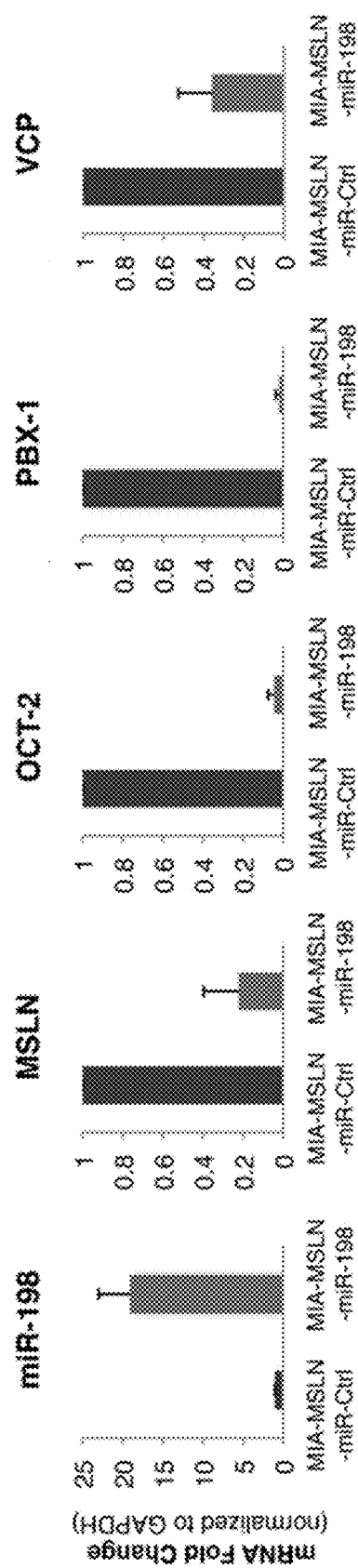

The expression levels were confirmed of the factors in the proposed interactome in the mouse tumor tissues and found that miR-198 overexpression in the smaller, less aggressive MIA-MSLN-miR-198 tumors was accompanied by a significant decrease in expression of the other factors in the network as compared to their levels in the control tumors (p<0.05) (FIG. 7F). These results indicate that PC tumor progression is significantly dampened in vivo following miR-198 reconstitution, likely through modulation of the molecular makeup of the tumors with regards to the interactome.

Example 9

Materials and Methods of Examples 1-8

Cell Culture

Human PC cell lines used in this study were purchased from the ATCC and were authenticated by DNA fingerprinting at the University of Texas MD Anderson Cancer Center Characterized Cell Line Core. HPDE cells were provided from the Ontario Cancer Institute, Canada. All cells were cultured as previously described (Bharadwaj et al., 2008; Li et al., 2008; Li et al., 2007).

Patient Tissue Collection

Human pancreatic adenocarcinoma specimens and adjacent normal tissues were collected from patients who underwent surgery according to an approved human IRB protocol (H-16215) at BCM (Houston, TX) and stored at the Elkins Pancreas Center tissue bank.

Subcutaneous and Orthotopic Pancreatic Cancer Mouse Models

All animal procedures were conducted under the guidelines approved by the Institutional Animal Care and Use Committee (IACUC). Cells ($3 \times 10^6$) were inoculated into the right flank (s.c. model) or into the pancreas (orthotopic model) of 5 to 6-week-old male nude mice (NCI-Charles River) as previously described (Li et al., 2007). Tumor size was measured using a digital caliper and tumor volume was determined with the following formula: tumor volume $(mm^3)$=[length (mm)]×[width (mm)]2×0.52. For the orthotopic model, after 4 weeks all surviving mice were euthanized and evaluated macroscopically for the presence of orthotopic tumor and metastases in the abdominal cavity. Tumor spread was further visualized using a fluorescent filter to view GFP expression. The tumor nodules were explanted, counted, and weighed. Tumor tissues were stored in RNAse Later solution (Ambion) in −80° for subsequent RNA/miRNA isolation and analysis.

Statistical Analysis

Statistical analysis was performed using the Student's t-test (paired, 2-tailed). Statistical significance was defined as $p<0.05$ (denoted by *). Survival data was analyzed using Log-rank test and the data was plotted using the Kaplan-Meier method. Patients still living were censored from the results. Data are presented as mean±SD. Linear regression and correlation analyses were performed using GraphPad Prism (GraphPad Software).

Immunoblotting

Western blots were performed as previously described (Li et al., 2008). Membranes were probed with: anti-MSLN monoclonal antibody (1:1000) (Abcam); PBX-1 polyclonal antibody (1:1000) and Caspase 3 antibody (1:1000) (Cell Signaling); OCT-2 polyclonal antibody (1:400), and VCP polyclonal antibody (1:200) (Santa Cruz Biotechnology); or anti-β-actin, Tubulin, LaminA or GAPDH antibodies (1:10,000) (Sigma Aldrich). Secondary incubation was performed with horseradish peroxidase-linked secondary antibody (1:2,000) (anti-mouse, anti-goat or anti-rabbit) (Cell Signaling).

Cells were lysed in RIPA buffer (Invitrogen) and protease inhibitor cocktail for 30 min in ice. Cell lysates were then collected after centrifugation at 12,000 rpm for 5 min at 4° C. Total protein concentration was quantified using BCA Protein Assay Reagent system (Thermo Scientific). Sixty micrograms of lysate protein was loaded on a 10% SDS-PAGE gel, and total cellular protein was separated and then transblotted overnight at 4° C. onto Hybond-P PVDF membrane (Amersham Biosciences). The membranes were probed with anti-MSLN monoclonal antibody (Abcam) (1:1,000), PBX-1 polyclonal antibody (Cell Signaling) (1:1,000), ZEB1 polyclonal antibody (1:1,000), cyclin T1 antibody (Baylor College of Medicine), Caspase 3 antibody (1:1000) (Cell Signaling), VCP polyclonal antibody (1:200) (Santa Cruz Biotechnology) or anti-3-actin (1:10,000) or GAPDH antibodies (Sigma Aldrich) at 4° C. overnight; washed three times with 0.1% Tween 20-TBS; and incubated in a horseradish peroxidase-linked secondary antibody (1:2,000) (Cell Signaling) for 1 h at room temperature. The membrane was washed three times with 0.1% Tween 20-TBS, and the immunoreactive bands were detected by using enhanced chemiluminescent (ECL) plus reagent kit (Thermo Scientific). Western blots were quantified using ImageJ software (NIH, Bethesda) by comparing the expression of the protein in question to the expression of the loading control.

In Silico Analyses

FSTL1 promoter analyses were performed using CONFAC (Karanam and Moreno, 2004) software and confirmed using TRANSFAC analysis software (Matys et al., 2006). MiR-198 3'UTR target prediction was performed using TargetScan software as previously described (Lewis et al., 2005), and confirmed using PicTar and miRBase software. Conservation of miR-198 binding sites in the PBX-1 and VCP 3'UTRs across species was determined using TargetScan (Friedman et al., 2009). RNA22 (Miranda et al., 2006) was used to predict full-length target sites for miR-198 within the coding region of the MSLN gene. ImageJ software (NIH) (Rasband, 1997-2011) was used to quantify western blot and anchorage independent growth assay images.

The promoter region of FSTL1 was analyzed as follows: FSTL1 accessions/RefSeq ID was used by the web-based computer program Conserved Transcription Factor Binding Site Finder (CONFAC) to get the Mouse orthologs from ENSEMBL Mart databases and the Genomic sequences from the UCSC Genome database. A pairwise BLAST on the Human-Mouse orthologous genes was then conducted to get the conserved parts which were then submitted to the MATCH program. The output from MATCH was consolidated into a set of reports which show the various Conserved Transcription Factor Binding Sites in the promoter regions of the genes, revealing several putative transcription factor binding sites in the sequence analyzed (FIG. 10).

Transient Transfection and Stable Cell Line Selection

Transfections were performed with Lipofectamine 2000 (Invitrogen) according to the manufacturer's instruction. For shRNA transfection experiments, a plasmid encoding MSLN shRNA (TR311377, Origene), OCT-2 shRNA (TF310276) or PBX-1 shRNA (TG310592) and a control plasmid encoding GPF shRNA (TR30003) were used. Transfections with miRNA precursors were performed using siPORT Transfection reagent and either miR-198 or scrambled control precursors (Ambion) according to the manufacturer's instruction.

MSLN-overexpressing stable cells (or empty vector controls) were selected in MIA PaCa-2 cells or HPDE cells (MIA-MSLN, HPDE-MSLN) or vector (MIA-V, HPDE-V) using retrovirus vectors expressing puromycin resistance (Origene) with 0.5 µg/mL of puromycin added into the medium as previously described (Zhang et al.). Stable cells overexpressing miR-198 or vector control were generated in AsPC-1 (AsPC-1-miR-198, AsPC-1-miR-Ctrl), MIA-MSLN (MIA-MSLN-miR-198, MIA-MSLN-miR-Ctrl), MIA-V (MIA-V-miR-198, MIA-V-miR-Ctrl), and HPDE cells (HPDE-miR-198, HPDE-miR-Ctrl) using the Lenti-miR miRNA Precursor Clone Collection (SBI). The miRZip Lentivector collection from SBI was used to stably knock down miR-198 in MIA-PaCa2 (MIA-V-Zip-198, MIA-V-Zip-Ctrl) and HPDE (HPDE-Zip-198, HPDE-Zip-Ctrl) cells.

miRNA and mRNA Extraction and Reverse-Transcription

Total miRNAs of tissues and cultured cells were extracted and purified using mirVana miRNA Isolation kit (Applied Biosystems/Ambion) following the manufacturer's instructions. Five microliters of RNA were directly converted to cDNA with the QuantiMir™ RT System (SBI System Biosciences, Mountain View, CA). Total mRNA was extracted using the RNAqueous RNA Isolation kit (Applied Biosystems/Ambion). Two micrograms of RNA were converted to cDNA using the iQ SYBR Green supermix and iScript cDNA synthesis kits purchased from Bio-Rad.

Real-Time RT-PCR

Differential expression of 95 miRNAs chosen for their potential roles in cancer, cell development, and apoptosis was analyzed by RT-PCR using the QuantiMir System from SBI System Biosciences in both MIA-V and MIA-MSLN cells. The array plate also included the U6 transcript as a normalization signal. cDNAs from different cell lines and tissue samples were mixed with SYBR® Green Mastermix (Bio-Rad Laboratories) plus the universal reverse primer. Specific primers (1 µl) were added to each well of the qPCR plate. The miRNA sequences and primer sequences used in RT-PCR are listed in FIG. 9. Expression levels of each mature miRNA were evaluated using comparative threshold cycle (Ct) method as normalized to that of U6 (2—ΔCt). The expression level of miR-198 was measured in all subsequent experiments using the same method. Real-time RT PCR was performed as previously described for MSLN, ZEB1, PBX-1, and VCP (Li et al., 2008). The primer sequences used are as follows:

```
for human MSLN (s = sense, a = antisense):
                                    [SEQ ID NO. 103]
5'-CTCAACCCAGATGCGTTCTCG-3' (s)
and

[SEQ ID NO. 104]
5'-AGGTCCACATTGGCCTTCGT-3' (a);

for FSTL1:
                                    [SEQ ID NO. 105]
5'-TCAGCATGACAGACCTCCAG-3 (s)
and

[SEQ ID NO. 106]
5'-TCCCAGAAACTCCATCCAAG-3' (a);

for PBX-1:
                                    [SEQ ID NO. 107]
5'-TGAGCGTGCAGTCACTCAATG-3' (s)
and

[SEQ ID NO. 108]
5'-CGAGTCCATCACTGTATCCTCC-3' (a);

for ZEB1:
                                    [SEQ ID NO. 109]
5'-TGCACTGAGTGTGGAAAAGC-3' (s)
and

[SEQ ID NO. 110]
5'-TGGTGATGCTGAAAGAGACG-3' (a).
```

NF-κB Inhibitor Assays

MIA-MSLN and MIA-V control cells were treated with 0, 12.5 or 25 µM of the IKK inhibitor Wedelolactone (Calbiochem). The cells were collected after 72 h and protein, RNA, and miRNA extracts were prepared and assayed accordingly.

Anchorage Independent Growth Assay

A soft agar assay for colony formation was performed by coating 35 mm dishes with a combination of 0.5% base agar and 0.7% top agar. Base agar preparation: 1% LMP Agarose (DNA grade) (Baylor College of Medicine) was melted in 1× incomplete DMEM, microwaved, and cooled to 40° C. in a water bath. Equal volumes of 20% FBS DMEM pre-warmed to 40° C. in water bath were mixed to give 0.5% Agar+10% DMEM, of which 1.5 ml/35 m Petri dish was added and allowed to set at room temperature.

Top agar preparation: 0.7% LMP Agarose (DNA grade) in 1×DMEM was prepared in the same manner as above. Cells were trypsinized and diluted to $0.1 \times 10^6$ cells/ml, in the 20% FBS DMEM; 5,000 cells/dish were plated in duplicate. The plates were then incubated at 37° C. in a humidified incubator for 15 days. Following incubation, the plates were stained with 0.5 ml of 1% MTT for 2 h, and colonies were photographed using a dissecting microscope. Images were analyzed using IMAGEJ software.

Apoptosis Assay

Apoptosis induction was determined using western blotting for Caspase 3 cleavage and confirmed by labeling DNA breaks using a terminal deoxynucleotidyltransferase dUTP nick end labeling (TUNEL) assay with the APO-DIRECT Kit (BD Biosciences) following 96 h of treatment (24 h serum starvation followed by 72 h of treatment with 20 ng/ml of TNF-α). Briefly, cells were plated in either 10% FBS media or serum-starved for 96 h, at which time $1 \times 10^6$ cells were harvested using trypsin-EDTA. After centrifugation, the pellets were washed twice with PBS, then resuspended in 1% paraformaldehyde in PBS and incubated on ice for 45 minutes. After several washes, the cell pellet again was resuspended in PBS/ethanol, incubated on ice for 30 minutes, and stored at −20° C. Cell samples were then pelleted, washed, and resuspended in 50 µL of DNA labeling solution containing a reaction buffer, terminal deoxynucleotidyl transferase enzyme, FITC-labeled deoxyuridine triphosphate nucleotides, and distilled water. After a 60-minute incubation at 37° C., cells were again washed, pelleted, and resuspended in 500 µl of propidium iodine/RNase staining buffer. Samples were then analyzed by flow cytometry (fluorescence-activated cell sorting) using a FACSCalibur (Becton Dickinson, Franklin Lakes, NJ). Data was further analyzed using the software FLOWJOW ver. 6.1.1 (Tree Star Inc.).

Cell Proliferation Assay

Cells were seeded in 96-well plates ($2 \times 10^3$ cells per well) and serum starved for 24 h prior to differential FBS additions. 3-(4,5-Dimethylthiazol-2-yl)-2,5-diphenyltetrazolium bromide (MTT) was used to measure cell proliferation as previously described (Bharadwaj et al., 2011b).

Cell growth was assessed using MTT at 2, 3, 4, 5 and 6 days after releasing from starvation (not all data shown). Briefly, twenty microliters of MTT reagent mixed with 100 µL of growth medium was added to each well and incubated at 37° C. for 2 h. Cells were then lysed overnight using 100 µl of lysis buffer consisting of 20% SDS in 1:1 dimethyl formamide; $H_2O$ solution. Absorbance was recorded at 520 nm with an EL-800 universal microplate reader (Bio-Tek Instruments). Relative proliferation was calculated by dividing the reading by a Day 0 reading taken prior to serum starvation.

Migration, Invasion, and Wound Healing Assays

Cell migration was determined with a modified Boyden chamber assay as described previously (Li et al., 2008). For invasion assays, Matrigel basement membrane matrix (BD Biosciences) was used by adding 100 ul of 1 mg/ml Matrigel to the migration chamber inserts prior to plating of the cells (Li et al., 2008, Bharadwaj).

An invasion assay was performed as described for the migration assay. For invasion, Matrigel basement membrane matrix (BD Biosciences) was used by adding 100 μl of 1 mg/ml Matrigel to the migration chamber inserts prior to plating of the cells.

For wound healing assay, wounds were created in confluent monolayer of cells with a sterile pipette tip in either 0%, 0.2%, 2%, or 5% FBS media, and wound healing was observed within the scrape line at different time points; representative fields for each cell line were photographed (Li et al., 2008, Bharadwaj).

Luciferase Reporter Constructs

For MSLN, six constructs were generated: 400 or 600 bp segments containing the WT sequence or specific 3-nucleotide mutations in the seed region of each miR-198 binding site were synthesized by GenScript and subcloned into the pEZX-MT01 3'UTR construct from Genecopoeia at Xba1 and BamH1 restriction sites such that they were inserted after the luciferase gene (FIG. 10). The same process was used for the VCP reporter constructs containing the full-length VCP 3'UTR (FIG. 10).

A luciferase construct containing the first 491 bases of the PBX-1 3'UTR was purchased from Switchgear Genomics. Two mutant PBX-1 3'UTR reporters were subsequently generated using the Stratagene Quickchange Site-directed Mutagenesis kit, with the WT miR-198 binding site seed region either altered from TCTGGA to AAGCTT (a HindIII restriction site) or deleted entirely (FIG. 10).

Dual-Luciferase Assays

Dual luciferase assays were performed according to the manufacturer's instruction. Luciferase expression analysis was performed at 24 h using the Dual-luciferase kit (Promega) and Sirius Luminometer (Berthold Detection System). Results are presented as the ratio of firefly to *Renilla* luciferase activities, normalized to controls.

PBX-1 Luciferase Reporters

The PBX-1 3'UTR region was cloned into the pSGG-3UTR vector (based on pGL4.11 vector with a MCS added after luciferase) after the reporter gene, firefly luciferase, whose expression is regulated by the SV40 promoter. A separate reporter for *Renilla* luciferase under the control of the CMV promoter was utilized to normalize for transfection efficiency. The identity of the 3'UTR sequence including the predicted miR-198 binding site was confirmed using the following primers: Fwd: CGTGAATTCTCACGGCTTCC [SEQ ID NO. 111], Rev: GCATCACAAATTT-CACAAATAAAGC. [SEQ ID NO. 112]

The mutagenesis reactions were performed using the Stratagene Quickchange Site-directed Mutagenesis kit from Agilent Technologies, according to the manufacturer's instructions. Briefly, Stratagene software was used to generate the following primers introducing the desired mutation or deletion, respectively:

(sense)
[SEQ ID NO. 113]
5'-GGGATGCTATTTCAGCCAAAAGCTTCACTTCTTTATACTCTCTTC-3', (antisense)
[SEQ ID NO. 114]
5'-CCTACGATAAAGTCGGTTTTCGAAGTGAAGAAATATGAGAGAAGG-3', and (sense)
[SEQ ID NO. 115]
5'-CTTCTTTGGGATGCTATTTCAGCCAATACTTCTTTATACTCTC-3', and (antisense)
[SEQ ID NO. 116]
5'-GAGAGTATAAAGAAGTATTGGCTGAAATAGCATCCCAAAGAAG-3'.

PCR amplification of the mutated plasmids was performed according to manufacturer specifications and followed by DpnI digestion of the parental methylated vectors. The plasmids were then transformed into XL-10 Gold ultracompetent cells and plated on LB-Amp plates. Individual colonies were then grown overnight and plasmids were isolated using the QIAPrep Spin Miniprep Kit (QIAGEN) according to the manufacturer's instructions. The plasmids were sequenced to confirm the identity of the nucleotide sequence using the following primers, specific for the 3'UTR cloned sequence in the vector: 5'-CGTGAATTCTCACGGCTTCC-3' (sense) [SEQ ID NO. 117], and 5'-GCATCACAAATTT-CACAAATAAAGC-3' (antisense) [SEQ ID NO. 118].

MSLN CDS Mutant Constructs and Assay

A MSLN ORF clone was purchased from Origene (RC202532). Site-directed mutagenesis was used to generate constructs containing silent mutations in each of the three predicted miR-198 binding sites within the CDS of the MSLN gene (FIG. 13). MiR-198 precursors or a scrambled miRNA control were co-transfected into COS-7 cells along with either the WT MSLN ORF construct or each of the single, double, or triple mutants. Cell lysates were collected for western blot analysis. RNA and miRNA were collected for real-time RT-PCR analysis.

The primers used to generate mutations in each of the three predicted binding sites for miR-198 within the MSLN CDS were as follows:

Site 1:
[SEQ ID NO. 119]
5'-CCTGGACGCCCTCCCACTAGATCTGCTGCTATTCTCA-3' (s)
and
[SEQ ID NO. 120]
3'-GGACCTGCGGGAGGGTGATCTAGACGACGATAAGGAGT-5' (a), Site 2:
[SEQ ID NO. 121]
5'-GCCTGCTGCCCGTGGTAGGACAGCCCATCATCCG-3' (s)
and
[SEQ ID NO. 122]
3'-CGGACGACGGGCACCATCCTGTCGGGTAGTAGGC-5' (a);

Site 3:
[SEQ ID NO. 123]
5'-CGAGTCTGTGATCCAGCACTTAGGATACCTCTTCCTCAAGATGA-3' (s)
and
[SEQ ID NO. 124]
3'-GCTCAGACACTAGGTCGTGAATCCTATGGAGAAGGAGTTCTACT-5' (a);

and corresponded to the regions of the MSLN CDS depicted in supplemental FIG. 13. The PCR conditions and transformations were performed as described above. Double and triple mutants were generated serially, and all mutations were verified by sequencing.

Example 10

Additional in silico analysis also revealed 17 putative binding sites for the negative transcription factor ZEB1 in the miR-198 promoter. ZEB1 is a crucial epithelial-to-mesenchymal transition (EMT) activator in human colorectal and breast cancer (Burk et al), and has been linked to increased EMT and chemoresistance in pancreatic cancers (Wang et al). ZEB1 also directly suppresses transcription of and is involved in a reciprocal regulatory loop with miRNAs in the miR-200 family (Burk et al).

Also examined here was whether ZEB1 was also acting to repress miR-198 expression. While MIA-PaCa2 cells have been previously reported to have a relatively high level of ZEB1 expression (Wellner et al), it is also known that constitutive activation of NF-κB in breast cancer cells and PC cells leads to induction of ZEB1 expression (Maier et al, Chua et al). In accordance with these previous findings, here it was found that ZEB1 is further induced in MIA-PaCa2 cells as a result of MSLN overexpression (FIG. III.3-A). Transfecting MSLN-specific shRNAs in MIA-MSLN cells led to reduced expression of ZEB1 both at the mRNA level (70% reduction) ($p<0.05$) (FIG. B) and at the protein level (~50% reduction) (FIG. C). The involvement of NF-κB activation in ZEB1 induction was confirmed using Wedelolactone, which completely blocked ZEB1 expression in MIA-MSLN cells (FIG. D). In an embodiment of the disclosure, ZEB1 might be contributing to miR-198 repression, and overexpression of ZEB1 in PC cells may contribute to the decrease in miR-198 expression from that of normal tissues. At a certain threshold level, such as that induced through MSLN overexpression, ZEB1 levels become sufficient to completely repress miR-198 expression. Consistent with this, immortalized HPDE control cells, which have the highest miR-198 levels (FIG. III-1-C), have no detectable ZEB1 expression (FIG. E). Furthermore, miR-NAs in the miR-200 family previously reported to be downregulated by ZEB1, including miR-141 and miR-200c (Burk et al) were in fact further downregulated following MSLN overexpression in MIA-MSLN cells from the already repressed levels of MIA-V cells (FIG. A), indicating that the upregulation of ZEB1 did have further strong functional effects even in these highly expressing ZEB1 cells. To confirm the regulatory effects of ZEB1 expression on miR-198 levels, ZEB1-specific shRNAs were transfected into MIA-MSLN cells, which resulted in a partial, ~6.5 fold increase in miR-198 expression compared to controls. Cells transfected with a less effective shRNA that showed only a partial reduction in ZEB1 protein expression also showed a partial (2-fold) increase in miR-198 expression (FIG. F). Conversely, further overexpressing ZEB1 in MIA-PaCa2 cells reduced miR-198 expression ~9 fold ($p<0.05$) (FIG. III.3-G). While the above results implicated ZEB1 in the regulation of miR-198, ZEB1 modulation appeared to only partially recapitulate the effects of NF-κB or MSLN modulation on miR-198, with only a ~6.5 fold increase in miR-198 expression after ZEB1 modulation compared to a ~12-18-fold change through MSLN or NF-κB modulation. Furthermore, some PC cell lines with high MSLN and low miR-198 levels, such as HPAF-II and BxPC3, have been previously reported to have low ZEB1 expression levels (Wellner et all), indicating that MSLN-mediated ZEB1 induction may only be occurring in certain cell lines, and that, while ZEB1 can in certain cases repress miR-198, other mechanisms of MSLN-mediated miR-198 repression may play important roles. ZEB1 may therefore contribute along with OCT-2 as a repressor of miR-198.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

The following references, to the extent that they provide exemplary procedural or other details supplementary to those set forth herein, are specifically incorporated herein by reference.

Argani, P., Iacobuzio-Donahue, C., Ryu, B., Rosty, C., Goggins, M., Wilentz, R. E., Murugesan, S. R., Leach, S. D., Jaffee, E., Yeo, C. J., et al. (2001). Mesothelin is overexpressed in the vast majority of ductal adenocarcinomas of the pancreas: identification of a new pancreatic cancer marker by serial analysis of gene expression (SAGE). Clin Cancer Res 7, 3862-3868.

Asahara, H., Dutta, S., Kao, H. Y., Evans, R. M., and Montminy, M. (1999). Pbx-Hox heterodimers recruit coactivator-corepressor complexes in an isoform-specific manner. Mol Cell Biol 19, 8219-8225.

Asai, T., Tomita, Y., Nakatsuka, S., Hoshida, Y., Myoui, A., Yoshikawa, H., and Aozasa, K. (2002). VCP (p97) regulates NFkappaB signaling pathway, which is important for metastasis of osteosarcoma cell line. Jpn J Cancer Res 93, 296-304.

Azuara-Liceaga, E., Sandoval, M., Corona, M., Gariglio, P., and Lopez-Bayghen, E. (2004). The human involucrin gene is transcriptionally repressed through a tissue-specific silencer element recognized by October-2. Biochem Biophys Res Commun 318, 361-371.

Bargou, R. C., Leng, C., Krappmann, D., Emmerich, F., Mapara, M. Y., Bommert, K., Royer, H. D., Scheidereit, C., and Dorken, B. (1996). High-level nuclear NF-kappa B and OCT-2 is a common feature of cultured Hodgkin/Reed-Sternberg cells. Blood 87, 4340-4347.

Bharadwaj, U., Li, M., Chen, C., and Yao, Q. (2008). Mesothelin-induced pancreatic cancer cell proliferation involves alteration of cyclin E via activation of signal transducer and activator of transcription protein 3. Mol Cancer Res 6, 1755-1765.

Bharadwaj, U., Marin-Muller, C., Li, M., Chen, C., and Yao, Q. (2011a). Mesothelin confers pancreatic cancer cell resistance to TNF-alpha-induced apoptosis through Akt/PI3K/NF-kappaB activation and IL-6/Mcl-1 overexpression. Mol Cancer 10, 106.

Bharadwaj, U., Marin-Muller, C., Li, M., Chen, C., and Yao, Q. (2011b). Mesothelin Overexpression Promotes Autocrine IL-6/sIL-6R Trans-signaling to stimulate Pancreatic Cancer Cell Proliferation. Carcinogenesis.

Bloomston, M., Frankel, W. L., Petrocca, F., Volinia, S., Alder, H., Hagan, J. P., Liu, C. G., Bhatt, D., Taccioli, C., and Croce, C. M. (2007). MicroRNA expression patterns to differentiate pancreatic adenocarcinoma from normal pancreas and chronic pancreatitis. JAMA 297, 1901-1908.

Bonnet, E., Michoel, T., and Van de Peer, Y. (2010). Prediction of a gene regulatory network linked to prostate cancer from gene expression, microRNA and clinical data. Bioinformatics 26, i638-644.

Cullen, B. R. (2004). Transcription and processing of human microRNA precursors. Molecular cell 16, 861-865.

Dawson, S. J., Yoon, S. O., Chikaraishi, D. M., Lillycrop, K. A., and Latchman, D. S. (1994). The OCT-2 transcription factor represses tyrosine hydroxylase expression via a heptamer TAATGARAT-like motif in the gene promoter. Nucleic Acids Res 22, 1023-1028.

Dutta, S., Gannon, M., Peers, B., Wright, C., Bonner-Weir, S., and Montminy, M. (2001). PDX:PBX complexes are required for normal proliferation of pancreatic cells during development. Proceedings of the National Academy of Sciences of the United States of America 98, 1065-1070.

Friedl, E. M., and Matthias, P. (1995). Transcriptional activation and repression, two properties of the lymphoid-specific transcription factor October-2a. Eur J Biochem 234, 308-316.

Garofalo, M., Di Leva, G., Romano, G., Nuovo, G., Suh, S. S., Ngankeu, A., Taccioli, C., Pichiorri, F., Alder, H., Secchiero, P., et al. (2009). miR-221&222 regulate TRAIL resistance and enhance tumorigenicity through PTEN and TIMP3 downregulation. Cancer Cell 16, 498-509.

Hartwell, L. H., Hopfield, J. J., Leibler, S., and Murray, A. W. (1999). From molecular to modular cell biology. Nature 402, C47-52.

Heckman, C. A., Duan, H., Garcia, P. B., and Boxer, L. M. (2006). October transcription factors mediate t(14;18) lymphoma cell survival by directly regulating bcl-2 expression. Oncogene 25, 888-898.

Jemal, A., Siegel, R., Xu, J., and Ward, E. (2010). Cancer statistics, 2010. C A Cancer J Clin 60, 277-300.

Kota, J., Chivukula, R. R., O'Donnell, K. A., Wentzel, E. A., Montgomery, C. L., Hwang, H. W., Chang, T. C., Vivekanandan, P., Torbenson, M., Clark, K. R., et al. (2009). Therapeutic microRNA delivery suppresses tumorigenesis in a murine liver cancer model. Cell 137, 1005-1017.

Li, M., Bharadwaj, U., Zhang, R., Zhang, S., Mu, H., Fisher, W. E., Brunicardi, F. C., Chen, C., and Yao, Q. (2008). Mesothelin is a malignant factor and therapeutic vaccine target for pancreatic cancer. Molecular cancer therapeutics 7, 286-296.

Li, M., Zhang, Y., Liu, Z., Bharadwaj, U., Wang, H., Wang, X., Zhang, S., Liuzzi, J. P., Chang, S. M., Cousins, R. J., et al. (2007). Aberrant expression of zinc transporter ZIP4 (SLC39A4) significantly contributes to human pancreatic cancer pathogenesis and progression. Proceedings of the National Academy of Sciences of the United States of America 104, 18636-18641.

Liu, Y. Z., Dawson, S. J., Gerster, T., Friedl, E., Pengue, G., Matthias, P., Lania, L., and Latchman, D. S. (1996). The ability of the inhibitory domain of the POU family transcription factor OCT-2 to interfere with promoter activation by different classes of activation domains is dependent upon the nature of the basal promoter elements. J Biol Chem 271, 20853-20860.

Lu, Q., Knoepfler, P. S., Scheele, J., Wright, D. D., and Kamps, M. P. (1995). Both Pbx1 and E2A-Pbx1 bind the DNA motif ATCAATCAA cooperatively with the products of multiple murine Hox genes, some of which are themselves oncogenes. Mol Cell Biol 15, 3786-3795.

Lytle, J. R., Yario, T. A., and Steitz, J. A. (2007). Target mRNAs are repressed as efficiently by microRNA-binding sites in the 5' UTR as in the 3' UTR. Proceedings of the National Academy of Sciences of the United States of America 104, 9667-9672.

Muminova, Z. E., Strong, T. V., and Shaw, D. R. (2004). Characterization of human mesothelin transcripts in ovarian and pancreatic cancer. BMC cancer 4, 19.

Park, J. T., Shih Ie, M., and Wang, T. L. (2008). Identification of Pbx1, a potential oncogene, as a Notch3 target gene in ovarian cancer. Cancer Res 68, 8852-8860.

Pileri, S. A., Gaidano, G., Zinzani, P. L., Falini, B., Gaulard, P., Zucca, E., Pieri, F., Berra, E., Sabattini, E., Ascani, S., et al. (2003). Primary mediastinal B-cell lymphoma: high frequency of BCL-6 mutations and consistent expression of the transcription factors OCT-2, BOB.1, and PU.1 in the absence of immunoglobulins. Am J Pathol 162, 243-253.

Qiu, Y., Tomita, Y., Zhang, B., Nakamichi, I., Morii, E., and Aozasa, K. (2007). Pre-B-cell leukemia transcription factor 1 regulates expression of valosin-containing protein, a gene involved in cancer growth. Am J Pathol 170, 152-159.

Rodriguez, A., Griffiths-Jones, S., Ashurst, J. L., and Bradley, A. (2004). Identification of mammalian microRNA host genes and transcription units. Genome research 14, 1902-1910.

Shiraishi, K., Yamasaki, K., Nanba, D., Inoue, H., Hanakawa, Y., Shirakata, Y., Hashimoto, K., and Higashiyama, S. (2007). Pre-B-cell leukemia transcription factor 1 is a major target of promyelocytic leukemia zinc-finger-mediated melanoma cell growth suppression. Oncogene 26, 339-348.

Tan, S., Li, R., Ding, K., Lobie, P. E., and Zhu, T. (2011). miR-198 inhibits migration and invasion of hepatocellular carcinoma cells by targeting the HGF/c-MET pathway. FEBS Lett.

Tay, Y., Zhang, J., Thomson, A. M., Lim, B., and Rigoutsos, I. (2008). MicroRNAs to Nanog, October4 and Sox2 coding regions modulate embryonic stem cell differentiation. Nature 455, 1124-1128.

Tsujimoto, Y., Tomita, Y., Hoshida, Y., Kono, T., Oka, T., Yamamoto, S., Nonomura, N., Okuyama, A., and Aozasa, K. (2004). Elevated expression of valosin-containing protein (p97) is associated with poor prognosis of prostate cancer. Clin Cancer Res 10, 3007-3012.

Uehara, N., Matsuoka, Y., and Tsubura, A. (2008). Mesothelin promotes anchorage-independent growth and prevents anoikis via extracellular signal-regulated kinase signaling pathway in human breast cancer cells. Mol Cancer Res 6, 186-193.

Varnholt, H., Drebber, U., Schulze, F., Wedemeyer, I., Schirmacher, P., Dienes, H. P., and Odenthal, M. (2008). MicroRNA gene expression profile of hepatitis C virus-associated hepatocellular carcinoma. Hepatology 47, 1223-1232.

Wang, J. X., Jiao, J. Q., Li, Q., Long, B., Wang, K., Liu, J. P., Li, Y. R., and Li, P. F. (2011). miR-499 regulates mitochondrial dynamics by targeting calcineurin and dynamin-related protein-1. Nat Med 17, 71-78.

Wang, Q., Song, C., and Li, C. C. (2004). Molecular perspectives on p97-VCP: progress in understanding its structure and diverse biological functions. J Struct Biol 146, 44-57.

Yamamoto, S., Tomita, Y., Hoshida, Y., Iizuka, N., Kidogami, S., Miyata, H., Takiguchi, S., Fujiwara, Y., Yasuda, T., Yano, M., et al. (2004a). Expression level of valosin-containing protein (p97) is associated with prognosis of esophageal carcinoma. Clin Cancer Res 10, 5558-5565.

Yamamoto, S., Tomita, Y., Hoshida, Y., Iizuka, N., Monden, M., Iuchi, K., and Aozasa, K. (2004b). Expression level of valosin-containing protein (p97) is correlated with progression and prognosis of non-small-cell lung carcinoma. Ann Surg Oncol 11, 697-704.

Yamamoto, S., Tomita, Y., Hoshida, Y., Nagano, H., Dono, K., Umeshita, K., Sakon, M., Ishikawa, O., Ohigashi, H., Nakamori, S., et al. (2004c). Increased expression of valosin-containing protein (p97) is associated with lymph node metastasis and prognosis of pancreatic ductal adenocarcinoma. Ann Surg Oncol 11, 165-172.

Yamamoto, S., Tomita, Y., Hoshida, Y., Toyosawa, S., Inohara, H., Kishino, M., Kogo, M., Nakazawa, M., Murakami, S., Iizuka, N., et al. (2004d). Expression level of valosin-containing protein (VCP) as a prognostic marker for gingival squamous cell carcinoma. Ann Oncol 15, 1432-1438.

Yamamoto, S., Tomita, Y., Nakamori, S., Hoshida, Y., Iizuka, N., Okami, J., Nagano, H., Dono, K., Umeshita, K., Sakon, M., et al. (2004e). Valosin-containing protein (p97) and Ki-67 expression is a useful marker in detecting malignant behavior of pancreatic endocrine neoplasms. Oncology 66, 468-475.

Zhang, Y., Bharadwaj, U., Logsdon, C. D., Chen, C., Yao, Q., and Li, M. (2010). ZIP4 regulates pancreatic cancer cell growth by activating IL-6/STAT3 pathway through zinc finger transcription factor CREB. Clin Cancer Res 16, 1423-1430.

Zhang, Y., Li, M., Wang, H., Fisher, W. E., Lin, P. H., Yao, Q., and Chen, C. (2009). Profiling of 95 microRNAs in pancreatic cancer cell lines and surgical specimens by real-time PCR analysis. World journal of surgery 33, 698-709.

Bharadwaj, U., Li, M., Chen, C., and Yao, Q. (2008). Mesothelin-induced pancreatic cancer cell proliferation involves alteration of cyclin E via activation of signal transducer and activator of transcription protein 3. Mol Cancer Res 6, 1755-1765.

Bharadwaj, U., Marin-Muller, C., Li, M., Chen, C., and Yao, Q. (2011a). Mesothelin confers pancreatic cancer cell resistance to TNF-alpha-induced apoptosis through Akt/PI3K/NF-kappaB activation and IL-6/Mcl-1 overexpression. Mol Cancer 10, 106.

Friedman, R. C., Farh, K. K., Burge, C. B., and Bartel, D. P. (2009). Most mammalian mRNAs are conserved targets of microRNAs. Genome research 19, 92-105.

Karanam, S., and Moreno, C. S. (2004). CONFAC: automated application of comparative genomic promoter analysis to DNA microarray datasets. Nucleic Acids Res 32, W475-484.

Katoh, Y., and Katoh, M. (2007). Conserved POU-binding site linked to SP1-binding site within FZD5 promoter: Transcriptional mechanisms of FZD5 in undifferentiated human ES cells, fetal liver/spleen, adult colon, pancreatic islet, and diffuse-type gastric cancer. Int J Oncol 30, 751-755.

Lewis, B. P., Burge, C. B., and Bartel, D. P. (2005). Conserved seed pairing, often flanked by adenosines, indicates that thousands of human genes are microRNA targets. Cell 120, 15-20.

Li, M., Bharadwaj, U., Zhang, R., Zhang, S., Mu, H., Fisher, W. E., Brunicardi, F. C., Chen, C., and Yao, Q. (2008). Mesothelin is a malignant factor and therapeutic vaccine target for pancreatic cancer. Molecular cancer therapeutics 7, 286-296.

Li, M., Bharadwaj, U., Zhang, R., Zhang, S., Mu, H., Fisher, W. E., Brunicardi, F. C., Chen, C., and Yao, Q. (2008). Mesothelin is a malignant factor and therapeutic vaccine target for pancreatic cancer. Molecular cancer therapeutics 7, 286-296.

Matys, V., Kel-Margoulis, O. V., Fricke, E., Liebich, I., Land, S., Barre-Dirrie, A., Reuter, I., Chekmenev, D., Krull, M., Hornischer, K., et al. (2006). TRANSFAC and its module TRANSCompel: transcriptional gene regulation in eukaryotes. Nucleic Acids Res 34, D108-110.

Miranda, K. C., Huynh, T., Tay, Y., Ang, Y. S., Tam, W. L., Thomson, A. M., Lim, B., and Rigoutsos, I. (2006). A pattern-based method for the identification of MicroRNA binding sites and their corresponding heteroduplexes. Cell 126, 1203-1217.

Rasband, W. S. (1997-2011). ImageJ. National Institutes of Health, Bethesda, Maryland, USA.

Burk U, Schubert J, Wellner U, et al. A reciprocal repression between ZEB1 and members of the miR-200 family promotes EMT and invasion in cancer cells. EMBO reports 2008; 9:582-9.

Wang Z, Li Y, Kong D, et al. Acquisition of epithelial-mesenchymal transition phenotype of gemcitabine-resistant pancreatic cancer cells is linked with activation of the notch signaling pathway. Cancer research 2009; 69:2400-7.

Wellner U, Schubert J, Burk U C, et al. The EMT-activator ZEB1 promotes tumorigenicity by repressing stemness-inhibiting microRNAs. Nat Cell Biol 2009; 11:1487-95.

Chua H L, Bhat-Nakshatri P, Clare S E, Morimiya A, Badve S, Nakshatri H. NF-kappaB represses E-cadherin expression and enhances epithelial to mesenchymal transition of mammary epithelial cells: potential involvement of ZEB-1 and ZEB-2. Oncogene 2007; 26:711-24.

Maier H J, Schmidt-Strassburger U, Huber M A, Wiedemann E M, Beug H, Wirth T. NF-kappaB promotes epithelial-mesenchymal transition, migration and invasion of pancreatic carcinoma cells. Cancer Lett; 295:214-28.

What is claimed is:

1. A method of treating cancer in an individual, comprising the step of delivering to the individual an effective amount of an agent that increases the level of microRNA-198 molecules in cancer cells of the individual, wherein the cancer is of the stomach or bone.

2. The method of claim 1, wherein agent upregulates microRNA-198.

3. The method of claim 1, wherein agent comprises microRNA-198, a microRNA-198 mimic, or a modified microRNA-198.

4. The method of claim 3, wherein the composition is administered by a viral vector, a non-viral vector or a combination thereof.

5. The method of claim 3, wherein the composition is administered locally, systemically, or a combination thereof.

6. The method of claim 3, wherein the composition is administered by a liposome, a viral vector, nanocarrier, or a microcarrier.

7. The method of claim 3, wherein the composition is delivered in multiple cycles of treatment.

8. The method of claim 1, wherein increasing the levels of microRNA-198 molecules causes improvement by inhibiting migration, invasion, proliferation, tumor growth, metastatic potential, tumorigenesis or a combination thereof of the cancer.

9. The method of claim 1, wherein the individual is further provided one or more additional anti-cancer therapies.

10. The method of claim 9, wherein the additional anti-cancer therapy comprises chemotherapy, radiotherapy, immunotherapy, gene therapy, surgery, non-microRNA-198 microRNA, siRNA or a combination thereof.

* * * * *

UNITED STATES PATENT AND TRADEMARK OFFICE
CERTIFICATE OF CORRECTION

PATENT NO. : 12,134,769 B2
APPLICATION NO. : 17/236851
DATED : November 5, 2024
INVENTOR(S) : Qizhi Yao et al.

Page 1 of 1

It is certified that error appears in the above-identified patent and that said Letters Patent is hereby corrected as shown below:

In the Claims

At Column 101, Claim number 1, Line number 60, should read as follows:
1. A method of treating cancer in an individual, comprising the step of delivering to the individual an effective amount of a composition comprising an agent that increases the level of microRNA-198 molecules in cancer cells of the individual, wherein the cancer is of the stomach or bone.

Signed and Sealed this
Seventh Day of January, 2025

Derrick Brent
*Acting Director of the United States Patent and Trademark Office*

SEQUENCE LISTING

<160> NUMBER OF SEQ ID NOS: 156

<210> SEQ ID NO 1
<211> LENGTH: 19
<212> TYPE: RNA
<213> ORGANISM: Homo sapiens

<400> SEQUENCE: 1

```
gguccagagg ggagauagg                                              19

<210> SEQ ID NO 2
<211> LENGTH: 22
<212> TYPE: RNA
<213> ORGANISM: Homo sapiens

<400> SEQUENCE: 2
ugagguagua gguuguauag uu                                          22

<210> SEQ ID NO 3
<211> LENGTH: 22
<212> TYPE: RNA
<213> ORGANISM: Homo sapiens

<400> SEQUENCE: 3
ugagguagua gguuguaugg uu                                          22

<210> SEQ ID NO 4
<211> LENGTH: 21
<212> TYPE: RNA
<213> ORGANISM: Homo sapiens

<400> SEQUENCE: 4
agagguagua gguugcauag u                                           21

<210> SEQ ID NO 5
<211> LENGTH: 22
<212> TYPE: RNA
<213> ORGANISM: Homo sapiens

<400> SEQUENCE: 5
ugagguagua gauuguauag uu                                          22

<210> SEQ ID NO 6
<211> LENGTH: 22
<212> TYPE: RNA
<213> ORGANISM: Homo sapiens

<400> SEQUENCE: 6
uggaagacua gugauuuugu ug                                          22

<210> SEQ ID NO 7
<211> LENGTH: 21
<212> TYPE: RNA
<213> ORGANISM: Homo sapiens

<400> SEQUENCE: 7
uauugcacuu gucccggccu g                                           21

<210> SEQ ID NO 8
<211> LENGTH: 22
<212> TYPE: RNA
<213> ORGANISM: Homo sapiens

<400> SEQUENCE: 8
aaagugcugu ucgugcaggu ag                                          22

<210> SEQ ID NO 9
<211> LENGTH: 23
<212> TYPE: RNA
<213> ORGANISM: Homo sapiens
```

```
<400> SEQUENCE: 9
ucuuugguua ucuagcugua uga                                              23

<210> SEQ ID NO 10
<211> LENGTH: 22
<212> TYPE: RNA
<213> ORGANISM: Homo sapiens

<400> SEQUENCE: 10
uacaguacug ugauaacuga ag                                               22

<210> SEQ ID NO 11
<211> LENGTH: 23
<212> TYPE: RNA
<213> ORGANISM: Homo sapiens

<400> SEQUENCE: 11
agcagcauug uacagggcua uga                                              23

<210> SEQ ID NO 12
<211> LENGTH: 24
<212> TYPE: RNA
<213> ORGANISM: Homo sapiens

<400> SEQUENCE: 12
aaaagugcuu acagugcagg uagc                                             24

<210> SEQ ID NO 13
<211> LENGTH: 21
<212> TYPE: RNA
<213> ORGANISM: Homo sapiens

<400> SEQUENCE: 13
uaaagugcug acagugcaga u                                                21

<210> SEQ ID NO 14
<211> LENGTH: 23
<212> TYPE: RNA
<213> ORGANISM: Homo sapiens

<400> SEQUENCE: 14
agcagcauug uacagggcua uca                                              23

<210> SEQ ID NO 15
<211> LENGTH: 22
<212> TYPE: RNA
<213> ORGANISM: Homo sapiens

<400> SEQUENCE: 15
uacccuguag aaccgaauuu gu                                               22

<210> SEQ ID NO 16
<211> LENGTH: 21
<212> TYPE: RNA
<213> ORGANISM: Homo sapiens

<400> SEQUENCE: 16
uggaauguaa agaaguaugu a                                                21

<210> SEQ ID NO 17
<211> LENGTH: 23
<212> TYPE: RNA
<213> ORGANISM: Homo sapiens
```

```
<400> SEQUENCE: 17
uggaguguga caauguguu ugu                                          23

<210> SEQ ID NO 18
<211> LENGTH: 23
<212> TYPE: RNA
<213> ORGANISM: Homo sapiens

<400> SEQUENCE: 18
ucccugagac ccuuuaaccu gug                                         23

<210> SEQ ID NO 19
<211> LENGTH: 22
<212> TYPE: RNA
<213> ORGANISM: Homo sapiens

<400> SEQUENCE: 19
ucccugagac ccuaacuugu ga                                          22

<210> SEQ ID NO 20
<211> LENGTH: 21
<212> TYPE: RNA
<213> ORGANISM: Homo sapiens

<400> SEQUENCE: 20
cauuauuacu uuugguacgc g                                           21

<210> SEQ ID NO 21
<211> LENGTH: 22
<212> TYPE: RNA
<213> ORGANISM: Homo sapiens

<400> SEQUENCE: 21
ucacagugaa ccggucucuu uc                                          22

<210> SEQ ID NO 22
<211> LENGTH: 22
<212> TYPE: RNA
<213> ORGANISM: Homo sapiens

<400> SEQUENCE: 22
uaacagucua cagccauggu cg                                          22

<210> SEQ ID NO 23
<211> LENGTH: 22
<212> TYPE: RNA
<213> ORGANISM: Homo sapiens

<400> SEQUENCE: 23
uugguccccu ucaaccagcu gu                                          22

<210> SEQ ID NO 24
<211> LENGTH: 21
<212> TYPE: RNA
<213> ORGANISM: Homo sapiens

<400> SEQUENCE: 24
ugugacuggu ugaccagagg g                                           21

<210> SEQ ID NO 25
<211> LENGTH: 22
<212> TYPE: RNA
```

```
<213> ORGANISM: Homo sapiens

<400> SEQUENCE: 25
uauggcuuuu cauuccuaug ug                                       22

<210> SEQ ID NO 26
<211> LENGTH: 23
<212> TYPE: RNA
<213> ORGANISM: Homo sapiens

<400> SEQUENCE: 26
acuccauuug uuuugaugau gga                                      23

<210> SEQ ID NO 27
<211> LENGTH: 22
<212> TYPE: RNA
<213> ORGANISM: Homo sapiens

<400> SEQUENCE: 27
uauugcuuaa gaauacgcgu ag                                       22

<210> SEQ ID NO 28
<211> LENGTH: 21
<212> TYPE: RNA
<213> ORGANISM: Homo sapiens

<400> SEQUENCE: 28
agugguuuua cccuauggua g                                        21

<210> SEQ ID NO 29
<211> LENGTH: 22
<212> TYPE: RNA
<213> ORGANISM: Homo sapiens

<400> SEQUENCE: 29
uaacacuguc ugguaaagau gg                                       22

<210> SEQ ID NO 30
<211> LENGTH: 23
<212> TYPE: RNA
<213> ORGANISM: Homo sapiens

<400> SEQUENCE: 30
uguaguguuu ccuacuuuau gga                                      23

<210> SEQ ID NO 31
<211> LENGTH: 22
<212> TYPE: RNA
<213> ORGANISM: Homo sapiens

<400> SEQUENCE: 31
ugagaugaag cacuguagcu ca                                       22

<210> SEQ ID NO 32
<211> LENGTH: 24
<212> TYPE: RNA
<213> ORGANISM: Homo sapiens

<400> SEQUENCE: 32
guccaguuuu cccaggaauc ccuu                                     24

<210> SEQ ID NO 33
<211> LENGTH: 22
```

```
<212> TYPE: RNA
<213> ORGANISM: Homo sapiens

<400> SEQUENCE: 33
ugagaacuga auccaugggu uu                                          22

<210> SEQ ID NO 34
<211> LENGTH: 22
<212> TYPE: RNA
<213> ORGANISM: Homo sapiens

<400> SEQUENCE: 34
ucuggcuccg ugucuucacu cc                                          22

<210> SEQ ID NO 35
<211> LENGTH: 22
<212> TYPE: RNA
<213> ORGANISM: Homo sapiens

<400> SEQUENCE: 35
ucucccaacc cuuguaccag ug                                          22

<210> SEQ ID NO 36
<211> LENGTH: 22
<212> TYPE: RNA
<213> ORGANISM: Homo sapiens

<400> SEQUENCE: 36
acuagacuga agcuccuuga gg                                          22

<210> SEQ ID NO 37
<211> LENGTH: 20
<212> TYPE: RNA
<213> ORGANISM: Homo sapiens

<400> SEQUENCE: 37
uugcauaguc acaaaaguga                                             20

<210> SEQ ID NO 38
<211> LENGTH: 22
<212> TYPE: RNA
<213> ORGANISM: Homo sapiens

<400> SEQUENCE: 38
uagguuaucc guguugccuu cg                                          22

<210> SEQ ID NO 39
<211> LENGTH: 22
<212> TYPE: RNA
<213> ORGANISM: Homo sapiens

<400> SEQUENCE: 39
uuaaugcuaa ucgugauagg gg                                          22

<210> SEQ ID NO 40
<211> LENGTH: 22
<212> TYPE: RNA
<213> ORGANISM: Homo sapiens

<400> SEQUENCE: 40
uagcagcaca uaaugguuug ug                                          22

<210> SEQ ID NO 41
```

```
<211> LENGTH: 22
<212> TYPE: RNA
<213> ORGANISM: Homo sapiens

<400> SEQUENCE: 41
uagcagcaca ucaugguuua ca                                              22

<210> SEQ ID NO 42
<211> LENGTH: 22
<212> TYPE: RNA
<213> ORGANISM: Homo sapiens

<400> SEQUENCE: 42
uagcagcacg uaaauauugg cg                                              22

<210> SEQ ID NO 43
<211> LENGTH: 20
<212> TYPE: RNA
<213> ORGANISM: Homo sapiens

<400> SEQUENCE: 43
acugcaguga aggcacuugu                                                 20

<210> SEQ ID NO 44
<211> LENGTH: 24
<212> TYPE: RNA
<213> ORGANISM: Homo sapiens

<400> SEQUENCE: 44
caaagugcuu acagugcagg uagu                                            24

<210> SEQ ID NO 45
<211> LENGTH: 23
<212> TYPE: RNA
<213> ORGANISM: Homo sapiens

<400> SEQUENCE: 45
aacauucaac gcugucggug agu                                             23

<210> SEQ ID NO 46
<211> LENGTH: 22
<212> TYPE: RNA
<213> ORGANISM: Homo sapiens

<400> SEQUENCE: 46
aacauucauu gcugucggug gg                                              22

<210> SEQ ID NO 47
<211> LENGTH: 22
<212> TYPE: RNA
<213> ORGANISM: Homo sapiens

<400> SEQUENCE: 47
aacauucaac cugucgguga gu                                              22

<210> SEQ ID NO 48
<211> LENGTH: 24
<212> TYPE: RNA
<213> ORGANISM: Homo sapiens

<400> SEQUENCE: 48
aacauucauu guugucggug gguu                                            24
```

```
<210> SEQ ID NO 49
<211> LENGTH: 23
<212> TYPE: RNA
<213> ORGANISM: Homo sapiens

<400> SEQUENCE: 49
uauggcacug guagaauuca cug                                              23

<210> SEQ ID NO 50
<211> LENGTH: 18
<212> TYPE: RNA
<213> ORGANISM: Homo sapiens

<400> SEQUENCE: 50
uggagagaaa ggcaguuc                                                    18

<210> SEQ ID NO 51
<211> LENGTH: 21
<212> TYPE: RNA
<213> ORGANISM: Homo sapiens

<400> SEQUENCE: 51
agggccnccc cucaauccug u                                                21

<210> SEQ ID NO 52
<211> LENGTH: 23
<212> TYPE: RNA
<213> ORGANISM: Homo sapiens

<400> SEQUENCE: 52
caaagaauuc uccuuuuggg cuu                                              23

<210> SEQ ID NO 53
<211> LENGTH: 22
<212> TYPE: RNA
<213> ORGANISM: Homo sapiens

<400> SEQUENCE: 53
caucccuugc augguggagg gu                                               22

<210> SEQ ID NO 54
<211> LENGTH: 22
<212> TYPE: RNA
<213> ORGANISM: Homo sapiens

<400> SEQUENCE: 54
uaaggugcau cuagugcaga ua                                               22

<210> SEQ ID NO 55
<211> LENGTH: 22
<212> TYPE: RNA
<213> ORGANISM: Homo sapiens

<400> SEQUENCE: 55
ugauauguuu gauauauuag gu                                               22

<210> SEQ ID NO 56
<211> LENGTH: 22
<212> TYPE: RNA
<213> ORGANISM: Homo sapiens

<400> SEQUENCE: 56
caacggaauc ccaaaagcag cu                                               22
```

```
<210> SEQ ID NO 57
<211> LENGTH: 21
<212> TYPE: RNA
<213> ORGANISM: Homo sapiens

<400> SEQUENCE: 57
cugaccuaug aauugacagc c                                              21

<210> SEQ ID NO 58
<211> LENGTH: 22
<212> TYPE: RNA
<213> ORGANISM: Homo sapiens

<400> SEQUENCE: 58
uguaacagca acuccaugug ga                                             22

<210> SEQ ID NO 59
<211> LENGTH: 21
<212> TYPE: RNA
<213> ORGANISM: Homo sapiens

<400> SEQUENCE: 59
uagcagcaca gaaauauugg c                                              21

<210> SEQ ID NO 60
<211> LENGTH: 21
<212> TYPE: RNA
<213> ORGANISM: Homo sapiens

<400> SEQUENCE: 60
uagguaguuu cauguuguug g                                              21

<210> SEQ ID NO 61
<211> LENGTH: 22
<212> TYPE: RNA
<213> ORGANISM: Homo sapiens

<400> SEQUENCE: 61
uucaccaccu ucuccaccca gc                                             22

<210> SEQ ID NO 62
<211> LENGTH: 23
<212> TYPE: RNA
<213> ORGANISM: Homo sapiens

<400> SEQUENCE: 62
cccaguguuc agacuaccug uuc                                            23

<210> SEQ ID NO 63
<211> LENGTH: 23
<212> TYPE: RNA
<213> ORGANISM: Homo sapiens

<400> SEQUENCE: 63
cccaguguuu agacuaucug uuc                                            23

<210> SEQ ID NO 64
<211> LENGTH: 22
<212> TYPE: RNA
<213> ORGANISM: Homo sapiens

<400> SEQUENCE: 64
uguaaacauc cuacacucag cu                                             22
```

```
<210> SEQ ID NO 65
<211> LENGTH: 23
<212> TYPE: RNA
<213> ORGANISM: Homo sapiens

<400> SEQUENCE: 65
ugugcaaauc uaugcaaaac uga                                              23

<210> SEQ ID NO 66
<211> LENGTH: 23
<212> TYPE: RNA
<213> ORGANISM: Homo sapiens

<400> SEQUENCE: 66
ugugcaaauc caugcaaaac uga                                              23

<210> SEQ ID NO 67
<211> LENGTH: 22
<212> TYPE: RNA
<213> ORGANISM: Homo sapiens

<400> SEQUENCE: 67
uucaacgggu auuuauugag ca                                               22

<210> SEQ ID NO 68
<211> LENGTH: 23
<212> TYPE: RNA
<213> ORGANISM: Homo sapiens

<400> SEQUENCE: 68
uaaagugcuu auagugcagg uag                                              23

<210> SEQ ID NO 69
<211> LENGTH: 22
<212> TYPE: RNA
<213> ORGANISM: Homo sapiens

<400> SEQUENCE: 69
uaacacuguc ugguaacgau gu                                               22

<210> SEQ ID NO 70
<211> LENGTH: 23
<212> TYPE: RNA
<213> ORGANISM: Homo sapiens

<400> SEQUENCE: 70
uaauacugcc ugguaaugau gac                                              23

<210> SEQ ID NO 71
<211> LENGTH: 22
<212> TYPE: RNA
<213> ORGANISM: Homo sapiens

<400> SEQUENCE: 71
uaauacugcc ggguaaugau gg                                               22

<210> SEQ ID NO 72
<211> LENGTH: 22
<212> TYPE: RNA
<213> ORGANISM: Homo sapiens

<400> SEQUENCE: 72
```
agagguauag ggcaugggaa aa                                          22

<210> SEQ ID NO 73
<211> LENGTH: 22
<212> TYPE: RNA
<213> ORGANISM: Homo sapiens

<400> SEQUENCE: 73
gugaaauguu uaggaccacu ag                                          22

<210> SEQ ID NO 74
<211> LENGTH: 22
<212> TYPE: RNA
<213> ORGANISM: Homo sapiens

<400> SEQUENCE: 74
uucccuuugu cauccuaugc cu                                          22

<210> SEQ ID NO 75
<211> LENGTH: 22
<212> TYPE: RNA
<213> ORGANISM: Homo sapiens

<400> SEQUENCE: 75
uccuucauuc caccggaguc ug                                          22

<210> SEQ ID NO 76
<211> LENGTH: 22
<212> TYPE: RNA
<213> ORGANISM: Homo sapiens

<400> SEQUENCE: 76
uggaauguaa ggaagugugu gg                                          22

<210> SEQ ID NO 77
<211> LENGTH: 22
<212> TYPE: RNA
<213> ORGANISM: Homo sapiens

<400> SEQUENCE: 77
uagcuuauca gacugauguu ga                                          22

<210> SEQ ID NO 78
<211> LENGTH: 22
<212> TYPE: RNA
<213> ORGANISM: Homo sapiens

<400> SEQUENCE: 78
cugugcgugu gacagcggcu ga                                          22

<210> SEQ ID NO 79
<211> LENGTH: 21
<212> TYPE: RNA
<213> ORGANISM: Homo sapiens

<400> SEQUENCE: 79
acagcaggca cagacaggca g                                           21

<210> SEQ ID NO 80
<211> LENGTH: 21
<212> TYPE: RNA
<213> ORGANISM: Homo sapiens

<400> SEQUENCE: 80

```
augaccuaug aauugacaga c                                                 21

<210> SEQ ID NO 81
<211> LENGTH: 23
<212> TYPE: RNA
<213> ORGANISM: Homo sapiens

<400> SEQUENCE: 81
aaagugcugc gacauuugag cgu                                               23

<210> SEQ ID NO 82
<211> LENGTH: 23
<212> TYPE: RNA
<213> ORGANISM: Homo sapiens

<400> SEQUENCE: 82
gaagugcuuc gauuuugggg ugu                                               23

<210> SEQ ID NO 83
<211> LENGTH: 22
<212> TYPE: RNA
<213> ORGANISM: Homo sapiens

<400> SEQUENCE: 83
aagcugccag uugaagaacu gu                                                22

<210> SEQ ID NO 84
<211> LENGTH: 21
<212> TYPE: RNA
<213> ORGANISM: Homo sapiens

<400> SEQUENCE: 84
cccagauaau ggcacucuca a                                                 21

<210> SEQ ID NO 85
<211> LENGTH: 23
<212> TYPE: RNA
<213> ORGANISM: Homo sapiens

<400> SEQUENCE: 85
agcuacauug ucugcuggguu uuc                                              23

<210> SEQ ID NO 86
<211> LENGTH: 24
<212> TYPE: RNA
<213> ORGANISM: Homo sapiens

<400> SEQUENCE: 86
agcuacaucu ggcuacuggg ucuc                                              24

<210> SEQ ID NO 87
<211> LENGTH: 21
<212> TYPE: RNA
<213> ORGANISM: Homo sapiens

<400> SEQUENCE: 87
ugucaguuug ucaaauaccc c                                                 21

<210> SEQ ID NO 88
<211> LENGTH: 23
<212> TYPE: RNA
<213> ORGANISM: Homo sapiens
```

```
<400> SEQUENCE: 88
caagucacua gugguuccgu uua                                              23

<210> SEQ ID NO 89
<211> LENGTH: 21
<212> TYPE: RNA
<213> ORGANISM: Homo sapiens

<400> SEQUENCE: 89
aucacauugc cagggauuuc c                                                21

<210> SEQ ID NO 90
<211> LENGTH: 22
<212> TYPE: RNA
<213> ORGANISM: Homo sapiens

<400> SEQUENCE: 90
uggcucaguu cagcaggaac ag                                               22

<210> SEQ ID NO 91
<211> LENGTH: 22
<212> TYPE: RNA
<213> ORGANISM: Homo sapiens

<400> SEQUENCE: 91
cauugcacuu gucucggucu ga                                               22

<210> SEQ ID NO 92
<211> LENGTH: 21
<212> TYPE: RNA
<213> ORGANISM: Homo sapiens

<400> SEQUENCE: 92
uucaaguaau ccaggauagg c                                                21

<210> SEQ ID NO 93
<211> LENGTH: 22
<212> TYPE: RNA
<213> ORGANISM: Homo sapiens

<400> SEQUENCE: 93
uucaaguaau ucaggauagg uu                                               22

<210> SEQ ID NO 94
<211> LENGTH: 21
<212> TYPE: RNA
<213> ORGANISM: Homo sapiens

<400> SEQUENCE: 94
uucacagugg cuaaguuccg c                                                21

<210> SEQ ID NO 95
<211> LENGTH: 21
<212> TYPE: RNA
<213> ORGANISM: Homo sapiens

<400> SEQUENCE: 95
uucacagugg cuaaguucug c                                                21

<210> SEQ ID NO 96
<211> LENGTH: 23
<212> TYPE: RNA
<213> ORGANISM: Homo sapiens
```

```
<400> SEQUENCE: 96
uguaaacauc cuacacucuc agc                                              23

<210> SEQ ID NO 97
<211> LENGTH: 21
<212> TYPE: RNA
<213> ORGANISM: Homo sapiens

<400> SEQUENCE: 97
uagcaccauc ugaaaucggu u                                                21

<210> SEQ ID NO 98
<211> LENGTH: 23
<212> TYPE: RNA
<213> ORGANISM: Homo sapiens

<400> SEQUENCE: 98
uagcaccauu ugaaaucagu guu                                              23

<210> SEQ ID NO 99
<211> LENGTH: 20
<212> TYPE: RNA
<213> ORGANISM: Homo sapiens

<400> SEQUENCE: 99
uagcaccauu ugaaaucggu                                                  20

<210> SEQ ID NO 100
<211> LENGTH: 22
<212> TYPE: RNA
<213> ORGANISM: Homo sapiens

<400> SEQUENCE: 100
cuuucagucg gauguuugca gc                                               22

<210> SEQ ID NO 101
<211> LENGTH: 22
<212> TYPE: RNA
<213> ORGANISM: Homo sapiens

<400> SEQUENCE: 101
uguaaacauc cucgacugga ag                                               22

<210> SEQ ID NO 102
<211> LENGTH: 21
<212> TYPE: RNA
<213> ORGANISM: Homo sapiens

<400> SEQUENCE: 102
caccacguuu auacgccggu g                                                21

<210> SEQ ID NO 103
<211> LENGTH: 21
<212> TYPE: DNA
<213> ORGANISM: Artificial Sequence
<220> FEATURE:
<223> OTHER INFORMATION: Synthetic Primer

<400> SEQUENCE: 103
ctcaacccag atgcgttctc g                                                21

<210> SEQ ID NO 104
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 104
aggtccacat tggccttcgt                                                   20

<210> SEQ ID NO 105
<211> LENGTH: 20
<212> TYPE: DNA
<213> ORGANISM: Artificial Sequence
<220> FEATURE:
<223> OTHER INFORMATION: Synthetic Primer

<400> SEQUENCE: 105
tcagcatgac agacctccag                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic Primer

<400> SEQUENCE: 106
tcccagaaac tccatccaag                                                   20

<210> SEQ ID NO 107
<211> LENGTH: 21
<212> TYPE: DNA
<213> ORGANISM: Artificial Sequence
<220> FEATURE:
<223> OTHER INFORMATION: Synthetic Primer

<400> SEQUENCE: 107
tgagcgtgca gtcactcaat g                                                 21

<210> SEQ ID NO 108
<211> LENGTH: 22
<212> TYPE: DNA
<213> ORGANISM: Artificial Sequence
<220> FEATURE:
<223> OTHER INFORMATION: Synthetic Primer

<400> SEQUENCE: 108
cgagtccatc actgtatcct cc                                                22

<210> SEQ ID NO 109
<211> LENGTH: 20
<212> TYPE: DNA
<213> ORGANISM: Artificial Sequence
<220> FEATURE:
<223> OTHER INFORMATION: Synthetic Primer

<400> SEQUENCE: 109
tgcactgagt gtggaaaagc                                                   20

<210> SEQ ID NO 110
<211> LENGTH: 20
<212> TYPE: DNA
<213> ORGANISM: Artificial Sequence
<220> FEATURE:
<223> OTHER INFORMATION: Synthetic Primer

<400> SEQUENCE: 110
```
tggtgatgct gaaagagacg                                          20

<210> SEQ ID NO 111
<211> LENGTH: 20
<212> TYPE: DNA
<213> ORGANISM: Artificial Sequence
<220> FEATURE:
<223> OTHER INFORMATION: Synthetic Primer

<400> SEQUENCE: 111
cgtgaattct cacggcttcc                                          20

<210> SEQ ID NO 112
<211> LENGTH: 25
<212> TYPE: DNA
<213> ORGANISM: Artificial Sequence
<220> FEATURE:
<223> OTHER INFORMATION: Synthetic Primer

<400> SEQUENCE: 112
gcatcacaaa tttcacaaat aaagc                                    25

<210> SEQ ID NO 113
<211> LENGTH: 46
<212> TYPE: DNA
<213> ORGANISM: Artificial Sequence
<220> FEATURE:
<223> OTHER INFORMATION: Synthetic Primer

<400> SEQUENCE: 113
gggatgctat ttcagccaaa agcttcactt ctttatactc tcttcc             46

<210> SEQ ID NO 114
<211> LENGTH: 46
<212> TYPE: DNA
<213> ORGANISM: Artificial Sequence
<220> FEATURE:
<223> OTHER INFORMATION: Synthetic Primer

<400> SEQUENCE: 114
cctacgataa agtcggtttt cgaagtgaag aaatatgaga gaaggg             46

<210> SEQ ID NO 115
<211> LENGTH: 43
<212> TYPE: DNA
<213> ORGANISM: Artificial Sequence
<220> FEATURE:
<223> OTHER INFORMATION: Synthetic Primer

<400> SEQUENCE: 115
cttctttggg atgctatttc agccaatact tctttatact ctc                43

<210> SEQ ID NO 116
<211> LENGTH: 43
<212> TYPE: DNA
<213> ORGANISM: Artificial Sequence
<220> FEATURE:
<223> OTHER INFORMATION: Synthetic Primer

<400> SEQUENCE: 116
gagagtataa agaagtattg gctgaaatag catcccaaag aag                43

<210> SEQ ID NO 117
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 117
cgtgaattct cacggcttcc                                                    20

<210> SEQ ID NO 118
<211> LENGTH: 25
<212> TYPE: DNA
<213> ORGANISM: Artificial Sequence
<220> FEATURE:
<223> OTHER INFORMATION: Synthetic Primer

<400> SEQUENCE: 118
gcatcacaaa tttcacaaat aaagc                                              25

<210> SEQ ID NO 119
<211> LENGTH: 37
<212> TYPE: DNA
<213> ORGANISM: Artificial Sequence
<220> FEATURE:
<223> OTHER INFORMATION: Synthetic Primer

<400> SEQUENCE: 119
cctggacgcc ctcccactag atctgctgct attctca                                 37

<210> SEQ ID NO 120
<211> LENGTH: 38
<212> TYPE: DNA
<213> ORGANISM: Artificial Sequence
<220> FEATURE:
<223> OTHER INFORMATION: Synthetic Primer

<400> SEQUENCE: 120
ggacctgcgg gagggtgatc tagacgacga taaggagt                                38

<210> SEQ ID NO 121
<211> LENGTH: 34
<212> TYPE: DNA
<213> ORGANISM: Artificial Sequence
<220> FEATURE:
<223> OTHER INFORMATION: Synthetic Primer

<400> SEQUENCE: 121
gcctgctgcc cgtggtagga cagcccatca tccg                                    34

<210> SEQ ID NO 122
<211> LENGTH: 34
<212> TYPE: DNA
<213> ORGANISM: Artificial Sequence
<220> FEATURE:
<223> OTHER INFORMATION: Synthetic Primer

<400> SEQUENCE: 122
cggacgacgg gcaccatcct gtcgggtagt aggc                                    34

<210> SEQ ID NO 123
<211> LENGTH: 44
<212> TYPE: DNA
<213> ORGANISM: Artificial Sequence
<220> FEATURE:
<223> OTHER INFORMATION: Synthetic Primer

<400> SEQUENCE: 123
cgagtctgtg atccagcact taggatacct cttcctcaag atga                         44
```

```
<210> SEQ ID NO 124
<211> LENGTH: 44
<212> TYPE: DNA
<213> ORGANISM: Artificial Sequence
<220> FEATURE:
<223> OTHER INFORMATION: Synthetic Primer

<400> SEQUENCE: 124
gctcagacac taggtcgtga atcctatgga gaaggagttc tact            44

<210> SEQ ID NO 125
<211> LENGTH: 23
<212> TYPE: RNA
<213> ORGANISM: Homo sapiens

<400> SEQUENCE: 125
ugcuauuuca gccaaucugg aca                                   23

<210> SEQ ID NO 126
<211> LENGTH: 18
<212> TYPE: RNA
<213> ORGANISM: Homo sapiens

<400> SEQUENCE: 126
acagucugac ucuggaca                                         18

<210> SEQ ID NO 127
<211> LENGTH: 42
<212> TYPE: RNA
<213> ORGANISM: Homo sapiens

<400> SEQUENCE: 127
uuugggaugc uauuucagcc aaucuggaca cuucuuuaua cu              42

<210> SEQ ID NO 128
<211> LENGTH: 8
<212> TYPE: DNA
<213> ORGANISM: Homo sapiens

<400> SEQUENCE: 128 cctgggct                                                     8

<210> SEQ ID NO 129
<211> LENGTH: 42
<212> TYPE: RNA
<213> ORGANISM: Homo sapiens

<400> SEQUENCE: 129
ugcgggacgc ugucucagcc ugccuggaca cuucuuuaua cu              42

<210> SEQ ID NO 130
<211> LENGTH: 8
<212> TYPE: DNA
<213> ORGANISM: Homo sapiens

<400> SEQUENCE: 130 cttaggat                                                     8

<210> SEQ ID NO 131
<211> LENGTH: 42
<212> TYPE: RNA
<213> ORGANISM: Homo sapiens
```

```
<400> SEQUENCE: 131
uucgggaugc uauuucagcc aaucuggaca cuucuuucua cu          42

<210> SEQ ID NO 132
<211> LENGTH: 42
<212> TYPE: RNA
<213> ORGANISM: Homo sapiens

<400> SEQUENCE: 132
cuugggaugc uauuucagcc aaucuggaca cuucuuuaua cu          42

<210> SEQ ID NO 133
<211> LENGTH: 42
<212> TYPE: RNA
<213> ORGANISM: Homo sapiens

<400> SEQUENCE: 133
ucugggaugc uuuuucaucc aaucuggaca cuucuuuaua cu          42

<210> SEQ ID NO 134
<211> LENGTH: 43
<212> TYPE: RNA
<213> ORGANISM: Homo sapiens

<400> SEQUENCE: 134
ucugggaugc uuuuuucagc caaucuggac acuucuuuau acu          43

<210> SEQ ID NO 135
<211> LENGTH: 41
<212> TYPE: RNA
<213> ORGANISM: Homo sapiens

<400> SEQUENCE: 135
caguucagcu acagucugac ucuggacagg ggguuucugu u          41

<210> SEQ ID NO 136
<211> LENGTH: 41
<212> TYPE: RNA
<213> ORGANISM: Homo sapiens

<400> SEQUENCE: 136
caguucagcc ccagucagac ucuggacagg gguuuccugu u          41

<210> SEQ ID NO 137
<211> LENGTH: 41
<212> TYPE: RNA
<213> ORGANISM: Homo sapiens

<400> SEQUENCE: 137
caguucagcc ccagucagac ucuggacagg gguuuucugu u          41

<210> SEQ ID NO 138
<211> LENGTH: 41
<212> TYPE: RNA
<213> ORGANISM: Homo sapiens

<400> SEQUENCE: 138
caguucagcu acagucagac ucuggacagg ggguuucugu u          41

<210> SEQ ID NO 139
<211> LENGTH: 41
<212> TYPE: RNA
<213> ORGANISM: Homo sapiens
```

-continued

<400> SEQUENCE: 139
caguucaacu acagucagac uuuggacagg ggguuucugu u                41

<210> SEQ ID NO 140
<211> LENGTH: 41
<212> TYPE: RNA
<213> ORGANISM: Homo sapiens

<400> SEQUENCE: 140
caguucagcu auagucagac ucuggacagg ggauuucugu u                41

<210> SEQ ID NO 141
<211> LENGTH: 40
<212> TYPE: RNA
<213> ORGANISM: Homo sapiens

<400> SEQUENCE: 141
caguucagcu acagucagau ucuggacagg gguuucuguu                 40

<210> SEQ ID NO 142
<211> LENGTH: 41
<212> TYPE: RNA
<213> ORGANISM: Homo sapiens

<400> SEQUENCE: 142
caguucagcu acagucagac ucuggacagg ggguuucugu u                41

<210> SEQ ID NO 143
<211> LENGTH: 42
<212> TYPE: RNA
<213> ORGANISM: Homo sapiens

<400> SEQUENCE: 143
caguucagcu acagucagac ucuggacaag gggcuuucug uu               42

<210> SEQ ID NO 144
<211> LENGTH: 41
<212> TYPE: RNA
<213> ORGANISM: Homo sapiens

<400> SEQUENCE: 144
caguucagcu acagucagac ucuggacagg ggguuacugu u                41

<210> SEQ ID NO 145
<211> LENGTH: 41
<212> TYPE: RNA
<213> ORGANISM: Homo sapiens

<400> SEQUENCE: 145
caauucaacu acagucagac ucuggacaga ggguuucugu u                41

<210> SEQ ID NO 146
<211> LENGTH: 39
<212> TYPE: RNA
<213> ORGANISM: Homo sapiens

<400> SEQUENCE: 146
caguucagcu auagucagac ucuggacggg gguucuguu                  39

<210> SEQ ID NO 147
<211> LENGTH: 40
<212> TYPE: RNA

<213> ORGANISM: Homo sapiens

<400> SEQUENCE: 147
ugguuccgcu acagucagac ucuggauagg gcuuucuuuu          40

<210> SEQ ID NO 148
<211> LENGTH: 41
<212> TYPE: RNA
<213> ORGANISM: Homo sapiens

<400> SEQUENCE: 148
caguuaagcu gcagucagac ucuggacagg ggguuucugu u        41

<210> SEQ ID NO 149
<211> LENGTH: 41
<212> TYPE: RNA
<213> ORGANISM: Homo sapiens

<400> SEQUENCE: 149
cgacgcagcu gcagccggac ucuggauagg ugauuucugu u        41

<210> SEQ ID NO 150
<211> LENGTH: 42
<212> TYPE: RNA
<213> ORGANISM: Homo sapiens

<400> SEQUENCE: 150
caguguaggu gcacgucaga cuuuguacag gggauguuuu cu       42

<210> SEQ ID NO 151
<211> LENGTH: 490
<212> TYPE: DNA
<213> ORGANISM: Homo sapiens

<400> SEQUENCE: 151
cttcatcagt gacctcccct acagaaggcc ctggcagtgt tcactctgat acctccaact      60
gatctcccag caatcgcatc ccggctgacc ctgtgcccca gttggggcag ggcaggagg     120
gagggtttct ctcccaacgc tgaagcggtc agactggagg tcgaagcaat cagcaaacac    180
aataagagtc tccttctctt ctcttctttg ggatgctatt tcagccaatc tggacacttc    240
tttatactct cttccctttt ttttctggta gaagccaccc ttccctgcct ccagctgtca    300
gcctggtttt cgtcatcttc cctgcccctg tgcctctgtc ctagactccc ggggtccccg    360
ccctctctca tatcactgaa ggatattttc aacaattaga ggaatttaaa gaggaaaaaa    420
attacaaaga aaataataaa agtgtttgta cgttttcatg ctggtggttt gaggagccaa    480
atttacctca                                                           490

<210> SEQ ID NO 152
<211> LENGTH: 490
<212> TYPE: DNA
<213> ORGANISM: Homo sapiens

<400> SEQUENCE: 152
cttcatcagt gacctcccct acagaaggcc ctggcagtgt tcactctgat acctccaact      60
gatctcccag caatcgcatc ccggctgacc ctgtgcccca gttggggcag ggcaggagg     120
gagggtttct ctcccaacgc tgaagcggtc agactggagg tcgaagcaat cagcaaacac    180
aataagagtc tccttctctt ctcttctttg ggatgctatt tcagccaaaa gcttcacttc    240
tttatactct cttccctttt ttttctggta gaagccaccc ttccctgcct ccagctgtca    300

```
gcctggtttt cgtcatcttc cctgccctg tgcctctgtc ctagactccc ggggtccccg      360
ccctctctca tatcactgaa ggatattttc aacaattaga ggaatttaaa gaggaaaaaa      420
attacaaaga aaataataaa agtgtttgta cgttttcatg ctggtggttt gaggagccaa      480
atttacctca                                                             490

<210> SEQ ID NO 153
<211> LENGTH: 482
<212> TYPE: DNA
<213> ORGANISM: Homo sapiens

<400> SEQUENCE: 153
cttcatcagt gacctcccct acagaaggcc ctggcagtgt tcactctgat acctccaact       60
gatctcccag caatcgcatc ccggctgacc ctgtgcccca gttggggcag gggcaggagg      120
gagggtttct ctcccaacgc tgaagcggtc agactggagg tcgaagcaat cagcaaacac      180
aataagagtc tccttctctt ctcttctttg ggatgctatt tcagccaact tctttatact      240
ctcttccctt ttttttctgg tagaagccac ccttccctgc ctccagctgt cagcctggtt      300
ttcgtcatct tccctgcccc tgtgcctctg tcctagactc ccggggtccc cgccctctct      360
catatcactg aaggatattt tcaacaatta gaggaattta agaggaaaa aaattacaaa       420 gaaaataata aaagtgtttg tacgttttca tgctggtggt ttgaggagcc aaatttacct      480
ca                                                                     482

<210> SEQ ID NO 154
<211> LENGTH: 22
<212> TYPE: DNA
<213> ORGANISM: Homo sapiens

<400> SEQUENCE: 154
ggcctgctgc ccgtgctggg cc                                               22

<210> SEQ ID NO 155
<211> LENGTH: 22
<212> TYPE: DNA
<213> ORGANISM: Homo sapiens

<400> SEQUENCE: 155
tctgtgatcc agcacctggg ct                                               22

<210> SEQ ID NO 156
<211> LENGTH: 18
<212> TYPE: DNA
<213> ORGANISM: Homo sapiens

<400> SEQUENCE: 156
acgccctccc attggacc                                                    18
```